(12) United States Patent
Panter et al.

(10) Patent No.: US 12,383,399 B2
(45) Date of Patent: Aug. 12, 2025

(54) EXPANDABLE FRAME FOR MEDICAL DEVICE

(71) Applicant: MiRus LLC, Marietta, GA (US)

(72) Inventors: Alex Panter, Marietta, GA (US); Jay Yadav, Atlanta, GA (US); Noah Roth, Marietta, GA (US)

(73) Assignee: MIRUS LLC, Marietta, GA (US)

( * ) Notice: Subject to any disclaimer, the term of this patent is extended or adjusted under 35 U.S.C. 154(b) by 0 days.

(21) Appl. No.: 18/602,873

(22) Filed: Mar. 12, 2024

(65) Prior Publication Data

US 2024/0216129 A1 Jul. 4, 2024

Related U.S. Application Data

(63) Continuation-in-part of application No. 18/418,007, filed on Jan. 19, 2024, and a continuation-in-part of
(Continued)

(51) Int. Cl.
*A61F 2/24* (2006.01)

(52) U.S. Cl.
CPC .......... *A61F 2/2418* (2013.01); *A61F 2/2436* (2013.01); *A61F 2310/00059* (2013.01)

(58) Field of Classification Search
CPC .................. A61F 2/2418; A61F 2/2436; A61F 2310/00059; A61F 2/24;
(Continued)

(56) References Cited

U.S. PATENT DOCUMENTS

| 11,266,767 B2 | 3/2022 | Roth et al. |
| 2003/0072974 A1 | 4/2003 | Lau et al. |

(Continued)

OTHER PUBLICATIONS

Matweb Material Property Data (Nitinol—NiTi Shape Memory Alloy, 1996-2024) https://www.matweb.com/search/DataSheet.aspx?MatGUID=44afc7d3c6eb4829bc2df27884fd2d6c&ckck=1 (Year: 1996).*

(Continued)

*Primary Examiner* — Jerrah Edwards
*Assistant Examiner* — Kia Xiong White
(74) *Attorney, Agent, or Firm* — UB Greensfelder LLP

(57) ABSTRACT

A prosthetic heart valve for the treatment of structural heart disease wherein the prosthetic heart valve includes an expandable frame that is formed of a rhenium containing metal alloy. The novel geometry of the expandable frame in combination with the frame being partially or fully formed of the rhenium containing alloy enables the formation of a frame that a) has an open cell geometry in the frame of the prosthetic heart valve that can be used to reduce delivery system size, b) has high radial strength, c) has improved restoration of the physiologic EOA, d) has lower recoil, e) has little or no longitudinal foreshortening, f) allows for proper placement of the bioprosthetic valve in relation to the native commissures of the valve, h) has symmetrical and cylindrical expansion of the prosthetic valve resulting in lower rates of leaflet thrombosis and structural valve deterioration, and i) prevents allergic response and restenosis associated with nickel content.

29 Claims, 21 Drawing Sheets

Related U.S. Application Data application No. 18/417,939, filed on Jan. 19, 2024, and a continuation-in-part of application No. 18/400,338, filed on Dec. 29, 2023, and a continuation-in-part of application No. 18/204,180, filed on May 31, 2023.

(60) Provisional application No. 63/540,556, filed on Sep. 26, 2023, provisional application No. 63/540,266, filed on Sep. 25, 2023, provisional application No. 63/439,892, filed on Jan. 19, 2023, provisional application No. 63/439,908, filed on Jan. 19, 2023, provisional application No. 63/389,281, filed on Jul. 14, 2022, provisional application No. 63/347,337, filed on May 31, 2022.

(58) Field of Classification Search
CPC . A61F 2002/91558; A61F 2002/91566; A61L 27/306; A61L 27/54
See application file for complete search history.

(56) References Cited

U.S. PATENT DOCUMENTS

| | | |
|---|---|---|
| 2003/0159920 A1 | 8/2003 | Roth |
| 2005/0033407 A1* | 2/2005 | Weber .................. A61F 2/91 |
| | | 623/1.15 |
| 2005/0079200 A1 | 4/2005 | Rathenow et al. |
| 2005/0191408 A1 | 9/2005 | Aharonov |
| 2006/0200224 A1 | 2/2006 | Furst et al. |
| 2006/0136051 A1 | 6/2006 | Furst et al. |
| 2006/0184251 A1 | 8/2006 | Zhang et al. |
| 2008/0183280 A1 | 7/2008 | Agnew |
| 2009/0068249 A1 | 3/2009 | Furst et al. |
| 2010/0016951 A1* | 1/2010 | Kim .................. A61F 2/915 |
| | | 623/1.16 |
| 2010/0023115 A1 | 1/2010 | Robain et al. |
| 2010/0298931 A1* | 11/2010 | Quadri .................. A61F 2/243 |
| | | 623/2.11 |
| 2013/0084322 A1 | 4/2013 | Wu |
| 2013/0172983 A1* | 7/2013 | Clerc .................. A61F 2/848 |
| | | 623/1.16 |
| 2013/0216421 A1 | 8/2013 | Buckman, Jr. et al. |
| 2014/0099279 A1 | 4/2014 | Furst et al. |
| 2015/0265400 A1* | 9/2015 | Eidenschink ......... A61F 2/2418 |
| | | 623/2.38 |
| 2016/0237541 A1* | 8/2016 | Patel .................. B21C 23/002 |
| 2017/0216494 A1 | 8/2017 | Roth et al. |
| 2017/0273785 A1 | 9/2017 | Seguin et al. |
| 2018/0361017 A1 | 12/2018 | Roth |
| 2019/0008995 A1 | 1/2019 | Roth |
| 2019/0046684 A1 | 2/2019 | Roth et al. |
| 2019/0224008 A1* | 7/2019 | Bressloff ............... A61F 2/2415 |
| 2020/0306067 A1 | 10/2020 | Nia |
| 2021/0186688 A1* | 6/2021 | Wheatley .............. A61F 2/2412 |
| 2021/0251766 A1 | 8/2021 | Quintana-Ponce et al. |

OTHER PUBLICATIONS

Pedowitz et al., "Molybdenum Rhenium (MoRe) as a Biologically Superior Alloy for Foot and Ankle Implant", Foot & Ankle Orthopaedics, vol. 3, p. 1 (Sep. 2018).

* cited by examiner

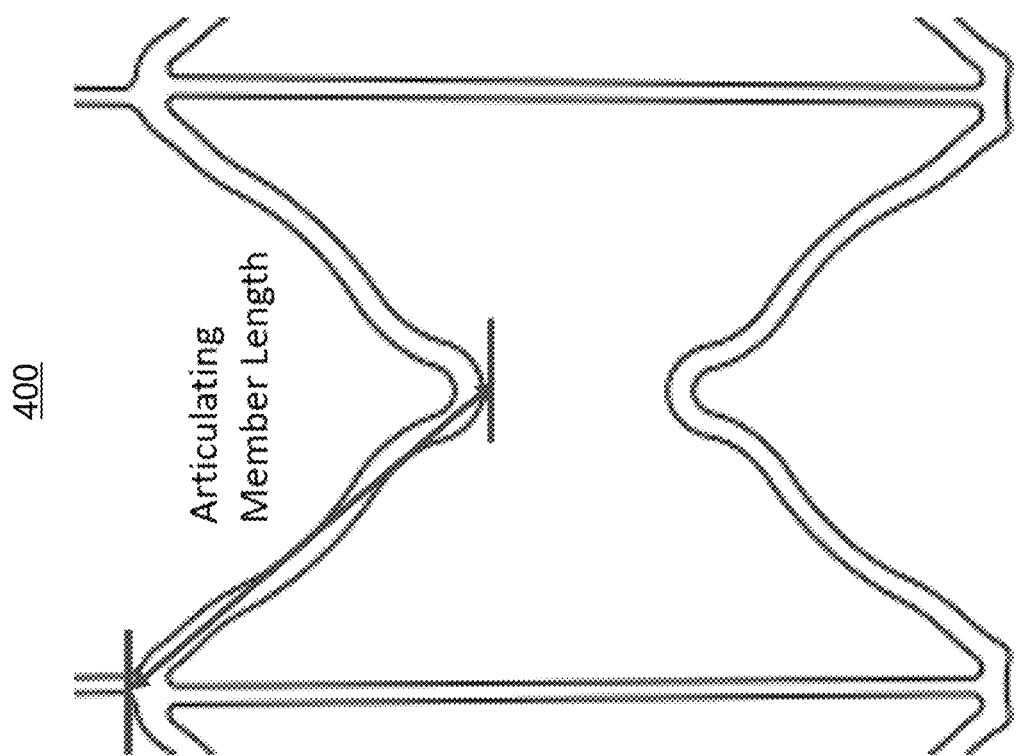

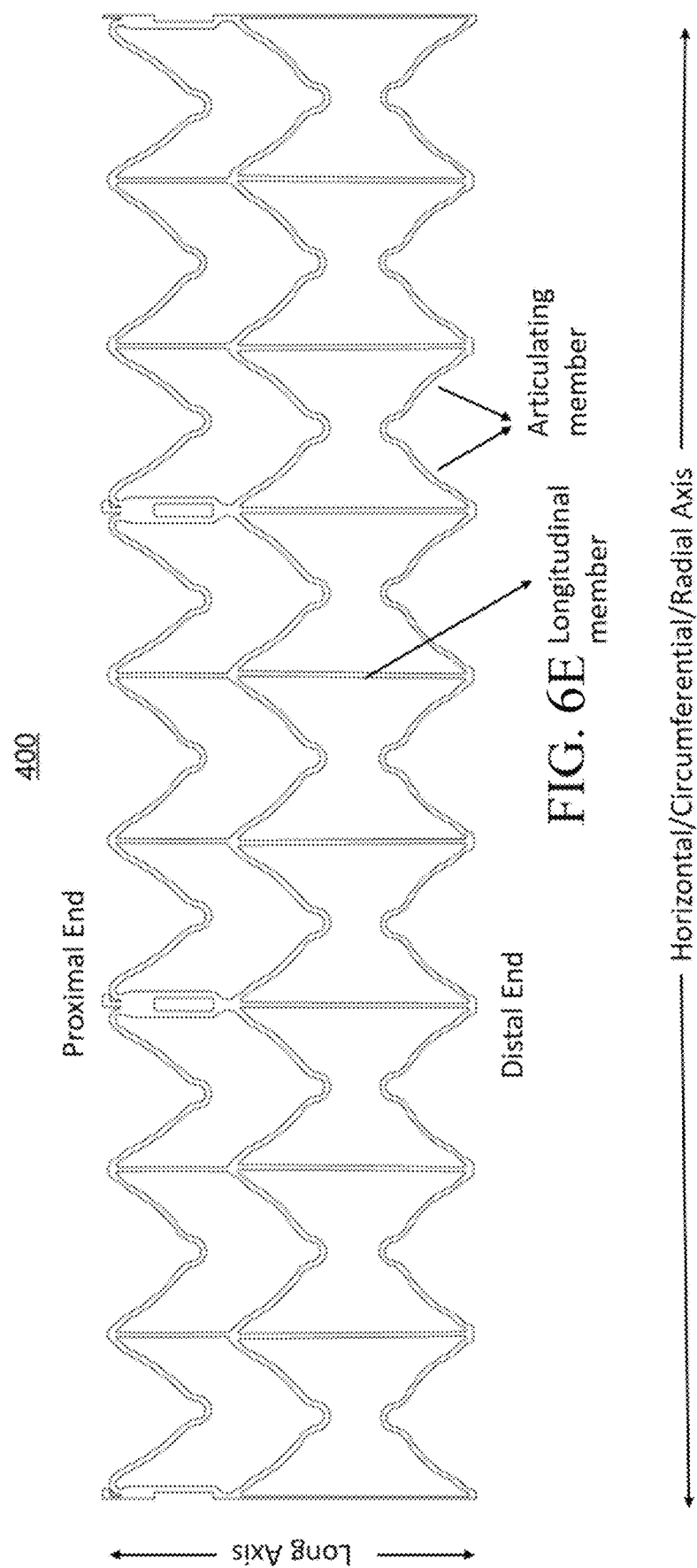

Table 1

| Material | Yield (ksi) | Modulus (ksi) |
|---|---|---|
| MoRe | 150 | 52900 |
| MP35N (annealed) | 55 | 33760 |
| MP35N (annealed) | 60 | 33800 |
| MP35N (annealed) | 60 | 33800 |
| L605 (annealed; not used for TAVR | 75 | N/A |
| L605 (annealed; not used for TAVR | 72 | 35200 |
| 316 SSL | 50 | 28000 |

FIG. 7

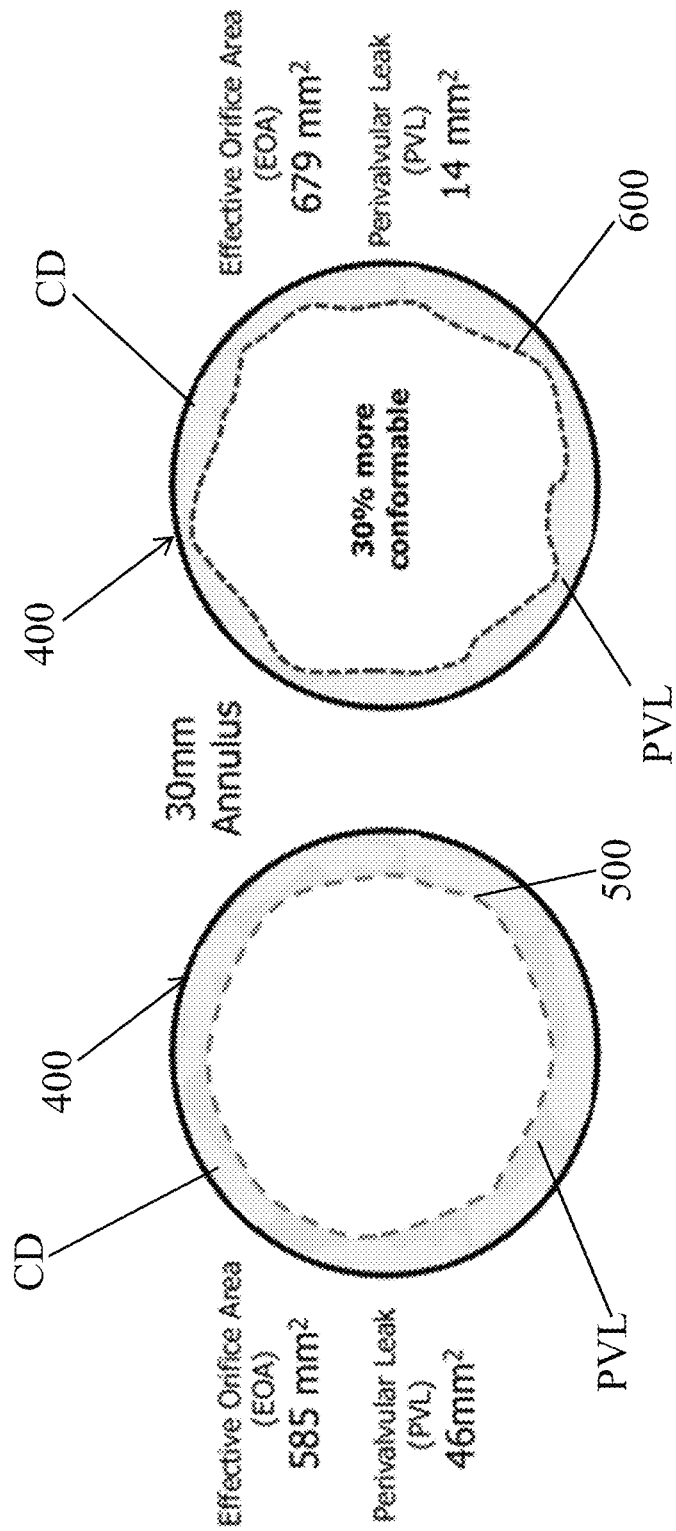

EXPANDABLE FRAME FOR MEDICAL DEVICE

REFERENCED APPLICATIONS

The present application claims priority to U.S. Provisional Application Ser. No. 63/540,556 filed Sep. 26, 2023, which is incorporated herein by reference.

The present disclosure is a continuation-in-part of U.S. application Ser. No. 18/417,939 filed Jan. 19, 2024, which in turn claims priority on United States Provisional Application Serial No. Ser. No. 63/439,892, filed Jan. 19, 2023, which are all fully incorporated herein by reference.

The present disclosure is a continuation-in-part of U.S. application Ser. No. 18/418,007 filed Jan. 19, 2024, which in turn claims priority on United States Provisional Application Serial No. Ser. No. 63/439,908, filed Jan. 19, 2023, which are all fully incorporated herein by reference.

The present application is a continuation-in-part of U.S. application Ser. No. 18/400,338 filed Dec. 29, 2023, which in turn priority claims priority to U.S. Provisional Application Ser. No. 63/540,266 filed Sep. 25, 2023, which are all fully incorporated herein by reference.

The present application is a continuation-in-part of U.S. application Ser. No. 18/204,180 filed May 31, 2023, which claims priority on U.S. Provisional Application Ser. No. 63/389,281 filed Jul. 14, 2022, which are all fully incorporated herein by reference.

The present application is a continuation-in-part of U.S. application Ser. No. 18/204,180 filed May 31, 2023, which claims priority on U.S. Provisional Application Ser. No. 63/347,337 filed May 31, 2022, which are all fully incorporated herein by reference.

FIELD OF DISCLOSURE

The disclosure relates generally to medical devices and medical device applications, and particularly to a medical device that includes an expandable frame, more particularly to a medical device in the form of a cardiovascular implant for the treatment of structural heart disease wherein the cardiovascular implant includes an expandable frame, and still more particularly to a medical device in the form of a prosthetic heart valve for the treatment of structural heart disease wherein the prosthetic heart valve includes an expandable frame.

BACKGROUND OF DISCLOSURE

Many cardiovascular devices such as expandable heart valves, and the like are inserted into a patient via the vascular system of a patient and then expanded at the treatment site. These devices are typically crimped onto a catheter prior to insertion into a patient.

Medical devices such as Transcatheter aortic valves (TAVs) represent a significant advancement in prosthetic heart valve technology. TAVs bring the benefit of heart valve replacement to patients that would otherwise not be operated on. Transcatheter aortic valve replacement (TAVR) can be used to treat aortic valve stenosis in patients who are classified as high-risk for open heart surgical aortic valve replacement (SAVR). Non-limiting TAVs are disclosed in U.S. Pat. Nos. 5,411,522; 6,730,118; 10,729,543; 10,820,993; 10,856,970; 10,869,761; 10,952,852; 10,980,632; 10,980,633; and US Pub. No. 2020/0405482, all of which are incorporated fully herein by reference. The frame material used to form the TAV is typically TiAlV alloy, CoCr alloy or Nitinol™. The vast majority of cardiovascular implants include valves that are made at least in part by using a CoCr alloy or Nitinol materials for construction of the structural frame of the valve.

A TAV is designed to be compressed into a small diameter catheter, remotely placed within a patient's diseased aortic valve to take over the function of the native valve. Some TAVs are balloon-expandable, while others are self-expandable. In both cases, the TAVs are deployed within a calcified native valve that is forced permanently open and becomes the surface against which the frame is held in place by friction. TAVs can also be used to replace failing bioprosthetic or transcatheter valves, commonly known as a valve in valve procedure. Major TAVR advantages to the traditional surgical approaches include refraining from cardiopulmonary bypass, aortic cross-clamping and sternotomy which significantly reduces patients' morbidity.

However, several complications are associated with current TAV devices such as serious vascular injury or bleeding due to the large delivery profiles, mispositioning, crimp-induced leaflet damage, paravalvular leak, thrombosis, conduction system abnormalities and prosthesis-patient mismatch.

TAVR involves delivery, deployment, and implantation of a crimped, framed valve within a diseased aortic valve or degenerated bioprosthesis. Some limitation of the current procedure for TAVR include a) vascular complications such as dissection or severe bleeding due to the large size of the delivery system, b) recoil associated with the valve frame as defined as the frame being opened to a certain positional diameter and then relaxing or settling to a smaller diameter post balloon deflation which can lead to valve embolization, paravalvular leak, reduced effective orifice area (EOA), c) high incidence of conduction system injury leading to permanent pacemaker implantation or sudden cardiac death; the conduction abnormalities are worsened by the frame recoil which necessitates that the operator reach a higher balloon inflation diameter to obtain a physiologic effective orifice area after balloon deflation, d) longitudinal foreshortening of the frame during balloon expansion of the frame which can lead to mispositioning of the valve in the aortic annulus, e) imprecise alignment of the TAVR frame commissures with the native commissures which adversely affects hemodynamic performance and prosthetic valve durability, f) non-uniform valve frame expansion which leads to a non-cylindrical prosthetic valve which leads to increased acute and chronic complications such as leaflet thrombosis and structural valve deterioration, and g) high nickel content which is a common allergen.

Current structural heart valve procedures are limited by the combination of material and geometry of the prosthetic heart valve frame. The deficiencies include a) vascular complications such as dissection or severe bleeding due to the large size of the delivery system, b) neurological complications such as stroke due to the large size of the delivery system passing through calcified anatomy, c) adequate radial strength to restore physiological EOA in a diseased valve, while maintaining a crimp diameter for vascular access, d) recoil associated with the valve frame as defined as the frame being opened to a certain positional diameter and then relaxing or settling to a smaller diameter post balloon deflation which can lead to valve embolization, paravalvular leak, reduced effective orifice area (EOA), c) high incidence of conduction system injury leading to permanent pacemaker implantation or sudden cardiac death; the conduction abnormalities are worsened by the frame recoil which necessitates that the operator reach a higher balloon inflation diameter to obtain a physiologic effective orifice area after balloon deflation, f) foreshortening of the frame during balloon expansion of the frame which can lead to mispositioning of the valve in the aortic annulus, g) imprecise alignment of the prosthetic heart calve frame commissures with the native commissures which adversely affects hemodynamic performance, coronary blood flow, and prosthetic valve durability, h) acute coronary obstruction and coronary access impairment for re-intervention due to frame height, commissural misalignment, and malalignment of open cell geometry at the location of the coronaries, i) difficulties in later intervention of valve in valve due to valve height and/or misalignment of the prosthetic heart valve frame commissures with the native commissures, and putting patient at risk for coronary obstruction and coronary access impairment and overlap of open cells; cell size, etc., j) non-uniform valve frame expansion which leads to a non-cylindrical prosthetic valve which leads to increased acute and chronic complications such as leaflet thrombosis and structural valve deterioration, and k) high nickel content which is a common allergen.

In view of the current state of the art of prosthetic heart valves, there is a need for an improved prosthetic heart valve that addresses the above deficiencies.

SUMMARY OF THE DISCLOSURE

The present disclosure is directed to a medical devices and medical device applications. The medical device can include, but is not limited to, a PFO (patent foramen ovale) device; stent (e.g., stent for used in aortic, iliac, subclavian, carotid, femoral artery, tibial, intracranial arteries, etc.); aneurysm exclusion devices (e.g., devices for aneurysm for use in aorta, iliac, intracranial arteries, etc.); valve (e.g., heart valve, TAVR valve, aortic, mitral valve replacement, tricuspid valve replacement, pulmonary valve replacement, etc.); anchoring devices for valves (e.g., anchoring devices for heart valve, TAVR valve, aortic valve, mitral valve, tricuspid valve, pulmonary valve, etc.); valve frames; occluders (e.g., occluders for patent foramen ovale, ventricular septal defect, left atrial appendage, etc.); guide wire; vascular implant; graft; guide wire; sheath, expandable sheath; catheter; needle; stent catheter; electrophysiology catheter; hypotube; staple; cutting device; pacemaker; dental implant; dental crown; dental braces; wire used in medical procedures; spinal implant; spinal discs; frame and other structure for use with a spinal implant; bone implant; artificial disk; artificial spinal disk; spinal interbody; expandable spinal interbody; interbody fusion device; expandable interbody fusion device; prosthetic implant or device to repair, replace and/or support a bone (e.g., acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, zygomatic bone, etc.) and/or cartilage; sutures; surgical staples; bone plate; knee replacement; hip replacement; shoulder replacement; ankle replacement; nail; rod; screw; post; cage; expandable cage; expandable orthopedic insert; plate (e.g., bone plate, cervical plate, spinal plate, etc.); bone plate nail; spinal rod; bone screw; post; spinal cage; pedicle screw; cap; hinge; joint system; screw extension; tulip extension; tether; graft; anchor; spacer; shaft; disk; ball; tension band; locking connector or other structural assembly that is used in a body to support a structure, mount a structure, and/or repair a structure in a body such as, but not limited to, a human body, animal body, etc. In one non-limiting embodiment, the medical device includes an expandable frame, more particularly the medical device is in the form of a cardiovascular implant for the treatment of structural heart disease wherein the cardiovascular implant includes an expandable frame, and still more particularly to a medical device is in the form of a prosthetic heart valve for the for the treatment of structural heart disease wherein the prosthetic heart valve includes an expandable frame that is formed of a rhenium containing metal alloy. Although the medical device will be particularly discussed with reference to a prosthetic heart valve, it will be appreciated by one skilled in the art that several of the features discussed herein such as to, but limited to, alloy composition, coatings on one or more portions of the medical device, alloy processing methods, processing methods to form all or a portion of the medical device, etc. can be used with other types of medical devices. The use of a rhenium containing metal alloy to partially or fully form the frame of the prosthetic heart valve allows for a novel structural prosthetic heart valve frame geometry. The combination of the rhenium containing metal alloy and the novel geometry of the frame of the prosthetic heart valve addresses the current deficiencies of prosthetic heart valves that are discussed above. The novel geometry of the frame of the prosthetic heart valve in combination with the frame being partially (e.g., 10-99.99 wt. % and all values and ranges therebetween) or fully formed of the rhenium containing alloy enable the formation of a frame that a) has an open cell geometry that can be used to reduce delivery system size thereby reducing vascular and neurological complications, b) has an open cell pattern that has high radial strength due to the high yield strength and ultimate tensile strength of the rhenium containing metal alloy, c) has improved restoration of the physiologic EOA in challenging, heavily calcified valves that exert high force on the bioprosthetic valve, while also allowing a reduced crimp diameter for vascular access, d) has improved restoration of the physiologic EOA that results in greater longevity of the bioprosthetic valve, c) has lower recoil than traditional materials used to form frames such as stainless steel, chromium-cobalt, or titanium alloys, thereby resulting in less recoil of the frame when expanded which leads to decreased risk of valve embolization, decreased paravalvular leak due to improved conformability of the native anatomy, more accurate restoration of the physiologic EOA, and decrease conduction system injury due to a lower balloon inflation diameter required to obtain the physiologic EOA after balloon inflation, f) has an open cell geometry that is configured to have little (e.g., 0-20% longitudinal foreshortening along a longitudinal axis of the expandable frame and all values and ranges therebetween) or no foreshortening when expanded, which allows for more accurate placement of the valve in the native annulus, and wherein a frame that has little or no longitudinal foreshortening when expanded can be expanded with a shorter balloon, which use of a shorter balloon for frame expansion can decrease conduction system injury, g) has commissural alignment markers and an open cell between the commissures that allows for proper placement of the bioprosthetic valve in relation to the native commissures of the valve for proper hemodynamic function in regard to wash out of the valve and blood flow to the coronaries, which leads to better durability and longevity of the valve, and access and re-intervention of the coronaries preventing future adverse events, h) has an open cell geometry with radial symmetry, longitudinal symmetry, and little or no longitudinal foreshortening which allows for symmetrical and cylindrical expansion of the prosthetic valve resulting in lower rates of leaflet thrombosis and structural valve deterioration, and i) is formed of a rhenium containing metal alloy with no nickel content that prevents allergic response due to the presence of nickel and restenosis associated with nickel content.

In one non-limiting aspect of the disclosure, the prosthetic heart valve (e.g., heart valve, TAVR valve, mitral valve replacement, tricuspid valve replacement, pulmonary valve replacement, etc.) includes a radially collapsible and expandable frame and a leaflet structure that comprises a plurality of leaflets. In another non-limiting embodiment, the prosthetic heart valve optionally includes an annular skirt or cover member that is disposed on and partially or fully covering or overlaid over the cells of at least a portion of the frame. In another non-limiting embodiment, the frame of the prosthetic heart valve comprises a plurality of interconnected axial longitudinal member, angular articulating members and strut joints that define a plurality of open cells in the frame.

In another and/or alternative non-limiting aspect of the disclosure, the frame of the prosthetic heart valve is optionally partially or fully formed of a) a refractory metal alloy and/or b) a metal alloy that includes at least 15 atomic weight percent (awt. %) or atomic percent (awt. %) rhenium so as to create a "rhenium effect" in the metal alloy. As used herein, atomic weight percent (awt. %) or atomic percentage (awt. %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents. It has been found that for several metal alloys the inclusion of at least 15 awt. % rhenium results in the ductility and/or tensile strength of the metal alloy to improve as compared to a metal alloy is that absent rhenium. Such improvement in ductility and/or tensile strength due to the inclusion of at least 15 awt. % rhenium in the metal alloy is referred to as the "rhenium effect." As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc. In one non-limiting arrangement, 50-100 wt. % (and all values and ranges therebetween) of the expandable frame of the prosthetic heart valve is formed of a refractory metal alloy or a metal alloy that includes at least 15 awt. % rhenium. In another non-limiting arrangement, the metal alloy that is used to partially or fully form the expandable frame of the prosthetic heart valve includes at least 30 wt. % (e.g., 30-99 wt. % and all values and ranges therebetween) of one or more of molybdenum, rhenium, niobium, tantalum or tungsten. In another non-limiting embodiment, the refractory metal alloy or the metal alloy that includes at least 15 awt. % rhenium can be used to 1) increase the radiopacity of the frame of the prosthetic heart valve, 2) increase the radial strength of the frame of the prosthetic heart valve, 3) increase the yield strength and/or ultimate tensile strength of the frame of the prosthetic heart valve, 4) improve the stress-strain properties of the frame of the prosthetic heart valve, 5) improve the crimping and/or expansion properties of the frame of the prosthetic heart valve, 6) improve the bendability and/or flexibility of the frame of the prosthetic heart valve, 7) improve the strength and/or durability of the frame of the prosthetic heart valve, 8) increase the hardness of the frame of the prosthetic heart valve, 9) improve the biostability and/or biocompatibility properties of the frame of the prosthetic heart valve, 10) increase fatigue resistance of the frame of the prosthetic heart valve, 11) resist cracking in the frame of the prosthetic heart valve, 12) resist propagation of cracks in the frame of the prosthetic heart valve, 13) enable smaller, thinner, and/or lighter weight frames of the prosthetic heart valve to be made, 14) facilitate in the reduction of the outer diameter of a crimped prosthetic heart valve, 15) improve the conformity of the frame of the prosthetic heart valve to the shape of the treatment area when the prosthetic heart valve is expanded in the treatment area, 16) reduce the amount of recoil of the frame of the prosthetic heart valve after the frame is expanded in the treatment area, 17) reduce adverse tissue reactions with the frame of the prosthetic heart valve, 18) reduce metal ion release from the frame after implantation of the prosthetic heart valve, 19) reduce corrosion of the frame of the prosthetic heart valve after implantation of the prosthetic heart valve, 20) reduce allergic reaction with the frame of the prosthetic heart valve after implantation of the prosthetic heart valve (e.g., reduce nickel content of metal alloy, etc.), 21) improve hydrophilicity of the frame of the prosthetic heart valve, 22) reduce magnetic susceptibility of the frame of the prosthetic heart valve, 23) reduced longitudinal foreshortening the frame of the prosthetic heart valve when the frame of the prosthetic heart valve is expanded, and/or 24) reduce toxicity of the frame of the prosthetic heart valve after implantation of the prosthetic heart valve.

In another and/or alternative non-limiting aspect of the disclosure, the frame of the prosthetic heart valve is optionally partially (e.g. 1-99.999 wt. % and all values and ranges therebetween) or fully formed of a metal material that includes a) stainless steel, b) CoCr alloy, c) TiAlV alloy, d) aluminum alloy, c) nickel alloy, f) titanium alloy, g) tungsten alloy, h) molybdenum alloy, i) copper alloy, j) beryllium-copper alloy, k) titanium-nickel alloy, 1) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 atomic weight percent (awt. %) or atomic percent (awt. %) rhenium (e.g., 5-99 awt. % rhenium and all values and ranges therebetween). As defined herein, a stainless-steel alloy (SS alloy) includes at least 50 wt. % (weight percent) iron, 10-28 wt. % chromium, 0-35 wt. % nickel, and optionally one or more of 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Sc, 0-2 wt. % vanadium, and 0-2 wt. % tungsten. A 316L alloy that falls within a stainless-steel alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 30-68 wt. % cobalt, 15-32 wt. % chromium, and optionally one or more of 1-38 wt. % nickel, 2-18 wt. % molybdenum, 0-18 wt. % iron, 0-1 wt. % titanium, 0-0.15 wt. % manganese, 0-0.15 wt. % silver, 0-0.25 wt. % carbon, 0-16 wt. % tungsten, 0-2 wt. % silicon, 0-2 wt. % aluminum, 0-1 wt. % iron, 0-0.1 wt. % boron, 0-0.15 wt. % silver, and 0-2 wt. % titanium. As a MP35N alloy that falls within a CoCr alloy includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. As defined herein, a Phynox and Elgiloy alloy that falls within a CoCr alloy includes 38-42 wt. % cobalt, 18-22 wt. % chromium, 14-18 wt. % iron, 13-17 wt. % nickel, 6-8 wt. % molybdenum. As defined herein, a L605 alloy that falls within a CoCr alloy includes 18-22 wt. % chromium, 14-16 wt. % tungsten, 9-11 wt. % nickel, balance cobalt. As defined herein, a titanium-aluminum-vanadium alloy (TiAlV alloy) includes 4-8 wt. % aluminum, 3-6 wt. % vanadium, 80-93 wt. % titanium, and optionally one or more of 0-0.4 wt. % iron, 0-0.2 wt. % carbon, 0-0.5 wt. % yttrium. A Ti-6Al-4V alloy that falls with a TiAlV alloy includes incudes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, and optionally one or more 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, and optionally one or more 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, and optionally one of more of 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, and optionally one or more of 0-8 wt. % nickel, 0-5 wt. % copper, 0-5 wt. % molybdenum, 0-4 wt. % iron. As defined herein, a molybdenum alloy includes 90-99.5 wt. % molybdenum, and optionally one or more of 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, and optionally one or more of 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, and optionally one or more of 0-1 wt. % cobalt, and 0-0.5 wt. % silicon. As defined herein, a titanium-nickel alloy (e.g., Nitinol alloy) includes 42-58 wt. % nickel and 42-58 wt. % titanium.

In accordance with another and/or alternative aspect of the present disclosure, the metal alloy that is used to partially or fully form the frame of the prosthetic heart valve includes at least 5 awt. % (e.g., 5-99 awt. % and all values and ranges therebetween) rhenium, and 0.1-96 wt. % (and all values and ranges therebetween) of one or more additives selected from the group of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other components other than the additives (e.g., carbon, oxygen, phosphorous, sulfur, hydrogen, lead, nitrogen, etc.), and which metal alloy exhibits a rhenium effect. In one non-limiting embodiment, the metal alloy that is used to partially or fully form the frame of the prosthetic heart valve is a stainless-steel alloy that has been modified to include at least 15 awt. % rhenium. In another non-limiting embodiment, the metal alloy that is used to partially or fully form the frame of the prosthetic heart valve is a cobalt chromium alloy that has been modified to include at least 15 awt. % rhenium. In another non-limiting embodiment, the metal alloy that is used to partially or fully form the frame of the prosthetic heart valve is a TiAlV alloy that has been modified to include at least 15 awt. % rhenium. In another non-limiting embodiment, the metal alloy that is used to partially or fully form the frame of the prosthetic heart valve is an aluminum alloy that has been modified to include at least 15 awt. % rhenium. In another non-limiting embodiment, the metal alloy that is used to partially or fully form the frame of the prosthetic heart valve is a nickel alloy that has been modified to include at least 15 awt. % rhenium. In another non-limiting embodiment, the metal alloy that is used to partially or fully form the frame of the prosthetic heart valve is a titanium alloy that has been modified to include at least 15 awt. % rhenium. In another non-limiting embodiment, the metal alloy that is used to partially or fully form the frame of the prosthetic heart valve is a tungsten alloy that has been modified to include at least 15 awt. % rhenium. In another non-limiting embodiment, the metal alloy that is used to partially or fully form the frame of the prosthetic heart valve is a molybdenum alloy that has been modified to include at least 15 awt. % rhenium. In another non-limiting embodiment, the metal alloy that is used to partially or fully form the frame of the prosthetic heart valve is a copper alloy that has been modified to include at least 15 awt. % rhenium. In another non-limiting embodiment, the metal alloy that is used to partially or fully form the frame of the prosthetic heart valve is a beryllium-copper alloy that has been modified to include at least 15 awt. % rhenium.

In accordance with another and/or alternative aspect of the present disclosure, the metal alloy that is used to partially or fully form the frame of the prosthetic heart valve includes rhenium and molybdenum, and the weight percent of rhenium in the metal alloy is optionally greater than the weight percent of molybdenum in the metal alloy, and the weight percent of one or more additive (e.g., aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium) in the metal alloy is optionally greater that the weight percent of molybdenum in the metal alloy, and the metal alloy optionally includes 0-2 wt. % of a combination of other components other than the additives (e.g., carbon, oxygen, phosphorous, sulfur, hydrogen, lead, nitrogen, etc.). In one non-limiting embodiment, the metal alloy that is used to partially or fully form the frame of the prosthetic heart valve includes rhenium and molybdenum, and the weight percent of rhenium plus the combined weight percent of additives is greater than the weight percent of molybdenum, and the metal alloy optionally includes 0-2 wt. % of a combination of other components other than the additives (e.g., carbon, oxygen, phosphorous, sulfur, hydrogen, lead, nitrogen, etc.).

In accordance with another and/or alternative aspect of the present disclosure, the metal alloy that is used to partially or fully form the frame of the prosthetic heart valve includes rhenium and molybdenum, and the atomic weight percent of rhenium to the atomic weight percent of the combination of one or more of bismuth, niobium, tantalum, tungsten, titanium, vanadium, chromium, manganese, yttrium, zirconium, technetium, ruthenium, rhodium, hafnium, osmium, copper, and iridium is 0.4:1 to 2.5:1 (and all values and ranges therebetween).

In accordance with another and/or alternative aspect of the present disclosure, the metal alloy that is used to partially or fully form the frame of the prosthetic heart valve includes at least 5 awt. % (e.g., 5-99 awt. % and all values and ranges therebetween) rhenium plus at least two metals selected from the group of molybdenum, bismuth, chromium, iridium, niobium, tantalum, titanium, yttrium, and zirconium, and the content of the metal alloy that includes other elements and compounds is 0-0.1 wt. %. In another non-limiting embodiment, the metal alloy includes rhenium, molybdenum, and chromium. In another non-limiting embodiment, the metal alloy includes at least 35 wt. % (e.g., 35-75 wt. % and all values and ranges therebetween) rhenium, and the metal alloy also includes chromium. In one non-limiting embodiment, the metal alloy includes at least 35 wt. % rhenium and at least 25 wt. % (e.g., 25-49.9 wt. % and all values and ranges therebetween) of the metal alloy includes chromium, and optionally 0.1-40 wt. % (and all values and ranges therebetween) of the metal alloy includes one or more of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other metals, carbon, oxygen, phosphorous, sulfur, hydrogen and/or nitrogen. In another non-limiting embodiment, the metal alloy includes 15-50 awt. % rhenium (and all values and ranges therebetween) and 0.5-70 awt. % chromium (and all values and ranges therebetween). In another non-limiting embodiment, the metal alloy includes 15-50 awt. % rhenium (and all values and ranges therebetween) and 0.5-70 awt. % tantalum (and all values and ranges therebetween). In another non-limiting embodiment, the metal alloy includes 15-50 awt. % rhenium (and all values and ranges therebetween) and 0.5-70 awt. % niobium (and all values and ranges therebetween). In another non-limiting embodiment, the metal alloy includes 15-50 awt. % rhenium (and all values and ranges therebetween) and 0.5-70 awt. % titanium (and all values and ranges therebetween). In another non-limiting embodiment, the metal alloy includes 15-50 awt. % rhenium (and all values and ranges therebetween) and 0.5-70 awt. % zirconium (and all values and ranges therebetween). In another non-limiting embodiment, the metal alloy includes 15-50 awt. % rhenium (and all values and ranges therebetween) and 0.5-70 awt. % molybdenum (and all values and ranges therebetween). In another non-limiting embodiment, the metal alloy includes at least 15 awt. % rhenium, greater than 50 wt. % titanium (e.g., 51-80 wt. % and all values and ranges therebetween), 15-45 wt. % (and all values and ranges therebetween) niobium, 0-10 wt. % (and all values and ranges therebetween) zirconium, 0-15 wt. % (and all values and ranges therebetween) tantalum, and 0-8 wt. % molybdenum (and all values and ranges therebetween).

In accordance with another and/or alternative aspect of the present disclosure, the metal alloy that is used to partially or fully form the medical device is partially for fully formed of a refractory metal alloy, and wherein the refractory metal alloy includes at least 20 wt. % of one or more of niobium, tantalum or tungsten, and wherein the refractory metal alloy includes 0-30 wt. % molybdenum (and all values and ranges therebetween), and wherein the refractory metal alloy includes at least 5 awt. % rhenium (e.g., 5-80 awt. % rhenium and all values and ranges therebetween).

In accordance with another and/or alternative aspect of the present disclosure, the metal alloy that is used to partially or fully form the medical device is partially for fully formed of a metal alloy includes at least 5 awt. % rhenium (e.g., 5-99 awt. % rhenium and all values and ranges therebetween), and at least 0.1 wt. % of one or more additive metals selected from aluminum, bismuth, chromium, cobalt, copper, hafnium, iridium, iron, magnesium, manganese, nickel, niobium, osmium, rhodium, ruthenium, silicon, silver, tantalum, technetium, titanium, tungsten, vanadium, yttrium, and zirconium, and wherein the metal alloy includes 0-30 wt. % molybdenum (and all values and ranges therebetween), and wherein a combined weight percent of rhenium and the additive metals is 70-100 wt. % (and all values and ranges therebetween).

In accordance with another and/or alternative aspect of the present disclosure, the metal alloy that is used to partially or fully form the medical device is partially for fully formed of a metal alloy of stainless steel that has been modified with at least 5 awt. % rhenium (e.g., 5-50 awt. % rhenium and all values and ranges therebetween), and wherein a combined weight percent of iron, chromium, nickel, tantalum, niobium, copper, manganese, aluminum, titanium, selenium, vanadium, tungsten and rhenium is 70-100 wt. % (and all values and ranges therebetween).

In accordance with another and/or alternative aspect of the present disclosure, the metal alloy that is used to partially or fully form the medical device is partially for fully formed of a metal alloy of cobalt-chromium alloy that has been modified with at least 5 awt. % rhenium (e.g., 5-50 awt. % rhenium and all values and ranges therebetween), and wherein a combined weight percent of cobalt, chromium, nickel, iron, titanium, manganese, silver, tungsten, silicon, aluminum, iron, boron, silver, titanium, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium-aluminum-vanadium alloy that has been modified with at least 5 awt. % rhenium (e.g., 5-50 awt. % rhenium and all values and ranges therebetween), and wherein a combined weight percent of aluminum, vanadium, titanium, iron, yttrium and rhenium is 70-100 wt. % (and all values and ranges therebetween).

In accordance with another and/or alternative aspect of the present disclosure, the metal alloy that is used to partially or fully form the medical device is partially for fully formed of a metal alloy of aluminum alloy that has been modified with at least 5 awt. % rhenium (e.g., 5-50 awt. % rhenium and all values and ranges therebetween), and wherein a combined weight percent of aluminum, silicon, magnesium, manganese, scandium, beryllium, yttrium, cerium, chromium, iron, zinc, titanium, lithium, silver, calcium, zirconium, cadmium, bismuth, nickel, vanadium, gallium, copper, and rhenium is 70-100 wt. % (and all values and ranges therebetween).

In accordance with another and/or alternative aspect of the present disclosure, the metal alloy that is used to partially or fully form the medical device is partially for fully formed of a metal alloy of nickel alloy that has been modified with at least 5 awt. % rhenium (e.g., 5-50 awt. % rhenium and all values and ranges therebetween), and wherein a combined weight percent of nickel, chromium, iron, copper, cobalt, aluminum, tantalum, tungsten, titanium, niobium, silicon, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium alloy that has been modified with at least 5 awt. % rhenium (e.g., 5-50 awt. % rhenium and all values and ranges therebetween), and wherein a combined weight percent of titanium, aluminum, tin, palladium, vanadium, nickel, ruthenium, chromium, zirconium, niobium, silicon, cobalt, iron, and rhenium is 70-100 wt. % (and all values and ranges therebetween).

In accordance with another and/or alternative aspect of the present disclosure, the metal alloy that is used to partially or fully form the medical device is partially for fully formed of a metal alloy of tungsten alloy that has been modified with at least 5 awt. % rhenium (e.g., 5-50 awt. % rhenium and all values and ranges therebetween), and wherein a combined weight percent of tungsten, nickel, copper, iron, and rhenium is 70-100 wt. % (and all values and ranges therebetween).

In accordance with another and/or alternative aspect of the present disclosure, the metal alloy that is used to partially or fully form the medical device is partially for fully formed of a metal alloy of copper alloy that has been modified with at least 5 awt. % rhenium (e.g., 5-50 awt. % rhenium and all values and ranges therebetween), and wherein a combined weight percent of copper, zinc, tin, iron, silicon, manganese, aluminum, beryllium, cobalt, nickel, and rhenium is 70-100 wt. % (and all values and ranges therebetween).

In accordance with another and/or alternative aspect of the present disclosure, the metal alloy that is used to partially or fully form the medical device is partially for fully formed of a metal alloy of beryllium-copper alloy that has been modified with at least 5 awt. % rhenium (e.g., 5-50 awt. % rhenium and all values and ranges therebetween), and wherein a combined weight percent of copper, beryllium, cobalt, silicon, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium-nickel alloy that has been modified with at least 5 awt. % rhenium (e.g., 5-50 awt. % rhenium and all values and ranges therebetween), and wherein a combined weight percent of nickel, titanium, and rhenium is 70-100 wt. % (and all values and ranges therebetween).

Several non-limiting examples of metal alloys that can be used to partially or fully form the medical device are set forth below in weight percent:

| Component/Wt. % | Ex. 1 | Ex. 2 | Ex. 3 | Ex. 4 |
|---|---|---|---|---|
| Al | 0-35% | 0-30% | 0-25% | 0-10% |
| Bi | 0-20% | 0-20% | 0-20% | 0-20% |
| Cr | 0-60% | 0-35% | 0-30% | 0-25% |
| Co | 0-60% | 0-50% | 0-40% | 0-20% |
| Mo | 0-95% | 0-80% | 0-55% | 0-30% |
| Nb | 0-80% | 0-60% | 0-50% | 0-20% |
| Ni | 0-60% | 0-55% | 0-40% | 0-20% |
| Re | 0.1-70% | 4.5-70% | 5-70% | 5-70% |
| Ta | 0-80% | 0-50% | 0-40% | 0-25% |
| Ti | 0-60% | 0-55% | 0-40% | 0-20% |
| V | 0-20% | 0-15% | 0-10% | 0-10% |
| W | 0-80% | 0-70% | 0-50% | 0-20% |
| Y | 0-20% | 0-15% | 0-10% | 0-10% |
| Zr | 0-20% | 0-15% | 0-10% | 0-10% |

| Component/Wt. % | Ex. 5 | Ex. 6 | Ex. 7 | Ex. 8 |
|---|---|---|---|---|
| Ag | 0-20% | 0-20% | 0-20% | 0-20% |
| Al | 0-35% | 0-30% | 5-30% | 0-25% |
| Bi | 0-20% | 0-20% | 0-20% | 0-20% |
| Cr | 10-40% | 0-40% | 0-40% | 0-40% |
| Cu | 0-20% | 0-20% | 0-20% | 0-20% |
| Co | 10-60% | 0-60% | 0-60% | 0-60% |
| Fe | 0-80% | 30-80% | 0-80% | 0-70% |
| Hf | 0-20% | 0-20% | 0-20% | 0-20% |
| Ir | 0-20% | 0-20% | 0-20% | 0-20% |
| Mg | 0-20% | 0-20% | 0-20% | 0-20% |
| Mn | 0-20% | 0-40% | 0-20% | 0-20% |
| Mo | 0-60% | 0-60% | 0-80% | 0-70% |
| Nb | 0-60% | 0-60% | 0-65% | 20-60% |
| Ni | 0-60% | 5-55% | 0-52% | 0-50% |
| Os | 0-20% | 0-20% | 0-20% | 0-20% |
| Pt | 0-20% | 0-20% | 0-20% | 0-20% |
| Re | 4.5-98% | 4.5-90% | 4.5-80% | 4.5-70% |
| Rh | 0-20% | 0-20% | 0-20% | 0-20% |
| Si | 0-20% | 0-20% | 0-20% | 0-20% |
| Sn | 0-20% | 0-20% | 0-20% | 0-20% |

-continued

| | | | | |
|---|---|---|---|---|
| Ta | 0-60% | 0-60% | 5-65% | 0-60% |
| Tc | 0-20% | 0-20% | 0-20% | 0-20% |
| Ti | 0-60% | 0-55% | 0-53% | 0-50% |
| V | 0-20% | 0-20% | 2-20% | 0-20% |
| W | 0-60% | 0-60% | 0-80% | 0-70% |
| Y | 0-20% | 0-20% | 0-20% | 0-20% |
| Zr | 0-20% | 0-20% | 0-20% | 5-20% |

| Component/Wt. % | Ex. 9 | Ex. 10 | Ex. 11 | Ex. 12 |
|---|---|---|---|---|
| Ag | 0-5% | 0-5% | 0-5% | 0-5% |
| Al | 0-5% | 0-5% | 1-15% | 0-20% |
| Bi | 0-5% | 0-5% | 0-5% | 0-5% |
| Cr | 1-28% | 1-30% | 0-5% | 0-30% |
| Cu | 0-20% | 0-5% | 0-5% | 0-25% |
| Co | 0-5% | 1-60% | 0-5% | 0-60% |
| Fe | 10-80% | 0-25% | 0-5% | 0-80% |
| Hf | 0-5% | 0-5% | 0-5% | 0-5% |
| Ir | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-8% | 0-25% | 0-5% | 0-98% |
| Nb | 0-5% | 0-5% | 0-5% | 0-95% |
| Ni | 1-20% | 1-45% | 0-5% | 0-50% |
| Os | 0-5% | 0-5% | 0-5% | 0-5% |
| Pt | 0-5% | 0-5% | 0-5% | 0-5% |
| Re | 5-20% | 4.8-20% | 4.5-20% | 4.5-20% |
| Rh | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-98% |
| Tc | 0-5% | 0-5% | 0-5% | 0-5% |
| Ti | 0-5% | 0-5% | 40-93% | 0-93% |
| V | 0-5% | 0-5% | 1-10% | 0-20% |
| W | 0-5% | 0-20% | 0-5% | 0-98% |
| Y | 0-5% | 0-5% | 0-5% | 0-5% |
| Zr | 0-5% | 0-5% | 0-5% | 0-5% |

| Component/Wt. % | Ex. 13 | Ex. 14 | Ex. 15 | Ex. 16 |
|---|---|---|---|---|
| Mo | 30-80% | 35-80% | 30-70% | 35-65% |
| Hf | 0.8-1.4% | 0-2% | 0-2.5% | 0-2.5% |
| Re | 7-49% | 7-49% | 7-60% | 7.5-49% |
| Ta | 0-2% | 0-2% | 0-50% | 0-50% |
| W | 0-2% | 0-2% | 0-50% | 20-50% |

| Component/Wt. % | Ex. 17 | Ex. 18 | Ex. 10 | Ex. 20 |
|---|---|---|---|---|
| W | 20-93% | 60-92% | 20-75% | 5-98% |
| Re | 6-60% | 8-40% | 7.5-47.5% | 0-80% |
| Mo | 0-47.5% | <0.5% | 1-47.5% | 0-80% |

| Component/Wt. % | Ex. 21 | Ex. 22 | Ex. 23 | Ex. 24 |
|---|---|---|---|---|
| Re | 5-60% | 5-60% | 5-60% | 5-60% |
| Mo | 0-55% | 10-55% | 10-55% | 10-55% |
| Bi | 1-42 | 0-32 | 0-32 | 0-32 |
| Cr | 0-32 | 1-42 | 0-32 | 0-32 |
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |

| Component/Wt. % | Ex. 25 | Ex. 26 | Ex. 27 | Ex. 28 |
|---|---|---|---|---|
| Re | 5-60% | 5-60% | 5-60% | 5-60% |
| Mo | 15-55% | 15-55% | 15-55% | 15-55% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |

-continued

| Component/Wt. % | Ex. 29 | Ex. 30 | Ex. 31 | Ex. 32 |
|---|---|---|---|---|
| Re | 50-75% | 55-75% | 60-75% | 65-75% |
| Cr | 25-50% | 25-45% | 25-40% | 25-35% |
| Mo | 0-25% | 0-25% | 0-25% | 0-25% |
| Bi | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| Ag | 0-25% | 0-25% | 0-25% | 0-25% |
| Al | 0-25% | 0-25% | 0-25% | 0-22% |
| Co | 0-25% | 0-25% | 0-25% | 0-25% |
| Fe | 0-25% | 0-25% | 0-25% | 0-25% |
| Mg | 0-25% | 0-25% | 0-25% | 0-25% |
| Ni | 0-25% | 0-25% | 0-25% | 0-25% |
| Pt | 0-25% | 0-25% | 0-25% | 0-25% |
| Si | 0-25% | 0-25% | 0-25% | 0-25% |
| Sn | 0-25% | 0-25% | 0-25% | 0-25% |

| Component/Wt. % | Ex. 33 | Ex. 34 | Ex. 35 | Ex. 36 |
|---|---|---|---|---|
| Re | 50-75% | 55-72% | 60-70% | 62-70% |
| Cr | 24-49% | 27-44% | 29-39% | 29-37% |
| Mo | 1-15% | 1-10% | 1-8% | 1-5% |
| Bi | 0-15% | 0-10% | 0-8% | 0-5% |
| Ir | 0-15% | 0-10% | 0-8% | 0-5% |
| Nb | 0-15% | 0-10% | 0-8% | 0-5% |
| Ta | 0-15% | 0-10% | 0-8% | 0-5% |
| V | 0-15% | 0-10% | 0-8% | 0-5% |
| W | 0-15% | 0-10% | 0-8% | 0-5% |
| Mn | 0-15% | 0-10% | 0-8% | 0-5% |
| Tc | 0-15% | 0-10% | 0-8% | 0-5% |
| Ru | 0-15% | 0-10% | 0-8% | 0-5% |
| Rh | 0-15% | 0-10% | 0-8% | 0-5% |
| Hf | 0-15% | 0-10% | 0-8% | 0-5% |
| Os | 0-15% | 0-10% | 0-8% | 0-5% |
| Cu | 0-15% | 0-10% | 0-8% | 0-5% |
| Ir | 0-15% | 0-10% | 0-8% | 0-5% |
| Ti | 0-15% | 0-10% | 0-8% | 0-5% |
| Y | 0-15% | 0-10% | 0-8% | 0-5% |
| Zr | 0-15% | 0-10% | 0-8% | 0-5% |
| Ag | 0-15% | 0-10% | 0-8% | 0-5% |
| Al | 0-15% | 0-10% | 0-8% | 0-5% |
| Co | 0-15% | 0-10% | 0-8% | 0-5% |
| Fe | 0-15% | 0-10% | 0-8% | 0-5% |
| Mg | 0-15% | 0-10% | 0-8% | 0-5% |
| Ni | 0-15% | 0-10% | 0-8% | 0-5% |
| Pt | 0-15% | 0-10% | 0-8% | 0-5% |
| Si | 0-15% | 0-10% | 0-8% | 0-5% |
| Sn | 0-15% | 0-10% | 0-8% | 0-5% |

| Component/Wt. % | Ex. 37 | Ex. 38 | Ex. 39 | Ex. 40 |
|---|---|---|---|---|
| Mo | 40-95% | 40-95% | 40-95% | 40-95% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |
| Nb | ≤0.01% | ≤0.01% | ≤0.01% | ≤0.01% |
| Pt | ≤1% | ≤1% | ≤1% | ≤1% |
| Re | 5-49% | 5-49% | 5-49% | 5-49% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |

-continued

| | | | | |
|---|---|---|---|---|
| W | 0-50% | 0-50% | 0-50% | 0.5-50% |
| Zr | ≤1% | ≤1% | ≤1% | ≤1% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| Sn | 0-5% | 0-5% | 0-5% | 0-5% |

| Component/Wt. % | Ex. 41 | Ex. 42 | Ex. 43 |
|---|---|---|---|
| W | 20-95% | 60-95% | 20-80% |
| Re | 5-47.5% | 5-40% | 5-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| Zr | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 44 | Ex. 45 | Ex. 46 | Ex. 47 |
|---|---|---|---|---|
| W | 1-94.9% | 1-94.9% | 1-94.9% | 10-95% |
| Cu | 0.1-94% | 0.1-94% | 0.1-94% | 1-84% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |
| Mo | 0-5% | 0.1-3% | 0-2% | 0-3% |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 6-40% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| Zr | ≤1% | ≤1% | ≤1% | ≤1% |
| Ag | 0-5% | 0-5% | 0-5% | 0-5% |
| Al | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |

| Component/Wt. % | Ex. 48 | Ex. 49 | Ex. 50 |
|---|---|---|---|
| W | 20-96% | 25-92% | 30-88% |
| Cu | 2-74% | 2-68% | 5-62% |
| Co | ≤0.002% | ≤0.002% | ≤0.002% |
| Hf | 0-2.5% | 0-2.5% | 0-2.5% |
| Os | ≤1% | ≤1% | ≤1% |
| Mo | 0-3% | 0-2% | 0-1% |
| Nb | ≤0.01% | ≤0.01% | ≤0.01% |
| Pt | ≤1% | ≤1% | ≤1% |
| Re | 6-40% | 7-40% | 8-40% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| Ag | 0-5% | 0-5% | 0-5% |
| Al | 0-5% | 0-5% | 0-5% |
| Fe | 0-5% | 0-5% | 0-5% |

-continued

| | | | |
|---|---|---|---|
| Mg | 0-5% | 0-5% | 0-5% |
| Ni | 0-5% | 0-5% | 0-5% |
| Si | 0-5% | 0-5% | 0-5% |

| Component/Wt. % | Ex. 51 | Ex. 52 | Ex. 53 | Ex. 54 |
|---|---|---|---|---|
| W | 25-88% | 35-87% | 40-86% | 50-85% |
| Cu | 5-68% | 5-57% | 5-51% | 5-40% |
| Hf | 0.8-1.4% | 0-2.5% | 0-2.5% | 0-2.5% |
| Re | 0-40% | 0-40% | 0-40% | 0-40% |
| Ta | 0-50% | 0-50% | 0-50% | 0-50% |

| Component/Wt. % | Ex. 55 | Ex. 56 | Ex. 57 |
|---|---|---|---|
| Ti | 55-66% | 65-76% | 70-76% |
| Mo | 20-41% | 20-31% | 20-26% |
| Re | 4-20% | 4-20% | 4-20% |
| Yt | <0.5% | <0.5% | <0.5% |
| Nb | <0.5% | <0.5% | <0.5% |
| Co | <0.5% | <0.5% | <0.5% |
| Cr | <0.5% | <0.5% | <0.5% |
| Zr | <0.5% | <0.5% | <0.5% |

| Component/Wt. % | Ex. 58 | Ex. 59 | Ex. 60 |
|---|---|---|---|
| W | 20-95% | 60-93% | 20-80% |
| Re | 5-47.5% | 7-40% | 5-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | <0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| Zr | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 61 | Ex. 62 | Ex. 63 | Ex. 64 |
|---|---|---|---|---|
| Ag | 0-10% | 0-10% | 0-10% | 0-10% |
| Al | 0-10% | 0-10% | 0-10% | 2-10% |
| B | 0-10% | 0-10% | 0-10% | 0-10% |
| Bi | 0-10% | 0-10% | 0-10% | 0-10% |
| Cr | 2-30% | 10-30% | 0-20% | 0-20% |
| Cu | 0-10% | 0-10% | 0-10% | 0-10% |
| Co | 0-10% | 32-70% | 0-10% | 0-10% |
| Fe | 50-80% | 0-20% | 0-10% | 0-10% |
| Hf | 0-10% | 0-10% | 0-10% | 0-10% |
| Ir | 0-10% | 0-10% | 0-10% | 0-10% |
| La | 0-10% | 0-10% | 0-10% | 0-10% |
| Mg | 0-10% | 0-10% | 0-10% | 0-10% |
| Mn | 0-20% | 0-10% | 0-10% | 0-10% |
| Mo | 0-10% | 0-30% | 0-16% | 0-16% |
| Nb | 0-10% | 0-10% | 0-10% | 0-10% |
| Ni | 0.1-30% | 0.1-40% | 0-10% | 0-10% |
| Os | 0-10% | 0-10% | 0-10% | 0-10% |
| Pt | 0-10% | 0-10% | 0-10% | 0-10% |
| Re | 5-40% | 4.8-40% | 4.5-80% | 4.5-80% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-12% | 0-12% |
| Ta | 0-10% | 0-10% | 0-10% | 0-10% |
| Tc | 0-10% | 0-10% | 0-10% | 0-10% |
| Ti | 0-10% | 0-10% | 70-91.5% | 70-91.5% |
| V | 0-10% | 0-10% | 0-10% | 0.01-10% |

-continued

| Component/Wt. % | | | | |
|---|---|---|---|---|
| W | 0-10% | 0-20% | 0-10% | 0-10% |
| Y | 0-10% | 0-10% | 0-10% | 0-10% |
| Zr | 0-10% | 0-10% | 0-10% | 0-10% |

| Component/Wt. % | Ex. 65 | Ex. 66 | Ex. 67 | Ex. 68 |
|---|---|---|---|---|
| Ag | 0-10% | 0-10% | 0-10% | 0-10% |
| Al | 0-10% | 0-10% | 0-10% | 0-10% |
| B | 0-10% | 0-10% | 0-10% | 0-10% |
| Bi | 0-10% | 0-10% | 0-10% | 0-10% |
| Cr | 0-10% | 0-20% | 0-20% | 0-10% |
| Cu | 0-10% | 0-10% | 0-50% | 0-10% |
| Co | 0-10% | 0-10% | 0-10% | 0-10% |
| Fe | 0-10% | 0-10% | 0-10% | 0-10% |
| Hf | 0-10% | 0-10% | 0-10% | 0-10% |
| Ir | 0-10% | 0-10% | 0-10% | 0-12% |
| La | 0-10% | 0-10% | 0-10% | 0-10% |
| Mg | 0-10% | 0-10% | 0-10% | 0-10% |
| Mn | 0-10% | 0-10% | 0-10% | 0-10% |
| Mo | 0-55% | 40-93% | 0-50% | 0-20% |
| Nb | 0-10% | 0-10% | 0-10% | 40-85% |
| Ni | 0-45% | 0-10% | 0-10% | 0-10% |
| Os | 0-10% | 0-10% | 0-10% | 0-10% |
| Pt | 0-10% | 0-10% | 0-10% | 0-10% |
| Re | 14-40% | 7-40% | 7-40% | 7-40% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-10% | 0-10% |
| Ta | 35-84% | 0-50% | 0-50% | 0-35% |
| Tc | 0-10% | 0-10% | 0-10% | 0-10% |
| Ti | 0-10% | 0-10% | 0-10% | 0-10% |
| V | 0-10% | 0-10% | 0-10% | 0-10% |
| W | 0.1-25% | 0-50% | 14-10% | 0-15% |
| Y | 0-10% | 0-10% | 0-10% | 0-10% |
| Zr | 0-10% | 0-10% | 0-50% | 0-10% |

| Component/Wt. % | Ex. 69 | Ex. 70 | Ex. 71 | Ex. 72 |
|---|---|---|---|---|
| Ag | 0-10% | 0-10% | 0-5% | 0-5% |
| Al | 0-10% | 0-10% | 0-5% | 5-7% |
| B | 0-10% | 0-10% | 0-5% | 0-5% |
| Bi | 0-10% | 0-10% | 0-5% | 0-5% |
| Cr | 0-10% | 1-95% | 12-28% | 0-5% |
| Cu | 0-10% | 0-10% | 0-5% | 0-5% |
| Co | 0-10% | 0-10% | 36-68% | 0-5% |
| Fe | 0-10% | 0-10% | 0-18% | 0-5% |
| Hf | 0-10% | 0-10% | 0-5% | 0-5% |
| Ir | 0-10% | 0-10% | 0-5% | 0-5% |
| La | 0-10% | 0-10% | 0-5% | 0-5% |
| Mg | 0-10% | 0-10% | 0-5% | 0-5% |
| Mn | 0-10% | 0-10% | 0-5% | 0-5% |
| Mo | 0-10% | 0-20% | 0-12% | 0-5% |
| Nb | 0-10% | 0-10% | 0-5% | 0-5% |
| Ni | 30-58% | 0-10% | 9-36% | 0-5% |
| Os | 0-10% | 0-10% | 0-5% | 0-5% |
| Pt | 0-10% | 0-10% | 0-5% | 0-5% |
| Re | 5-40% | 5-40% | 4.8-40% | 4.5-40% |
| Rh | 0-10% | 0-10% | 0-5% | 0-5% |
| Se | 0-10% | 0-10% | 0-5% | 0-5% |
| Si | 0-10% | 0-10% | 0-5% | 0-5% |
| Sn | 0-10% | 0-10% | 0-5% | 0-5% |
| Ta | 0-10% | 0-10% | 0-5% | 0-5% |
| Tc | 0-10% | 0-10% | 0-5% | 0-5% |
| Ti | 30-58% | 0-40% | 0-5% | 70-91.5% |
| V | 0-10% | 0-10% | 0-5% | 3-6% |
| W | 0-10% | 0-10% | 0-16% | 0-5% |
| Y | 0-10% | 0-10% | 0-5% | 0-5% |
| Zr | 0-10% | 0-20% | 0-5% | 0-5% |

| Component/Wt. % | Ex. 73 | Ex. 74 | Ex. 75 | Ex. 76 |
|---|---|---|---|---|
| Ag | 0-8% | 0-8% | 0-8% | 0-8% |
| Al | 0-8% | 0-8% | 0-8% | 2-10% |
| B | 0-8% | 0-8% | 0-8% | 0-8% |
| Bi | 0-8% | 0-8% | 0-8% | 0-8% |
| Cr | 2-30% | 10-30% | 0-20% | 0-20% |
| Cu | 0-8% | 0-8% | 0-8% | 0-8% |
| Co | 0-8% | 32-70% | 0-8% | 0-8% |

-continued

| Component/Wt. % | | | | |
|---|---|---|---|---|
| Fe | 50-80% | 0-20% | 0-8% | 0-8% |
| Hf | 0-8% | 0-8% | 0-8% | 0-8% |
| Ir | 0-8% | 0-8% | 0-8% | 0-8% |
| La | 0-8% | 0-8% | 0-8% | 0-8% |
| Mg | 0-8% | 0-8% | 0-8% | 0-8% |
| Mn | 0-20% | 0-8% | 0-8% | 0-8% |
| Mo | 0-8% | 0-30% | 0-16% | 0-16% |
| Nb | 0-8% | 0-8% | 0-8% | 0-8% |
| Ni | 0.1-30% | 0.1-40% | 0-8% | 0-8% |
| Os | 0-8% | 0-8% | 0-8% | 0-8% |
| Pt | 0-8% | 0-8% | 0-8% | 0-8% |
| Re | 5-40% | 4.8-40% | 4.5-80% | 4.5-80% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-12% | 0-12% |
| Ta | 0-8% | 0-8% | 0-8% | 0-8% |
| Tc | 0-8% | 0-8% | 0-8% | 0-8% |
| Ti | 0-8% | 0-8% | 70-91.5% | 70-91.5% |
| V | 0-8% | 0-8% | 0-8% | 0.01-10% |
| W | 0-8% | 0-20% | 0-8% | 0-8% |
| Y | 0-8% | 0-8% | 0-8% | 0-8% |
| Zr | 0-8% | 0-8% | 0-8% | 0-8% |

| Component/Wt. % | Ex. 77 | Ex. 78 | Ex. 79 | Ex. 80 |
|---|---|---|---|---|
| Ag | 0-8% | 0-8% | 0-8% | 0-8% |
| Al | 0-8% | 0-8% | 0-8% | 0-8% |
| B | 0-8% | 0-8% | 0-8% | 0-8% |
| Bi | 0-8% | 0-8% | 0-8% | 0-8% |
| Cr | 0-8% | 0-20% | 0-20% | 0-8% |
| Cu | 0-8% | 0-8% | 0-50% | 0-8% |
| Co | 0-8% | 0-8% | 0-8% | 0-8% |
| Fe | 0-8% | 0-8% | 0-8% | 0-8% |
| Hf | 0-8% | 0-8% | 0-8% | 0-8% |
| Ir | 0-8% | 0-8% | 0-8% | 0-12% |
| La | 0-8% | 0-8% | 0-8% | 0-8% |
| Mg | 0-8% | 0-8% | 0-8% | 0-8% |
| Mn | 0-8% | 0-8% | 0-8% | 0-8% |
| Mo | 0-55% | 40-93% | 0-50% | 0-20% |
| Nb | 0-8% | 0-8% | 0-8% | 40-85% |
| Ni | 0-45% | 0-8% | 0-8% | 0-8% |
| Os | 0-8% | 0-8% | 0-8% | 0-8% |
| Pt | 0-8% | 0-8% | 0-8% | 0-8% |
| Re | 14-40% | 7-40% | 7-40% | 7-40% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-8% | 0-8% |
| Ta | 35-84% | 0-50% | 0-50% | 0-35% |
| Tc | 0-8% | 0-8% | 0-8% | 0-8% |
| Ti | 0-8% | 0-8% | 0-8% | 0-8% |
| V | 0-8% | 0-8% | 0-8% | 0-8% |
| W | 0.1-25% | 0-50% | 14-10% | 0-15% |
| Y | 0-8% | 0-8% | 0-8% | 0-8% |
| Zr | 0-8% | 0-8% | 0-50% | 0-8% |

| Component/Wt. % | Ex. 81 | Ex. 82 | Ex. 83 | Ex. 84 |
|---|---|---|---|---|
| Ag | 0-5% | 0-5% | 0-5% | 0-5% |
| Al | 0-5% | 0-5% | 0-5% | 5-7% |
| B | 0-5% | 0-5% | 0-5% | 0-5% |
| Bi | 0-5% | 0-5% | 0-5% | 0-5% |
| Cr | 0-5% | 1-95% | 12-28% | 0-5% |
| Cu | 0-5% | 0-5% | 0-5% | 0-5% |
| Co | 0-5% | 0-5% | 36-68% | 0-5% |
| Fe | 0-5% | 0-5% | 0-18% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-20% | 0-12% | 0-5% |
| Nb | 0-5% | 0-5% | 0-5% | 0-5% |
| Ni | 30-58% | 0-5% | 9-36% | 0-5% |
| Os | 0-5% | 0-5% | 0-5% | 0-5% |
| Pt | 0-5% | 0-5% | 0-5% | 0-5% |
| Re | 5-40% | 5-40% | 4.8-40% | 4.5-40% |
| Rh | 0-5% | 0-5% | 0-5% | 0-5% |

-continued

| | | | | |
|---|---|---|---|---|
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 30-58% | 0-40% | 0-5% | 70-91.5% |
| V | 0-5% | 0-5% | 0-5% | 3-6% |
| W | 0-5% | 0-5% | 0-16% | 0-5% |
| Y | 0-5% | 0-5% | 0-5% | 0-5% |
| Zr | 0-5% | 0-20% | 0-5% | 0-5% |

| Component/Wt. % | Ex. 85 | Ex. 86 | Ex. 87 | Ex. 88 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 1-15% | 2-10% | 3-8% | 0-5% |
| Nb | 0-5% | 0-5% | 0-5% | 20-45% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 1-15% |
| Tc | 0-5% | 0-5% | 0-5% | 0-5% |
| Ti | 51-70% | 51-70% | 55-70% | 51-70% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 20-40% | 22-38% | 27-33% | 1-15% |

| Component/Wt. % | Ex. 89 | Ex. 90 | Ex. 91 | Ex. 92 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 25-40% | 30-40% | 25-40% | 26-32% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 2-8% | 3-6% | 5-15% | 10-14% |
| Tc | 0-5% | 0-5% | 0-5% | 0-5% |
| Ti | 51-70% | 52-63% | 51-68% | 51-62% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-12% | 4-8% | 2-8% | 2-6% |

| Component/Wt. % | Ex. 93 | Ex. 94 | Ex. 95 | Ex. 96 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 5-35% | 10-30% | 15-25% |
| Cu | 0-5% | 0-5% | 0-5% | 0-5% |
| Co | 0-5% | 20-55% | 25-50% | 35-45% |
| Fe | 0-5% | 3-25% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 2-15% | 3-12% | 4-9% |
| Nb | 30-40% | 0-5% | 0-5% | 0-5% |
| Ni | 0-5% | 4-23% | 5-20% | 10-18% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 1-3% | 0-5% | 0-5% | 0-5% |
| Tc | 0-5% | 0-5% | 0-5% | 0-5% |
| Ti | 51-67% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-5% | 0-5% | 0-5% | 0-5% |

| Component/Wt. % | Ex. 97 | Ex. 98 | Ex. 99 | Ex. 100 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 30-65% | 40-60% | 45-55% | 0-5% |
| Nb | 0-5% | 0-5% | 0-5% | 55-99.75% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 30-56% | 40-60% | 45-55% | 0.25-45% |

| Component/Wt. % | Ex. 101 | Ex. 102 | Ex. 103 | Ex. 104 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |

-continued

| | | | | |
|---|---|---|---|---|
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 75-99.5% | 95-99.25% | 55-78.5% | 68-74.25% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 20-35% | 25-30% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 1-8% | 0-5% |
| Y | 0-5% | 0-5% | 0-5% | 0-5% |
| Zr | 0.5-25% | 0.75-5% | 0.5-5% | 0.75-3% |

| Element/Wt. % | Ex. 105 | Ex. 106 | Ex. 107 | Ex. 108 |
|---|---|---|---|---|
| Re | 30-75% | 40-75% | 45-75% | 45-70% |
| Cr | 25-70% | 25-65% | 25-55% | 30-55% |
| Mo | 0-25% | 0-25% | 1-25% | 2-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |

In Examples 1-108, it will be appreciated that all of the above ranges include any value between the range and any other range that is between the ranges set forth above. Any of the above values that include the ≤ symbol includes the range from 0 to the stated value and all values and ranges therebetween.

In another and/or alternative non-limiting aspect of the present disclosure, the metal alloy that is used to partially or fully formed the frame of the prosthetic heart valve includes less than about 5 wt. % (e.g., 0-4.999999 wt. % and all values and ranges therebetween) other metals and/or impurities, typically 0-1 wt. %, more typically 0-0.1 wt. %, even more typically 0-0.01 wt. %, and still even more typically 0-0.001 wt. %. A high purity level of the metal alloy can result in the formation of a more homogeneous alloy, which in turn can result in a more uniform density throughout the metal alloy, and also can result in the desired yield and ultimate tensile strengths of the metal alloy.

In accordance with another and/or alternative aspect of the present disclosure, the frame for a prosthetic heart valve is optionally subjected to one or more manufacturing processes. These manufacturing processes can include, but are not limited to, expansion, laser cutting, etching, crimping, annealing, drawing, pilgering, electroplating, electro-polishing, machining, plasma coating, 3D printed coatings, chemical vapor deposition, chemical polishing, cleaning, pickling, ion beam deposition or implantation, sputter coating, vacuum deposition, etc.

In accordance with another and/or alternative aspect of the present disclosure, the metal alloy optionally includes a certain amount of carbon and oxygen; however, this is not required. These two elements have been found to affect the forming properties and brittleness of the metal alloy. The controlled atomic ratio of carbon and oxygen of the metal alloy can also minimize the tendency of the metal alloy to form micro-cracks during the forming of the metal alloy into a frame for a prosthetic heart valve, and/or during the use and/or expansion of the frame for a prosthetic heart valve in a body. The carbon to oxygen atomic ratio can be as low as about 0.2:1 (e.g., 0.2:1 to 50:1 and all values and ranges therebetween). In one non-limiting formulation, the carbon to oxygen atomic ratio in the metal alloy is generally at least about 0.3:1. Typically the carbon content of the metal alloy is less than about 0.1 wt. % (e.g., 0-0.0999999 wt. % and all values and ranges therebetween), and more typically 0-0.01 wt. %. Carbon contents that are too large can adversely affect the physical properties of the metal alloy. Generally, the oxygen content is to be maintained at very low level. In one non-limiting formulation, the oxygen content is less than about 0.1 wt. % of the metal alloy (e.g., 0-0.0999999 wt. % and all values and ranges therebetween), and typically 0-0.01 wt. %.

In accordance with another and/or alternative aspect of the present disclosure, the metal alloy optionally includes a controlled amount of nitrogen; however, this is not required. Large amounts of nitrogen in the metal alloy can adversely affect the ductility of the metal alloy. This can in turn adversely affect the elongation properties of the metal alloy. In one non-limiting formulation, the metal alloy includes less than about 0.001 wt. % nitrogen (e.g., 0 wt. % to 0.0009999 wt. % and all values and ranges therebetween). It is believed that the nitrogen content should be less than the content of carbon or oxygen in the metal alloy. In one non-limiting formulation, the atomic ratio of carbon to nitrogen is at least about 1.5:1 (e.g., 1.5:1 to 400:1 and all values and ranges therebetween). In another non-limiting formulation, the atomic ratio of oxygen to nitrogen is at least about 1.2:1 (e.g., 1.2:1 to 150:1 and all value and ranges therebetween).

In accordance with another and/or alternative aspect of the present disclosure, the metal alloy that is used to form all or part of the frame for a prosthetic heart valve 1) is not clad, metal coated, metal sprayed, plated and/or formed (e.g., cold worked, hot worked, etc.) onto another metal, or 2) does not have another metal or metal alloy metal sprayed, coated, plated, clad and/or formed onto the metal alloy. It will be appreciated that in some applications, the metal alloy of the present disclosure may be clad, metal sprayed, coated, plated and/or formed onto another metal, or another metal or metal alloy may be plated, metal sprayed, coated, clad and/or formed onto the metal alloy when forming all or a portion of a frame for a prosthetic heart valve.

In accordance with another and/or alternative aspect of the present disclosure, the metal alloy can be used to form a) a coating (e.g., cladding, dip coating, spray coating, plated coating, welded coating, plasma coating, etc.) on a portion of all of a frame for a prosthetic heart valve, or b) a core of a portion or all of a frame for a prosthetic heart valve. The composition of the coating is different from the composition of the material surface to which the metal alloy is coated. The coating thickness of the metal alloy is non-limiting (e.g., 1 μm to 1 inch and all values and ranges therebetween). In one non-limiting example, there is provided a frame for a prosthetic heart valve wherein a core or base layer of the frame for a prosthetic heart valve is formed of a metal or metal alloy (e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.) or polymer or ceramic or composite material, and the other layer of the coated frame for a prosthetic heart valve is formed of a different metal or metal alloy. The core or base layer and the other layer of the frame for a prosthetic heart valve can each form 10-99% (and all values and ranges therebetween) of the overall cross section of the frame for a prosthetic heart valve. When the outer metal coating is a rhenium containing alloy, such rhenium alloy can be used to create a hard surface on the frame for a prosthetic heart valve at specific locations as well as all over the surface. In another non-limiting embodiment, the core or base layer of the frame for a prosthetic heart valve can be formed of a rhenium containing alloy and the coating layer includes one or more other materials (e.g., another type of metal or metal alloy [e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.), polymer coating, ceramic coating, composite material coating, etc.). Non-limiting benefits of using the rhenium containing alloy in the core or interior layer of the frame for a prosthetic heart valve can include reducing the size of the frame for a prosthetic heart valve, increasing the strength of the frame for a prosthetic heart valve, and/or maintaining or reducing the cost of the frame for a prosthetic heart valve. As can be appreciated, the use of the rhenium containing alloy can result in other or additional advantages. The core or base layer size and/or thickness of the metal alloy are non-limiting. In one non-limiting example, there is provided a frame for a prosthetic heart valve that is at least partially formed from layered materials wherein a top layer is formed of material that is different form one or more other layers and the rhenium containing alloy forms one of the layers below the top layer, and the top layer is formed of a metal that is different from the rhenium containing alloy (e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.). The core or lower layer or base layer and the outer layer of the layered material can each form 10-99% (and all values and ranges therebetween) of the overall cross section of the layered material.

In another and/or alternative non-limiting embodiment of the disclosure, the average tensile elongation of the metal alloy used to at least partially form the frame for a prosthetic heart valve is optionally at least about 20% (e.g., 20-50% average tensile elongation and all values and ranges therebetween). An average tensile elongation of at least 20% for the metal alloy is useful to facilitate in the frame for a prosthetic heart valve being properly expanded when positioned in the treatment area of a body. The desired tensile elongation can be obtained from a unique combination of the metals in the metal alloy in combination with achieving the desired purity and composition of the alloy and the desired grain size of the metal alloy.

In accordance with another and/or alternative aspect of the present disclosure, the metal alloy is optionally at least partially formed by a swaging process; however, this is not required. In one non-limiting embodiment, swaging is performed on the metal alloy to at least partially or fully achieve final dimensions of one or more portions of the frame for a prosthetic heart valve. The swaging dies can be shaped to fit the final dimension of the frame for a prosthetic heart valve; however, this is not required.

In accordance with another and/or alternative aspect of the present disclosure, the metal alloy can optionally be nitrided; however, this is not required. The nitrided layer on the metal alloy can function as a lubricating surface during the optional drawing of the metal alloy when partially or fully forming the frame for a prosthetic heart valve.

In accordance with another and/or alternative non-limiting aspect of the present disclosure, the frame for a prosthetic heart valve can optionally be partially (e.g., 1% to 99.99% and all values and ranges therebetween) or fully be coated with and/or include one or more agents. When one or more agents are coated on the prosthetic heart valve, and the prosthetic heart valve includes an enhancement layer, one or more agents are generally coated on the outer surface of the enhancement layer. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungus and/or bacterial infection; vascular diseases and/or disorders; lymphatic diseases and/or disorders; cancer; implant rejection; pain; nausea; swelling; organ failure; immunity diseases and/or disorders; cell growth inhibitors, blood diseases and/or disorders; heart diseases and/or disorders; neuralgia diseases and/or disorders; fatigue; genetic diseases and/or disorders; trauma; cramps; muscle spasms; tissue repair; nerve repair; neural regeneration and/or the like.

The type and/or amount of agent included coated on frame for a prosthetic heart valve can vary. In accordance with another and/or alternative aspect of the present disclosure, one or more portions of the frame for a prosthetic heart valve can optionally 1) include the same or different agents, 2) include the same or different amount of one or more agents, 3) include the same or different polymer coatings, 4) include the same or different coating thicknesses of one or more polymer coatings, 5) have one or more portions of the frame for a prosthetic heart valve controllably release and/or uncontrollably release one or more agents, and/or 6) have one or more portions of the frame for a prosthetic heart valve controllably release one or more agents and one or more portions of the frame for a prosthetic heart valve uncontrollably release one or more agents.

In accordance with another and/or alternative aspect of the present disclosure, one or more surfaces of the frame for a prosthetic heart valve can optionally be treated to achieve the desired coating properties of the one or more agents and/or one or more polymers coated on the frame for a prosthetic heart valve. Such surface treatment techniques include, but are not limited to, cleaning, buffing, smoothing, nitriding, annealing, swaging, cold working, etching (chemical etching, plasma etching, etc.), etc. As can be appreciated, other or additional surface treatment processes can be used prior to the coating of one or more agents and/or polymers on the surface of the frame for a prosthetic heart valve.

In another and/or alternative non-limiting aspect of the disclosure, the frame for a prosthetic heart valve can optionally include a marker material that facilitates enabling the frame for a prosthetic heart valve to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.).

In accordance with another and/or alternative aspect of the present disclosure, the frame for a prosthetic heart valve or one or more regions of the frame for a prosthetic heart valve can optionally be constructed by use of one or more microelectromechanical manufacturing (MEMS) techniques (e.g., micro-machining, laser micro-machining, micro-molding, etc.); however, other or additional manufacturing techniques can be used.

In accordance with another and/or alternative aspect of the present disclosure, the frame for a prosthetic heart valve can optionally include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

In accordance with another and/or alternative aspect of the present disclosure, the frame for a prosthetic heart valve can optionally include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the frame for a prosthetic heart valve. As defined herein, a "micro-structure" is a structure having at least one dimension (e.g., average width, average diameter, average height, average length, average depth, etc.) that is no more than about 2 mm, and typically no more than about 1 mm.

In another and/or alternative aspect of the disclosure, the frame for a prosthetic heart valve can optionally be an expandable device that can be expanded by use of some other device (e.g., balloon, etc.). The frame for a prosthetic heart valve can be fabricated from a material that has no or substantially no shape-memory characteristics.

In accordance with another and/or alternative aspect of the present disclosure, there is optionally provided a near net process for a frame of the frame for a prosthetic heart valve. In one non-limiting embodiment of the disclosure, there is provided a method of powder pressing materials and increasing the strength post-sintering by imparting additional cold work. In one non-limiting embodiment, the green part is pressed and then sintered. Thereafter, the sintered part is again pressed to increase its mechanical strength by imparting cold work into the pressed and sintered part.

In accordance with another and/or alternative aspect of the present disclosure, the metal alloy used to at least partially form the frame for a prosthetic heart valve can optionally be initially formed into a blank, a rod, a tube, etc., and then finished into final form by one or more finishing processes. The metal alloy blank, rod, tube, etc., can be formed by various techniques such as, but not limited to, 1) melting the metal alloy and/or metals that form the metal alloy (e.g., vacuum arc melting, etc.) and then extruding and/or casting the metal alloy into a blank, rod, tube, etc., 2) melting the metal alloy and/or metals that form the metal alloy, forming a metal strip, and then rolling and welding the strip into a blank, rod, tube, etc., 3) consolidating the metal powder of the metal alloy and/or metal powder of metals that form the metal alloy into a blank, rod, tube, etc., or 4) 3-D printing the metal powder of the metal alloy and/or metal powder of metals that form the metal alloy into a blank, rod, tube, etc. When the metal alloy is formed into a blank, the shape and size of the blank is non-limiting.

In accordance with another and/or alternative aspect of the present disclosure, when the metal powder is consolidated to form the metal alloy into a blank, rod, tube, etc., the metal powder is pressed together to form a solid solution of the metal alloy into a near net frame for a prosthetic heart valve, near net component of a frame for a prosthetic heart valve, blank, rod, tube, etc. Typically, the pressing process is by an isostatic process (i.e., uniform pressure applied from all sides on the metal powder); however other processes can be used. When the metal powders are pressed together isostatically, cold isostatic pressing (CIP) is typically used to consolidate the metal powders; however, this is not required. The pressing process can be performed in an inert atmosphere, an oxygen-reducing atmosphere (e.g., hydrogen, argon and hydrogen mixture, etc.), and/or under a vacuum; however, this is not required.

In accordance with another and/or alternative aspect of the present disclosure, when metal powder is used to 3D print a frame for a prosthetic heart valve, component of a frame for a prosthetic heart valve, blank, rod, tube, etc., the average particle size of the metal powder is optionally 2-62 microns, and more particularly about 5-49.9 microns, the average density of the metal powders is greater than 5 g/cm$^3$, and the metal powder is generally spherical-shaped, and the Hall flow (s/50 g) is less than 30 seconds (e.g., 2-29.99 seconds and all values and ranges therebetween).

In accordance with another and/or alternative non-limiting aspect of the present disclosure, the frame for a prosthetic heart valve can be partially (e.g., 1% to 99.99% and all values and ranges therebetween) or fully be coated with an enhancement layer to improve one or more properties of the frame for a prosthetic heart valve (e.g., change exterior color of material having coated surface, increase surface hardness by use of the coated surface, increase surface toughness material having coated surface, reduced friction via use of the coated surface, improve scratch resistance of material that has the coated surface, improve impact wear of coated surface, improve resistance to corrosion and oxidation of coated material, form a non-stick coated surface, improve biocompatibility of material having the coated surface, reduce toxicity of material having the coated surface, reduce ion release from material having the coated surface, the enhancement layer forms a surface that is less of an irritant to cell about the coated surface after the frame for a prosthetic heart valve is implanted, etc.). Non-limiting enhancement layers that can be applied to a portion or all of the frame for a prosthetic heart valve includes chromium nitride (CrN), diamond-like carbon (DLC), titanium nitride (TiN), titanium nitride oxide (TiNOx), zirconium nitride (ZrN), zirconium oxide ($ZrO_2$), zirconium-nitrogen-carbon (ZrNC), zirconium OxyCarbide (ZrOC), zirconium oxynitride (ZrNxOy) [e.g., cubic ZrN:O, cubic $ZrO_2$:N, tetragonal $ZrO_2$:N, and monoclinic $ZrO_2$:N phase coatings], and combinations of such coatings. In one non-limiting embodiment, the one or more enhancement layers are optionally applied to a portion or all of the frame for a prosthetic heart valve by a vacuum process using an energy source to vaporize material and deposit a thin layer of enhancement layer material. Such vacuum coating process, when used, can include a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. In one non-limiting embodiment, the coating process is one or more of a PVD, CVD, ALD and PE-CVD, and wherein the coating process occurs at a temperature of 200-400° C. (and all values and ranges therebetween) for at least 10 minutes (e.g., 10-400 minutes and all values and ranges therebetween). In another non-limiting embodiment, the coating process is one or more of a PVD, CVD, ALD and PE-CVD, and wherein the coating process occurs at a temperature of 220-300° C. for 60-120 minutes. In another non-limiting embodiment, when the materials of the one or more enhancement layers are to be applied to the outer surface of the frame for a prosthetic heart valve that is partially or fully formed of a metal alloy, the materials of the one or more enhancement layers can optionally be combine with one or more metals in the metal alloy, and/or combined with nitrogen, oxygen, carbon, or other elements that are in the metal alloy and/or present in the atmosphere about the metal alloy to a form an enhancement layer on the outer surface of the metal alloy. In another non-limiting embodiment, when the materials of the one or more enhancement layers are to be applied to the outer surface of the frame for a prosthetic heart valve that is partially or fully formed of a metal alloy, the materials of the one or more enhancement layers can optionally be used to form various coating colors on the outer surface of the metal alloy (e.g., gold, copper, brass, black, rose gold, chrome, blue, silver, yellow, green, etc.). In another non-limiting embodiment, the thickness of the enhancement layer is greater than 1 nanometer (e.g., 2 nanometers to 100 microns and all values and ranges therebetween), and typically 0.1-25 microns, and more typically 0.2-10 microns. In another non-limiting embodiment, the hardness of the enhancement layer can be at least 5 GPa (ASTM C1327-15 or ASTM C1624-05), typically 5-50 GPa (and all values and ranges therebetween), more typically 10-25 GPa, and still more typically 14-24 GPa. In another non-limiting embodiment, the coefficient of friction (COF) of the enhancement layer can be 0.04-0.2 (and all values and ranges therebetween), and typically 0.6-0.15. In another non-limiting embodiment, the wear rate of the enhancement layer can be $0.5\times10^{-7}$ $mm^3$/N-m to $3\times10^{-7}$ $mm^3$/N-m (an all values and ranges therebetween), and typically $1.2\times10^{-7}$ $mm^3$/N-m to $2\times10^{-7}$ $mm^3$/N-m. In another non-limiting embodiment, silicon-based precursors (e.g., trimethysilane, tetramethylsilane, hexachlorodisilane, silane, dichlorosilane, trichlorosilane, silicon tetrachloride, tris(dimethylamino) silane, bis(tert-butylamino)silane, trisilylamine, allyltrimethoxysilane, (3-aminopropyl)triethoxysilane, butyltrichlorosilane, n-sec-butyl(trimethylsilyl)amine, chloropentamethyldisilane, 1,2-dichlorotetramethyldisilane, [3-(diethylamino)propyl]trimethoxysilane, 1,3-diethyl-1,1,3,3-tctramethyldisilazane, dimethoxydimethylsilane, dodecamethylcyclohexasilane, hexamethyldisilane, isobutyl (trimethoxy)silane, methyltrichlorosilane, 2,4,6,8,10-pentamethylcyclopentasiloxane, pentamethyldisilane, n-propyltriethoxysilane, silicon tetrabromide, silicon tetrabromide, etc.) can optionally be used to facilitate in the application of the enhancement layer to one or more portions or all of the frame for a prosthetic heart valve. In one non-limiting embodiment, the enhancement layer includes no more than 0.1 wt. % nickel, no more than 0.1 wt. % chromium, and/or no more than 0.1 wt. % cobalt. In another non-limiting embodiment, the outer surface of the medical device includes no more than 0.1 wt. % nickel, no more than 0.1 wt. % chromium, and/or no more than 0.1 wt. % cobalt. The adhesion layer includes no more than 0.1 wt. % nickel, no more than 0.1 wt. % chromium, and/or no more than 0.1 wt. % cobalt. The enhancement layer and/or the metallic adhesion layer can be applied by use of a vacuum coating process (e.g., physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process), plating process, etc.

In accordance with another and/or alternative non-limiting aspect of the present disclosure, the frame for a prosthetic heart valve can be partially or fully coated with an enhancement layer composition that includes a chromium nitride (CrN) coating. A portion or all of the frame for a prosthetic heart valve can be partially or fully coated with the chromium nitride (CrN) coating. The enhancement layer can be used to improve hardness, improve toughness, reduced friction, resistant impact wear, improve resistance to corrosion and oxidation, and/or form a reduced stick surface when in contact with many different materials. In accordance with one non-limiting embodiment, the chromium nitride (CrN) coating generally includes 40-85 wt. % Cr (and all values and ranges therebetween), 15-60 wt. % N (and all values and ranges therebetween), 0-10 wt. % Re (and all values and ranges therebetween), 0-10 wt. % Si (and all values and ranges therebetween), 0-2 wt. % O (and all values and ranges therebetween), and 0-2 wt. % C (and all values and ranges therebetween). In one non-limiting coating process, all or a portion of the frame for a prosthetic heart valve are initially coated with Cr metal. The Cr metal coating can be applied by PVD, CVD, ALD and PE-CVD in an inert environment. The coating thickness of Cr metal is 0.5-15 microns. Thereafter, the Cr metal coating is exposed to nitrogen gas and/or a nitrogen containing gas compound to cause the nitrogen to react with the Cr metal coating to form a layer of CrN on the outer surface of the Cr metal coating and/or the outer surface of the frame for a prosthetic heart valve. Particles of Cr metal can optionally be mixed with nitrogen gas and/or a nitrogen containing gas compound to facilitate in the formation of the CrN coating. When Cr metal particles are used, the initial Cr coating layer on the frame for a prosthetic heart valve can optionally be eliminated. In another non-limiting embodiment, the enhancement layer composition generally includes 65-80 wt. % Cr, 15-30 wt. % N, 0-8 wt. % Re, 0-1 wt. % Si, 0-1 wt. % O, and 0-1 wt. % C.

In accordance with another and/or alternative non-limiting aspect of the present disclosure, the frame for a prosthetic heart valve can be partially or fully coated with an enhancement layer composition that includes a diamond-Like Carbon (DLC) coating. A portion or all of the frame for a prosthetic heart valve can be partially or fully coated with the diamond-Like Carbon (DLC) coating. The enhancement layer can be used to improve hardness, improve toughness, reduced friction, resistant impact wear, improve resistance to corrosion and oxidation, improve biocompatibility, and/or form a reduced stick surface when in contact with many different materials. In one non-limiting embodiment, the diamond-Like Carbon (DLC) coating generally includes 60-99.99 wt. % C (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % O (and all values and ranges therebetween). The carbon coating can be applied by PVD, CVD, ALD and PE-CVD in an inert environment. The carbon layer can be applied by use of methane and/or acetylene gas; however, other or additional carbon sources can be used. The coating thickness of the carbon is 0.5-15 microns. In another non-limiting embodiment, all or a portion of the frame for a prosthetic heart valve are coated with the enhancement layer composition that generally includes 90-99.99 wt. % C, 0-1 wt. % N, 0-8 wt. % Re, 0-1 wt. % Si, and 0-1 wt. % O.

In accordance with another and/or alternative non-limiting aspect of the present disclosure, the frame for a prosthetic heart valve can be partially or fully coated with an enhancement layer composition that includes a titanium nitride (TiN) coating. A portion or all of the outer surface of the frame for a prosthetic heart valve can include the titanium nitride (TIN) coating. The enhancement layer can be used to improve hardness, improve toughness, improve resistance to corrosion and oxidation, reduced friction, and/or form a reduced stick surface when in contact with many different materials. In one non-limiting embodiment, all or a portion of the outer surface of the frame for a prosthetic heart valve are optionally initially coated with Ti metal. The Ti metal coating, when applied, can be applied by PVD, CVD, ALD and PE-CVD in an inert environment. The coating thickness of Ti metal is 0.05-15 microns (and all values and ranges therebetween). As can be appreciated, the initial Ti coating is optional. Thereafter, the Ti metal coating, when applied, is exposed to nitrogen gas and/or a nitrogen containing gas compound and optionally titanium particles to cause the nitrogen to react with the Ti metal coating and/or titanium metal particles to form a layer of TiN on the outer surface of the Ti metal coating and/or the outer surface of the frame for a prosthetic heart valve. If a titanium layer is not preapplied, the TIN coating can be formed by exposing the frame for a prosthetic heart valve to titanium particles and nitrogen gas and/or a nitrogen containing gas compound. The coating thickness of the TiN coating is generally 0.1-15 microns (and all values and ranges therebetween), and typically 0.2-2 microns.

In accordance with another and/or alternative non-limiting aspect of the present disclosure, the frame for a prosthetic heart valve can be partially or fully coated with an enhancement layer composition that includes a titanium nitride oxide (TiNOx) coating. A portion or all of the outer surface of the frame for a prosthetic heart valve can include the titanium nitride oxide (TiNOx) coating. The enhancement layer can be used to improve hardness, improve toughness, improve resistance to corrosion and oxidation, reduced friction, and/or form a reduced stick surface when in contact with many different materials. In one non-limiting embodiment, all or a portion of the outer surface of the frame for a prosthetic heart valve are optionally initially coated with Ti metal. The Ti metal coating, when applied, can be applied by PVD, CVD, ALD and PE-CVD in an inert environment. The coating thickness of Ti metal is 0.05-15 microns (and all values and ranges therebetween). As can be appreciated, the initial Ti coating is optional. Thereafter, the Ti metal coating is exposed to titanium particles and a nitrogen and oxygen mixture that can include nitrogen gas, oxygen gas, a nitrogen containing gas compound and/or an oxygen containing gas compound to cause the nitrogen and oxygen to react with the Ti metal coating, if such coating is used, and/or with the Ti metal particles to form a layer of TiNOx on the outer surface of the Ti metal coating and/or the outer surface of the frame for a prosthetic heart valve. The ratio of the N to the O can be varied to control the amount of O in the TiNOx coating. If a titanium layer is not preapplied, the TiNOx coating can be formed by exposing the frame for a prosthetic heart valve to titanium particles and a nitrogen and oxygen source such as nitrogen gas, oxygen gas, a nitrogen containing gas compound and/or an oxygen containing gas compound. The ratio of N to O when forming the TiNOx coating is generally 1:10 to 10:1 (and all values and ranges therebetween). The coating thickness of the TiNOx coating is generally 0.1-15 microns (and all values and ranges therebetween), and typically 0.2-2 microns. In another non-limiting embodiment, a TiNOx coating is applied to a portion or all of the outer surface of the frame for a prosthetic heart valve, and the TiNOx coating is formed by a) exposing the outer surface of a portion of all of the frame for a prosthetic heart valve to Ti particles (PVD, CVD, ALD and PE-CVD process) and/or a Ti containing solution to form a Ti layer on a portion of all of the frame for a prosthetic heart valve, and wherein the thickness of the Ti coating is 0.05-5 microns, and b) exposing the Ti coating to a nitrogen and oxygen source such as nitrogen gas, oxygen gas, a nitrogen containing gas compound and/or an oxygen containing gas compound to form a TiNOx coating, and wherein ratio of N to O when forming the TiNOx coating is generally 1:10 to 10:1, and wherein the coating thickness of the TiNOx coating is 0.2-5 microns. In another non-limiting embodiment, a TiNOx coating is applied to a portion or all of the outer surface of the frame for a prosthetic heart valve, and the TiNOx coating is formed by exposing a portion or all of the outer surface of the frame for a prosthetic heart valve to Ti particles and a nitrogen and oxygen source such as nitrogen gas, oxygen gas, a nitrogen containing gas compound and/or an oxygen containing gas compound to form a TiNOx coating, and wherein ratio of N to O when forming the TiNOx coating is generally 1:10 to 10:1, and wherein the coating thickness of the TiNOx coating is 0.2-5 microns. In another non-limiting embodiment, the enhancement layer composition generally includes 20-85 wt. % Ti (and all values and ranges therebetween), 0.5-35 wt. % N (and all values and ranges therebetween), 0-10 wt. % Re (and all values and ranges therebetween), and 0.5-35 wt. % O (and all values and ranges therebetween). In another non-limiting embodiment, a coating of TiNOx was formed on the frame for a prosthetic heart valve by reactive physical vapor deposition in a vacuum chamber. Depending on the oxygen-nitrogen ratio during vapor deposition, a coating deposit of TiNOx with defined composition and resistivity can be coated on the outer surface of the frame for a prosthetic heart valve.

In accordance with another and/or alternative non-limiting aspect of the present disclosure, the frame for a prosthetic heart valve can be partially or fully coated with an enhancement layer composition that includes a zirconium nitride (ZrN) coating. The enhancement layer can be used to improve hardness, improve toughness, improve resistance to corrosion and oxidation, reduced friction, and/or form a reduced stick surface when in contact with many different materials. In one non-limiting embodiment all or a portion of the outer surface of the frame for a prosthetic heart valve is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to nitrogen gas and/or a nitrogen containing gas compound to cause the nitrogen to react with the Zn metal coating to form a layer of ZrN on the outer surface of the Zr metal coating and/or the outer surface of the frame for a prosthetic heart valve. Particles of Zr metal can optionally be mixed with nitrogen gas and/or a nitrogen containing gas compound to facilitate in the formation of the ZrN coating. When Zr metal particles are used, the initial Zr coating layer on the frame for a prosthetic heart valve can optionally be eliminated. The ZrN coating has been found to produce a gold-colored enhancement layer color. In another non-limiting embodiment, the enhancement layer composition generally includes 35-90 wt. % Zr (and all values and ranges therebetween), 5-25 wt. % N (and all values and ranges therebetween), 0-10 wt. % Re (and all values and ranges therebetween), 0-20 wt. % Si (and all values and ranges therebetween), 0-2 wt. % O (and all values and ranges therebetween), and 0-2 wt. % C (and all values and ranges therebetween). In another non-limiting embodiment, the enhancement layer composition generally includes 80-90 wt. % Zr, 10-20 wt. % N, 0-8 wt. % Re, 0-1 wt. % Si, 0-1 wt. % O, and 0-1 wt. % C.

In accordance with another and/or alternative non-limiting aspect of the present disclosure, the frame for a prosthetic heart valve can be partially or fully coated with an enhancement layer composition that includes a zirconium oxide ($ZrO_2$) coating. The enhancement layer can be used to improve hardness, improve toughness, improve resistance to corrosion and oxidation, reduced friction, and/or form a reduced stick surface when in contact with many different materials. In one non-limiting embodiment all or a portion of the outer surface of the frame for a prosthetic heart valve is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to oxygen gas and/or oxygen containing gas compound to cause the oxygen to react with the Zn metal coating to form a layer of zirconium oxide ($ZrO_2$) on the outer surface of the Zr metal coating and/or the outer surface of the frame for a prosthetic heart valve. Particles of Zr metal can optionally be mixed with oxygen gas and/or an oxygen containing gas compound to facilitate in the formation of the $ZrO_2$ coating. When Zr metal particles are used, the initial Zr coating layer on the frame for a prosthetic heart valve can optionally be eliminated. The zirconium oxide ($ZrO_2$) coating has been found to produce a blue colored enhancement layer color. In another non-limiting embodiment, the enhancement layer composition generally includes 35-90 wt. % Zr (and all values and ranges therebetween), 10-35 wt. % O (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % C (and all values and ranges therebetween). In another non-limiting embodiment, the enhancement layer composition generally includes 70-80 wt. % Zr, 20-30 wt. %, 0-1 wt. % N, 0-8 wt. % Re, 0-1 wt. % Si, and 0-1 wt. % C.

In accordance with another and/or alternative non-limiting aspect of the present disclosure, the frame for a prosthetic heart valve can be partially or fully coated with an enhancement layer composition that includes both a zirconium oxide ($ZrO_2$) coating and a zirconium nitride coating (ZrN). The enhancement layer can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to a) both oxygen gas and/or oxygen containing gas compound and also to nitrogen gas and/or nitrogen containing gas compound, b) nitrogen gas and/or nitrogen containing gas compound and then to oxygen gas and/or oxygen containing gas compound, or c) oxygen gas and/or oxygen gas containing compound and then to nitrogen gas and/or nitrogen gas containing compound. The coating composition of the zirconium oxide ($ZrO_2$) coating and the zirconium nitride coating (ZrN) are similar or the same as discussed above. As discussed above, Particles of Zr metal can optionally be mixed with oxygen gas and/or an oxygen containing gas compound to facilitate in the formation of the $ZrO_2$ coating and the nitrogen gas and/or nitrogen gas containing compound to facilitate in the formation of the ZrN coating. When Zr metal particles are used, the initial Zr coating layer on the frame for a prosthetic heart valve can optionally be eliminated.

In accordance with another and/or alternative non-limiting aspect of the present disclosure, the frame for a prosthetic heart valve can be partially or fully coated with an enhancement layer composition that includes a zirconium oxycarbide (ZrOC) coating. The enhancement layer can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to a) both to oxygen gas and/or an oxygen containing gas compound and to carbon and/or a carbon containing gas compound (e.g., methane and/or acetylene gas), b) carbon and/or a carbon containing gas compound and then to oxygen gas and/or an oxygen containing gas compound, or c) oxygen gas and/or oxygen containing gas compound and then to carbon and/or carbon containing gas compound. Particles of Zr metal can optionally be mixed with oxygen gas and/or an oxygen containing gas compound and the carbon and/or carbon containing gas compound to facilitate in the formation of the zirconium oxycarbide (ZrOC) coating. When Zr metal particles are used, the initial Zr coating layer on the frame for a prosthetic heart valve can optionally be eliminated. In another non-limiting embodiment, the enhancement layer composition generally includes 40-95 wt. % Zr (and all values and ranges therebetween), 5-25 wt. % O (and all values and ranges therebetween), and 10-40 wt. % C (and all values and ranges therebetween), 0-2 wt. % N (and all values and ranges therebetween), 0-10 wt. % Re (and all values and ranges therebetween), and 0-20 wt. % Si (and all values and ranges therebetween). In another non-limiting embodiment, the enhancement layer composition generally includes 40-65 wt. % Zr, 5-25 wt. % O, and 25-40 wt. % C, 0-1 wt. % N, 0-8 wt. % Re, and 0-1 wt. % Si.

In accordance with another and/or alternative non-limiting aspect of the present disclosure, one or more components of the frame for a prosthetic heart valve can be partially or fully coated with an enhancement layer composition that includes a zirconium oxynitride (ZrNxOy) [e.g., cubic ZrN:O, cubic $ZrO_2$:N, tetragonal $ZrO_2$:N, and monoclinic $ZrO_2$:N phase coatings]. A portion or all of the outer surface of the one or more components of the frame for a prosthetic heart valve can include the zirconium oxynitride (ZrNxOy). The enhancement layer can be used to improve hardness, improve toughness, improve resistance to corrosion and oxidation, reduced friction, form a reduced stick surface when in contact with many different materials, and/or promote nitric oxide formation on the surface of the coating. In one non-limiting embodiment, all or a portion of the outer surface of the one or more components of the frame for a prosthetic heart valve are optionally initially coated with Zr metal. The Zr metal coating, when applied, can be applied by PVD, CVD, ALD and PE-CVD in an inert environment. The coating thickness of Zr metal is 0.05-15 microns (and all values and ranges therebetween). As can be appreciated, the initial Zr coating is optional. Thereafter, the Zr metal coating is exposed to zirconium particles and a nitrogen and oxygen mixture that can include nitrogen gas, oxygen gas, a nitrogen containing gas compound and/or an oxygen containing gas compound to cause the nitrogen and oxygen to react with the Zr metal coating, if such coating is used, and/or with the Zr metal particles to form a layer of ZrNxOy on the outer surface of the Zr metal coating and/or the outer surface of the one or more components of the frame for a prosthetic heart valve. The ratio of the N to the O can be varied to control the amount of O and N in the ZrNxOy coating. If a zirconium layer is not preapplied, the ZrNxOy coating can be formed by exposing the outer surface of one or more components of the frame for a prosthetic heart valve to zirconium particles and a nitrogen and oxygen source such as nitrogen gas, oxygen gas, a nitrogen containing gas compound and/or an oxygen containing gas compound. The ratio of N to O when forming the ZrNxOy coating is generally 1:10 to 10:1 (and all values and ranges therebetween). The coating thickness of the ZrNxOy coating is generally 0.1-15 microns (and all values and ranges therebetween), and typically 0.2-2 microns. In another non-limiting embodiment, a ZrNxOy coating is applied to a portion or all of the outer surface of the one or more components of the frame for a prosthetic heart valve, and the ZrNxOy coating is formed by a) exposing the outer surface of a portion of all of the one or more components of the frame for a prosthetic heart valve to Zr particles (PVD, CVD, ALD and PE-CVD process) and/or a Zr containing solution to form a Zr layer on a portion of all of the one or more components of the frame for a prosthetic heart valve, and wherein the thickness of the Zr coating is 0.05-5 microns, and b) exposing the Zr coating to a nitrogen and oxygen source such as nitrogen gas, oxygen gas, a nitrogen containing gas compound and/or an oxygen containing gas compound to form a ZrNxOy coating, and wherein ratio of N to O when forming the ZrNxOy coating is generally 1:10 to 10:1, and wherein the coating thickness of the ZrNxOy coating is 0.2-5 microns. In another non-limiting embodiment, a ZrNxOy coating is applied to a portion or all of the outer surface of the one or more components of the frame for a prosthetic heart valve, and the ZrNxOy coating is formed by exposing a portion or all of the outer surface of the one or more components of the frame for a prosthetic heart valve to Zr particles and a nitrogen and oxygen source such as nitrogen gas, oxygen gas, a nitrogen containing gas compound and/or an oxygen containing gas compound to form a ZrNxOy coating, and wherein ratio of N to O when forming the ZrNxOy coating is generally 1:10 to 10:1, and wherein the coating thickness of the ZrNxOy coating is 0.2-5 microns. In another non-limiting embodiment, the enhancement layer composition generally includes 20-85 wt. % Zr (and all values and ranges therebetween), 0.5-35 wt. % N (and all values and ranges therebetween), and 0.5-35 wt. % O (and all values and ranges therebetween). In another non-limiting embodiment, a coating of ZrNxOy was formed on one or more components of the frame for a prosthetic heart valve by reactive physical vapor deposition in a vacuum chamber. Depending on the oxygen-nitrogen ratio during vapor deposition, a coating deposit of ZrNxOy with defined composition and resistivity can be coated on the outer surface of the one or more components of the frame for a prosthetic heart valve.

In accordance with another and/or alternative non-limiting aspect of the present disclosure, the frame for a prosthetic heart valve can be partially or fully coated with an enhancement layer composition that includes a zirconium-nitrogen-carbon (ZrNC) coating. The enhancement layer can be used to improve hardness, improve toughness, improve resistance to corrosion and oxidation, reduced friction, and/or form a reduced stick surface when in contact with many different materials. In one non-limiting embodiment all or a portion of the outer surface of the frame for a prosthetic heart valve is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to nitrogen gas and/or a nitrogen containing gas compound and then to carbon and/or a carbon containing gas compound (e.g., methane and/or acetylene gas). The color of the ZrNC will vary depending on the amount of C and N in the coating. Particles of Zr metal can optionally be mixed with nitrogen gas and/or a nitrogen containing gas compound and the carbon and/or a carbon containing gas compound to facilitate in the formation of the ZrNC coating. When Zr metal particles are used, the initial Zr coating layer on the frame for a prosthetic heart valve can optionally be eliminated. In one non-limiting embodiment, the enhancement layer composition generally includes 40-95 wt. % Zr (and all values and ranges therebetween), 5-40 wt. % N (and all values and ranges therebetween), and 5-40 wt. % C (and all values and ranges therebetween), 0-2 wt. % O (and all values and ranges therebetween), 0-10 wt. % Re (and all values and ranges therebetween), and 0-20 wt. % Si (and all values and ranges therebetween). In another non-limiting embodiment, the enhancement layer composition generally includes 40-80 wt. % Zr, 5-25 wt. % N, and 5-25 wt. % C, 0-1 wt. % O, 0-8 wt. % Re, and 0-1 wt. % Si.

In one non-limiting embodiment, a portion or all of the medical device is formed of a metal alloy that includes a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, 1) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 awt. %, and wherein a portion or all of the outer surface of the metal alloy is coated with an enhancement layer (e.g., chromium nitride (CrN), diamond-like carbon (DLC), titanium nitride (TiN), titanium nitride oxide (TiNOx), zirconium nitride (ZrN), zirconium oxide ($ZrO_2$), zirconium-nitrogen-carbon (ZrNC), zirconium OxyCarbide (ZrOC), zirconium oxynitride (ZrNxOy) [e.g., cubic ZrN:O, cubic $ZrO_2$:N, tetragonal $ZrO_2$:N, and monoclinic $ZrO_2$:N phase coatings]), and wherein the outer surface of the metal alloy optionally includes an adhesion layer, which adhesion layer is optionally a metallic layer that includes titanium or zirconium.

In non-limiting configuration, a portion or all of the medical device is formed of a metal alloy that includes a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, 1) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 awt. %, and wherein the metal alloy is coated with a metal oxynitride layer (e.g., titanium nitride oxide and/or (TiNOx), zirconium oxynitride (ZrNxOy), etc.), which metal oxynitride layer can optionally be used to promotes and/or facilitates in a) formation or generation of nitric oxide (NO), b) stimulation of endothelial cells, c) a modulation of endothelial cells, d) reduce neointimal hyperplasia, e) reduce tissue proliferation, f) reduce platelet activation, g) reduce thrombosis, h) reduce restenosis, i) promote endothelial cell angiogenesis, and/or j) improved healing on and/or about the medical device, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a titanium-nickel alloy or a titanium-nickel alloy that includes at least 5 awt. % rhenium, and wherein a portion or all of the outer surface of the metal alloy is coated with a metal oxynitride layer (e.g., titanium nitride oxide and/or (TiNOx), zirconium oxynitride (ZrNxOy), etc.), and wherein all or a portion of components other than the frame of the prosthetic heart valve (e.g., leaflet, skirts, etc.) are optionally coated with a metal oxynitride layer, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a stainless-steel alloy or a stainless-steel alloy that includes at least 5 awt % rhenium, and wherein a portion or all of the outer surface of the metal alloy is coated with a metal oxynitride layer (e.g., titanium nitride oxide and/or (TiNOx), zirconium oxynitride (ZrNxOy), etc.), and wherein all or a portion of components other than the frame of the prosthetic heart valve (e.g., leaflet, skirts, etc.) are optionally coated with a metal oxynitride layer, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a cobalt-chromium alloy or a cobalt-chromium alloy that includes at least 5 awt % rhenium, and wherein a portion or all of the outer surface of the metal alloy is coated with a metal oxynitride layer (e.g., titanium nitride oxide and/or (TiNOx), zirconium oxynitride (ZrNxOy), etc.), and wherein all or a portion of components other than the frame of the prosthetic heart valve (e.g., leaflet, skirts, etc.) are optionally coated with a metal oxynitride layer, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a TiAlV alloy or a TiAlV alloy that includes at least 5 awt % rhenium, and wherein a portion or all of the outer surface of the metal alloy is coated with a metal oxynitride layer (e.g., titanium nitride oxide and/or (TiNOx), zirconium oxynitride (ZrNxOy), etc.), and wherein all or a portion of components other than the frame of the prosthetic heart valve (e.g., leaflet, skirts, etc.) are optionally coated with a metal oxynitride layer, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a refractory metal alloy or a refractory metal alloy that includes at least 5 awt % rhenium, and wherein a portion or all of the outer surface of the metal alloy is coated with a metal oxynitride layer (e.g., titanium nitride oxide and/or (TiNOx), zirconium oxynitride (ZrNxOy), etc.), and wherein all or a portion of components other than the frame of the prosthetic heart valve (e.g., leaflet, skirts, etc.) are optionally coated with a metal oxynitride layer, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a metal alloy that includes at least 5 awt % rhenium, and wherein a portion or all of the outer surface of the metal alloy is coated with a metal oxynitride layer (e.g., titanium nitride oxide and/or (TiNOx), zirconium oxynitride (ZrNxOy), etc.), and wherein all or a portion of components other than the frame of the prosthetic heart valve (e.g., leaflet, skirts, etc.) are optionally coated with a metal oxynitride layer, and wherein the outer surface of the metal alloy optionally includes an adhesion layer, which adhesion layer is optionally a metallic layer that includes titanium or zirconium.

In accordance with another and/or alternative non-limiting aspect of the present disclosure, there is provided a prosthetic heart valve that includes an expandable frame, a leaflet structure supported by the frame, and an optional inner skirt secured to the surface of the frame and/or leaflet structure. The prosthetic heart valve can be implanted in the annulus of the native aortic valve; however, the prosthetic heart valve also can be configured to be implanted in other valves of the heart (e.g., tricuspid valve, pulmonary valve, mitral valve). The prosthetic heart valve has a "lower" end and an "upper" end, wherein the lower end of the prosthetic heart valve is the inflow end and the upper end of the prosthetic heart valve is the outflow end.

In accordance with another and/or alternative non-limiting aspect of the present disclosure, the expandable frame of the prosthetic heart valve is configured to be radially collapsible to a collapsed or crimped state for introduction into the body (e.g., on a delivery catheter, etc.) and radially expandable to an expanded state for implanting the prosthetic heart valve at a desired location in the heart (e.g., the aortic valve, tricuspid valve, pulmonary valve, mitral valve, etc.). The expandable frame of the prosthetic heart valve is formed of a plastically-expandable material that permits crimping of the frame to a smaller profile for delivery and expansion of the frame at the treatment site. The expansion of the crimped frame of the prosthetic heart can be by an expansion device such as, but not limited to, a balloon of on a balloon catheter. The expandable frame and/or prosthetic heart valve can be configured to be crimped to a diameter of less than 24 FR (e.g., less than 8 mm, 5-7.9 mm, etc.) and the expandable frame and/or prosthetic heart valve can be configured to be expanded to a diameter of at least 14 mm (e.g., 14-35 mm and all values and ranges therebetween); however, it can be appreciated that the expandable frame and/or prosthetic heart valve can be designed to be crimped to larger diameters, and/or be expanded to larger diameters.

In accordance with another and/or alternative non-limiting aspect of the present disclosure, the expandable frame of the prosthetic heart valve is formed of a plurality of angularly spaced angular articulating members and vertically extending axial longitudinal members. The angular articulating members and vertically extending axial longitudinal members are interconnected to form a variety of patterns (e.g., zig-zag pattern, saw-tooth pattern, triangular pattern, polygonal pattern, oval pattern, etc.). One or more of the angular articulating members and/or vertically extending axial longitudinal members can have the same or different thicknesses and/or cross-sectional shape and/or cross-sectional area.

In accordance with another and/or alternative non-limiting aspect of the present disclosure, the prosthetic heart valve includes a) an expandable frame that is balloon expandable, mechanically expandable or self-expanding, and b) a least 1 leaflet (e.g., 1-6 leaflets and all values and ranges therebetween). The one or more leaflets are supported by the expandable frame. The prosthetic heart valve can include an inner and/or outer skirt. The expandable frame has multiple frame cells organized in rows or columns arranged in a cylindrical shape with a proximal and distal end. The metal frame is formed of a metal alloy that plastically deforms and/or elastically deforms to enable the expandable frame to be expanded and compressed (crimped) to different geometrical states.

In accordance with another and/or alternative non-limiting aspect of the present disclosure, the frame has an open cell configuration wherein the cells of the expandable metal frame comprise axial longitudinal members and angular articulating members, wherein the angular articulating members are connected to each other through articulating joints, and wherein the axial longitudinal members are connected to angular articulating members through a base join. In one non-limiting embodiment, the expandable frame has no more than 20% longitudinal foreshortening along a longitudinal axis of the expandable frame when the expandable frame is plastically deformed (e.g., expanded from the crimped to the uncrimped position), and typically no more than 5% longitudinal foreshortening, and the frame cells are comprised of at least two axial longitudinal members, and at least two angular articulating member pairs, wherein each member pair includes at least two angular articulating members connected by an articulating joint, and wherein during expansion or compression of the expandable frame, the overall longitudinal length of the frame cells do not exceed the height of the axial longitudinal members. In one non-limiting configuration, the expandable frame is formed of multiple non-foreshortening frame cells. In another non-limiting configuration, the angular articulating members in all cells in a row of frame cells and/or in a column of frame cells have the same length. In another non-limiting configuration, the length of the angular articulating members is measured from peak to peak of joints defining the ends of an angular articulating member, and wherein the sum of the length of the angular articulating members is less than or equal to the sum of the length of the axial longitudinal members. In another non-limiting configuration, the geometry of the angular articulating member has independent curvature on its width through at least a portion of the length of the angular articulating member. In another non-limiting embodiment, the complete frame does not foreshorten during the expansion and/or crimping of the expandable frame even when one or more of the frame cells foreshorten during the expansion and/or crimping of the expandable frame. In another non-limiting configuration, the longitudinal length between the proximal end of the expandable frame and the distal end of the expandable frame is mostly constant or constant during changes in diameter of the expandable frame. In another non-limiting configuration, one or more longitudinal posts extend through the complete distance from the distal end to the proximal end of the expandable frame. In another non-limiting configuration, the expandable frame includes at least one axial longitudinal member extending from the distal end of the frame to the proximal end of the frame, and a commissural attachment area is located between the proximal and distal ends of the expandable frame. In another non-limiting configuration, a longitudinal distance from the commissural attachment area to the proximal end of the frame is predominantly constant during expansion and/or crimping of the expandable frame. In another non-limiting configuration, the rows and columns of the frame cells of the expandable frame are made of frame cells of equal width or equal height as adjacent circumferential or axial cells. In another non-limiting configuration, the difference in cross-sectional area of a window area of one or more frame cells of the expandable frame do not differ by more than 20% when compared to other cells in the same row of frame cell, and/or in the same column cells in in the expandable frame. In another non-limiting configuration, the expandable frame is made of even or odd numbers of cells per row. In another non-limiting configuration, the expandable frame includes an odd numbers of cells. In another non-limiting configuration, one or more or all of the rows of cells of the expandable frame are formed of 9 cells. In another non-limiting configuration, only the distal row is constructed from an odd number of frame cells, and the other rows are formed of an even number of frame cells. In another non-limiting configuration, the prosthetic heart valve is inserted in the heart such that when the expandable frame is expanded, one or more of the frame cells will partially or fully be positioned across the access to a coronary artery.

In accordance with another and/or alternative non-limiting aspect of the present disclosure, the material used to form the expandable metal frame contains little or no nickel. Nickel and cobalt are commonly used alloys in the frames of commercial prosthetic heart valves, even though such materials have exhibited suboptimal results in terms of biocompatibility. In one non-limiting embodiments, the metal alloy used to form the expandable frame includes only trace amounts (e.g., less than 0.1 wt. %) of cobalt, chromium, and/or nickel. In another non-limiting configuration, the metal alloy used to form the expandable frame is completely absent nickel, chromium and/or cobalt. In another non-limiting configuration, the metal alloy used to form the expandable frame includes rhenium and optionally chromium and/or molybdenum. In another non-limiting configuration, the metal alloy used to form the expandable frame includes up to 70 wt. % rhenium and one or more metals selected from the group consisting of Mo, Cr, Co, Ni, Ti, Ta, Nb, Zr, and/or W.

In accordance with another and/or alternative non-limiting aspect of the present disclosure, the material used to form the expandable metal frame has high yield strength to confer radial strength to the expandable frame. In one non-limiting embodiment, the material used to form the expandable metal frame has a yield strength of at least 110 ksi. In one non-limiting embodiment, the material used to form the expandable metal frame has an elongation of at least 20%. In one non-limiting embodiment, the material used to form the expandable metal frame has a yield strength of at least 110 Ksi and an elongation of at least 20%. In one non-limiting embodiment, the material used to form the expandable metal frame has a yield strength of at least 110 Ksi and and/or an elongation of at least 20% when the expandable frame is in its finished state (e.g., Finished state is defined as material properties after undergoing any material processing such as heating, annealing, cold working, during manufacturing, hot working, etc. Finished state implies the material ready to be sterilized or implanted or shipped to customer in the form of a medical device). In one non-limiting embodiment, the material used to form the expandable metal frame has a low recoil to limit tissue or conduction damage during implantation. In another non-limiting embodiment, the material used to form the expandable metal frame has a modulus of elasticity of at least 52000 ksi and/or a recoil of no more than 5% when the frame is plastically deformed (e.g., expanded from the crimped to the expanded state, crimped, etc.) and no further expansion force is being applied to the expanded frame (e.g., the delivery balloon has been deflated and applies no load on the expanded frame).

In accordance with another and/or alternative non-limiting aspect of the present disclosure, the expandable frame can include distinguishing features which allows for rotational alignment of the expandable frame with the commissures of the native heart valve. In one non-limiting embodiment, the one or more distinguishing feature on the expandable heart valve are asymmetrical for identification of rotational alignment of the expandable frame. In another non-limiting embodiment, the one or more distinguishing features are attached directly to the commissure of the prosthetic heart valve frame. In another non-limiting embodiment, the one or more the distinguishing feature can be formed of radiopaque material which allows for high visibility during the insertion procedure of the prosthetic heart valve in the heart. In another non-limiting embodiment, the one or more distinguishing feature are at least partially made from a material with a density of at least 10 mg/cm$^3$. The one or more distinguishing feature can be formed of the same or different material from the main body of the frame.

In accordance with another and/or alternative non-limiting aspect of the present disclosure, the expandable frame of the prosthetic heart valve can be optionally coated with a polymer material (e.g., silicone, PTFE, ePTFE, polyurethane, polyolefins, hydrogels, biological materials (e.g., pericardium or biological polymers such as collagen, gelatin, or hyaluronic acid derivatives), etc.). The coating can be used to partially or fully encapsulate the angular articulating members and/or vertically extending axial longitudinal members on the frame and/or to fill-in the openings between the angular articulating members and/or vertically extending axial longitudinal members on the frame.

In accordance with another and/or alternative non-limiting aspect of the present disclosure, there is provided a prosthetic heart valve that optionally includes an inner skirt, and wherein the inner skirt that can be formed of a variety of flexible materials (e.g., polymer [e.g., polyethylene terephthalate (PET), polyester, nylon, Kevlar®, silicon, etc.], composite material, metal, fabric material, etc.). In one non-limiting embodiment, the material used to partially or fully form the inner skirt can optionally be substantially non-elastic (i.e., substantially non-stretchable and non-compressible). In another non-limiting embodiment, the material used to partially or fully form the inner skirt can optionally be a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The inner skirt can optionally be formed from a combination of a cloth or fabric material that is coated with a flexible material or with a stretchable and/or compressible material so as to provide additional structural integrity to the inner skirt. The size, configuration, and thickness of the inner skirt is non-limiting (e.g., thickness of 0.1-20 mils and all values and ranges therebetween). The inner skirt can be secured to the inside and/or outside of the frame using various means (e.g., sutures, clamp arrangement, etc.). In another non-limiting embodiment, the inner skirt can be made out of a woven material; however, non-woven materials can also or alternatively be used. In another non-limiting embodiment, the inner skirt (when used) can be used to 1) at least partially seal and/or prevent perivalvular leakage, 2) at least partially secure the leaflet structure to the frame, 3) at least partially protect the leaflets from damage during the crimping and/or expansion process, and/or 4) at least partially protect the leaflets from damage during the operation of the prosthetic heart valve in the heart.

In accordance with another and/or alternative non-limiting aspect of the present disclosure, there is provided a prosthetic heart valve that optionally includes an outer or sleeve that is positioned at least partially about the exterior region of the frame. The outer skirt or sleeve generally is positioned completely around a portion of the outside of the frame. Generally, the outer skirt is positioned about the lower portion of the frame, but does not fully cover the upper half of the frame; however, this is not required. The outer skirt can be connected to the frame by a variety of arrangements (e.g., sutures, adhesive, melted connection, clamping arrangement, etc.). At least a portion of the outer skirt can optionally be located on the interior surface of the frame.

Generally, the outer skirt is formed of a more flexible and/or compressible material than the inner skirt; however, this is not required. The outer skirt can be formed of a variety of a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The outer skirt can optionally be formed from a combination of a cloth or fabric material that is coated with the stretchable and/or compressible material to provide additional structural integrity to the outer skirt. In another non-limiting embodiment, the outer skirt can be made out of a woven material; however, non-woven materials can also or alternatively be used. The size, configuration, and thickness of the outer skirt is non-limiting. The thickness of the outer skirt is generally 0.1-20 mils (and all values and ranges therebetween).

In accordance with another and/or alternative non-limiting aspect of the present disclosure, the prosthetic heart valve includes a leaflet structure that can be can be attached to the frame and/or skirt. The connection arrangement used to secure the leaflet structures to the frame and/or skirt is non-limiting (e.g., sutures, melted bold, adhesive, clamp arrangement, etc.). The material used to form the leaflet structures include polymers, bovine pericardial tissue, bovine tissue, porcine tissue, biocompatible synthetic materials, or various other suitable natural or synthetic materials. The tissue used to form the one or more leaflets can optionally be treated/stabilized through a method of collagen cross linking and thereafter stored dry or wet (e.g., tissue is stored dry after a glycerin-based dehydration process, etc.). In one non-limiting embodiment, the leaflet structure comprised of two or more leaflets (e.g., 2, 3, 4, 5, 6, etc.). In one non-limiting arrangement, the leaflet structure includes three leaflets arranged to collapse in a tricuspid arrangement. The configuration of the leaflet structures is non-limiting. In another non-limiting embodiment, the leaflets of the leaflet structure can optionally be secured to one another at their adjacent sides to form commissures of the leaflet structure (the edges where the leaflets come together). The leaflet structure can be secured together by a variety of connection arrangement (e.g., sutures, adhesive, melted bond, clamping arrangement, etc.). In another non-limiting embodiment, one or more of the leaflets can optionally include reinforcing structures or strips to 1) facilitate in securing the leaflets together, 2) facilitate in securing the leaflets to the skirt and/or frame, and/or 3) inhibit or prevent tearing or other types of damage to the leaflets.

In accordance with another and/or alternative non-limiting aspect of the present disclosure, there is provided a prosthetic heart valve that is configured to be inserted into a desired location in the body (e.g., the aortic valve, tricuspid valve, pulmonary valve, mitral valve). The frame of the prosthetic heart valve can be at least partially formed of a plastically-expandable material that permits crimping of the frame to a smaller profile for delivery and expansion of the prosthetic heart valve to a larger profile. The expansion of the crimped frame can be optionally be use of an expansion device such as, but not limited to, a balloon of on a balloon catheter.

In accordance with another and/or alternative non-limiting aspect of the present disclosure, the use of the metal alloy to partially or fully form the frame of the prosthetic heart valve can be used to increase the strength and/or hardness and/or durability of the frame of the prosthetic heart valve as compared with stainless steel or chromium-cobalt alloys or titanium alloys; thus, less quantity of metal alloy can be used in the frame of the prosthetic heart valve to achieve similar strengths as compared to frames of prosthetic heart valves formed of different metals. As such, the resulting prosthetic heart valve can be made smaller and less bulky by use of the metal alloy without sacrificing the strength and durability of the prosthetic heart valve. Such a prosthetic heart valve can have a smaller profile, thus can be inserted in smaller areas, openings, and/or passageways. The metal alloy also can increase the radial strength of the frame of the prosthetic heart valve. For instance, the thickness of the angular articulating members and/or vertically extending axial longitudinal members of the frame of the prosthetic heart valve and/or the wires used to at least partially form the frame of the prosthetic heart valve can be made thinner and achieve a similar or improved radial strength as compared with thicker walled frames of prosthetic heart valves formed of stainless steel, titanium alloys, or cobalt and chromium alloys. The metal alloy also can improve stress-strain properties, bendability and flexibility of the frame of the prosthetic heart valve, thus increase the life of the prosthetic heart valve. For instance, the prosthetic heart valve can be used in regions that subject the prosthetic heart valve to bending. Due to the improved physical properties of the prosthetic heart valve from the metal alloy, the prosthetic heart valve has improved resistance to fracturing in such frequent bending environments. In addition or alternatively, the improved bendability and flexibility of the frame of the prosthetic heart valve due to the use of the metal alloy can enable the prosthetic heart valve to be more easily inserted into various regions of a body. The metal alloy can also reduce the degree of recoil during the crimping and/or expansion of the frame of the prosthetic heart valve. For example, the prosthetic heart valve better maintains its crimped form and/or better maintains its expanded form after expansion due to the use of the metal alloy. As such, when the prosthetic heart valve is to be mounted onto a delivery device when the prosthetic heart valve is crimped, the prosthetic heart valve better maintains its smaller profile during the insertion of the prosthetic heart valve into various regions of a body. Also, the prosthetic heart valve better maintains its expanded profile after expansion so as to facilitate in the success of the prosthetic heart valve in the treatment area. In addition to the improved physical properties of the prosthetic heart valve by use of the metal alloy, the metal alloy can optionally have improved radiopaque properties as compared to standard materials such as stainless steel or cobalt-chromium alloy, thus reducing or eliminating the need for using marker materials on the prosthetic heart valve.

In accordance with another and/or alternative non-limiting aspect of the present disclosure, the use of the metal alloy to form all or a portion of the prosthetic heart valve can result in several advantages over prosthetic heart valves formed from other materials. These advantages include, but are not limited to:

The metal alloy used to partially or fully form the frame of the prosthetic heart valve optionally has increased strength and/or hardness as compared with stainless steel, chromium-cobalt alloys, or titanium alloys, thus a less quantity of metal alloy can be used in the prosthetic heart valve to achieve similar strengths as compared to prosthetic heart valves formed of different metals. As such, the resulting prosthetic heart valve can be made smaller and less bulky by use of the metal alloy without sacrificing the strength and durability of the prosthetic heart valve. The prosthetic heart valve can also have a smaller profile, thus can be inserted into smaller areas, openings, and/or passageways. The thinner angular articulating members and/or vertically extending axial longitudinal members of metal alloy to form the frame or other portions of the prosthetic heart valve can be used to form a frame or other portion of the prosthetic heart valve having a strength that would require thicker angular articulating members and/or vertically extending axial longitudinal members or other structures of the prosthetic heart valve when formed by stainless steel, chromium-cobalt alloys, or titanium alloys.

The increased strength of the metal alloy used in the frame of the prosthetic heart valve optionally results in the increased radial strength of the prosthetic heart valve. For instance, the thickness of the walls of the prosthetic heart valve can optionally be made thinner and achieve a similar or improved radial strength as compared with thicker walled prosthetic heart valves formed of stainless steel, cobalt and chromium alloy, or titanium alloy.

The metal alloy used to partially or fully form the frame of the prosthetic heart valve optionally has a reduced degree of recoil during the crimping and/or expansion of the prosthetic heart valve compared with stainless steel, chromium-cobalt alloys, or titanium alloys. The prosthetic heart valve formed of the metal alloy better maintains its crimped form and/or better maintains its expanded form after expansion due to the use of the metal alloy. As such, when the prosthetic heart valve is to be mounted onto a delivery device when the prosthetic heart valve is crimped, the prosthetic heart valve better maintains its smaller profile during the insertion of the prosthetic heart valve in a body passageway. Also, the prosthetic heart valve better maintains its expanded profile after expansion to facilitate in the success of the prosthetic heart valve in the treatment area.

The use of the metal alloy in the frame of the prosthetic heart valve optionally results in the prosthetic heart valve better conforming to an irregularly shaped body passageway when expanded in the body passageway compared to a prosthetic heart valve formed by stainless steel, chromium-cobalt alloys, or titanium alloys.

The metal alloy used to partially or fully form the frame of the prosthetic heart valve optionally has improved radiopaque properties compared to standard materials such as stainless steel or cobalt-chromium alloy, thus reducing or eliminating the need for using marker materials on the prosthetic heart valve. For example, the metal alloy is at least about 10-20% more radiopaque than stainless steel or cobalt-chromium alloy.

The metal alloy used to partially or fully form the frame of the prosthetic heart valve optionally has improved fatigue ductility when subjected to cold-working compared to the cold-working of stainless steel, chromium-cobalt alloys, or titanium alloys.

The metal alloy used to partially or fully form the frame of the prosthetic heart valve optionally has improved durability compared to stainless steel, chromium-cobalt alloys, or titanium alloys.

The metal alloy used to partially or fully form the frame of the prosthetic heart valve optionally has improved hydrophilicity compared to stainless steel, chromium-cobalt alloys, or titanium alloys.

The metal alloy used to partially or fully form the frame of the prosthetic heart valve optionally has reduced ion release in the body passageway compared to stainless steel, chromium-cobalt alloys, or titanium alloys.

The metal alloy used to partially or fully form the frame of the prosthetic heart valve optionally is less of an irritant to the body than stainless steel, cobalt-chromium alloy, or titanium alloys, thus can result in reduced inflammation, faster healing, increased success rates of the prosthetic heart valve. When the prosthetic heart valve is expanded in a body passageway, some minor damage to the interior of the passageway can occur. When the body begins to heal such minor damage, the body has less adverse reaction to the presence of the metal alloy compared to other metals such as stainless steel, cobalt-chromium alloy, or titanium alloy.

The metal alloy used to partially or fully form the frame of the prosthetic heart valve optionally has a magnetic susceptibility that is lower that CoCr alloy, TiAlV alloys, and/or stainless steel, thus resulting in less incidence of potential defects to the prosthetic heart valve or complications to the patent after implantation of the prosthetic heart valve when the patient is subjected to an MRI or other prosthetic heart valve that generates a strong magnetic field.

In accordance with another and/or alternative non-limiting aspect of the present disclosure, the frame of the prosthetic heart valve has one or features that include, but are not limited to:

High Radial Strength.
Small or Low Crimp Profile.
Reduce Recoil when expanded and/or crimped.
Little or No Longitudinal Foreshortening when expanded.
Smooth curvature at peaks and along angular articulating members.
Symmetrical Design for restoration of valve function and visualization of frame.
Physical Markers on frame for commissural alignment.
Open 9 cell design.
Open cell aligned with Coronary for hemodynamic and reintervention.

In accordance with another and/or alternative non-limiting aspect of the present disclosure, the prosthetic heart valve includes radially collapsible and expandable frame, and a leaflet structure comprising a plurality of leaflets. The prosthetic heart valve can optionally include an annular skirt member, which annular skirt member can be positioned between the frame and the leaflet structure. Each side of the leaflets can be secured to an adjacent leaflet. The leaflets are connected to the frame of the prosthetic heart valve.

In accordance with another and/or alternative non-limiting aspect of the present disclosure, the prosthetic heart valve includes a radially collapsible and expandable frame that includes plurality of angular articulating members, a plurality of axial longitudinal members, and optionally one or more frame opening arrangements, and wherein the angular articulating members, the plurality of axial longitudinal members, and the optional one or more frame opening arrangements are connected together to form a plurality of cells in the frame. In one non-limiting arrangement, the expandable frame includes angular articulating members having first and second ends, and wherein a plurality of the angular articulating members have first and second ends that are connected to the axial longitudinal members, and/or frame opening arrangements. The combination of angular articulating members and axial longitudinal members or the combination of angular articulating members, axial longitudinal members, and frame opening arrangements are used to form each of the cells in the frame. In one non-limiting arrangement, the frame can be formed of two or more sets of cells, wherein each set of cells includes the same number of cells, and each of the set of cells optionally has the same number of cells, and each set of cells optionally have the same shape and size of cells that exist in one or more of the other sets of cells. In one non-limiting configuration, the frame is formed of three sets of cells, wherein each set of cell includes 6-9 cells. As can be appreciated, the frame can include 2-10 sets of cells (and all values and ranges therebetween) and each set of cells can include 2-16 cells (and all values and ranges therebetween). In one non-limiting configuration, the number, shape and size of the cells in each of the three sets of cells are mirror images of one another, and have the same shape and size.

In accordance with another and/or alternative non-limiting aspect of the present disclosure, the prosthetic heart valve includes a radially collapsible and expandable frame that includes one or more frame opening arrangements that are located on the top portion of the frame. Each of the frame opening arrangements can include a lower frame opening and an optional upper frame opening.

In accordance with another and/or alternative non-limiting aspect of the present disclosure, the prosthetic heart valve includes a radially collapsible and expandable frame that includes a plurality of the axial longitudinal members. In one non-limiting embodiment, one or more of the axial longitudinal members extends 80-100% (and all values and ranges therebetween) of the longitudinal length of the frame. In one non-limiting configuration, at least 50% (e.g., 50-100% and all values and ranges therebetween) of the axial longitudinal members extends 80-100% of the longitudinal length of the frame. In another non-limiting configuration, 10-45% (and all values and ranges therebetween) of the axial longitudinal members in the frame extend less than 80% (e.g., 30-79% and all values and ranges therebetween) of the longitudinal length of the frame. In another non-limiting configuration, 20-40% of the axial longitudinal members in the frame extend less than 80% of the longitudinal length of the frame. In another non-limiting embodiment, the axial longitudinal member is configured to limit or eliminate longitudinal foreshortening of the frame when the frame is plastically deformed (e.g., expanded from the crimped to the expanded position). When the frame includes a plurality of axial longitudinal members that have a longitudinal length of 80-100% of the longitudinal length of the frame and are spaced at various location about the about the perimeter of the frame, the axial longitudinal members facilitate in inhibiting or preventing longitudinal foreshortening of the frame when expanded. In one non-limiting configuration, a) the longitudinal length of two or more of the axial longitudinal members is 90-100% of the longitudinal length of the frame, and/or b) the one or more of the axial longitudinal members that are connected to a frame opening arrangement has a combined longitudinal length of 90-100% the longitudinal length of the frame, and wherein the axial longitudinal member configurations of a) and/or b) facilitate in inhibiting or preventing longitudinal foreshortening of the frame when expanded.

In accordance with another and/or alternative non-limiting aspect of the present disclosure, the prosthetic heart valve includes a radially collapsible and expandable frame that includes a plurality of the axial longitudinal members that are optionally formed of a plurality of axial longitudinal member segments. The one or more axial longitudinal members can be formed of a single piece of material or be formed of a plurality of pieces of material that have been connected together (e.g., solder connection, weld connection, adhesive connection, mechanical connection, etc.). The number of axial longitudinal member segments that are used to form each of the axial longitudinal members is non-limiting. In one non-limiting arrangement, the axial longitudinal members are formed of 2-3 axial longitudinal member segments. In one non-limiting embodiment, one or more or all of the axial longitudinal members are formed of a plurality of axial longitudinal member segments. In another non-limiting embodiment, one or more of the axial longitudinal members are formed for a single strut segment, and one or more of the axial longitudinal members are formed of a plurality of axial longitudinal member segments. In one non-limiting configuration, the frame includes one or more of the axial longitudinal members that are formed for a single strut segment, and one or more of the axial longitudinal members that are formed of a plurality of axial longitudinal member segments, and wherein a larger number (e.g., 55-90% and all values and ranges therebetween) of the axial longitudinal members are formed of a plurality of axial longitudinal member segments. In another non-limiting embodiment, the axial longitudinal member segments that form each of the axial longitudinal members are generally aligned along the longitudinal axis of the axial longitudinal member. In another non-limiting embodiment, thickness, width, and/or cross-sectional area of the axial longitudinal member along the longitudinal axis of the axial longitudinal member can be constant or vary. In one non-limiting configuration, the thickness, width, and/or cross-sectional area of each of the axial longitudinal members along the longitudinal axis of the axial longitudinal member varies. In another non-limiting configuration, one or more of the axial longitudinal member segments that are located closer to a top portion of the frame have a thickness, width, and/or cross-sectional area that is less than a thickness, width and/or cross-sectional area of one or more of the axial longitudinal member segments that are located below the axial longitudinal member segments that are located closer to a top portion of the frame. In another on-limiting embodiment, when the axial longitudinal member is formed of two or more axial longitudinal member segments, the longitudinal length of the axial longitudinal member segments can be the same or different. In one non-limiting configuration, the axial longitudinal members that are formed of two or more axial longitudinal member segments have two or more of the axial longitudinal member segments being different longitudinal lengths.

In accordance with another and/or alternative non-limiting aspect of the present disclosure, the prosthetic heart valve includes a radially collapsible and expandable frame that includes a plurality of the angular articulating members. In one non-limiting embodiment, the frame includes at least two rows (e.g., 2-12 and all values and ranges therebetween) of angular articulating members. In another non-limiting embodiment, the shape, size, and/or configuration of a plurality or a majority or all of the angular articulating members on each row of angular articulating members are the same. In one non-limiting configuration, the shape, size, and configuration of all of the angular articulating members on one or more rows of angular articulating members are the same. In another no-limiting configuration, the shape, size, and configuration of some of the angular articulating members on a row of angular articulating members are different from other angular articulating members on the same row of angular articulating members.

In accordance with another and/or alternative non-limiting aspect of the present disclosure, the prosthetic heart valve includes a radially collapsible and expandable frame that includes a plurality of the angular articulating members wherein a plurality, a majority or all of the angular articulating members are formed of a centrally located arcuate portion or semi-circular portion, and first and second arms that extend from each side of the semi-circular portion. In one non-limiting embodiment, each of the first and second arms include one or more undulations. In another non-limiting embodiment, the longitudinal length of one or both arms is greater than a width of the semi-circular portion. In another non-limiting configuration, the combined longitudinal length of the two arms constitutes at least 60% (e.g., 60-95% and all values and ranges therebetween) of the total longitudinal length of the angular articulating members. In another non-limiting embodiment, a plurality of the angular articulating members has first and second arms that are the same length, size, shape, and/or configuration. In one non-limiting configuration, a plurality of the angular articulating members has first and second arms that are the same length, size, shape, and configuration. In one non-limiting configuration, a plurality of the angular articulating members has first and second arms that are not the same length, size, shape, and/or configuration. In another non-limiting configuration, the semi-circular portion has an arc length of 60-190° (and all values and ranges therebetween) when the frame is in the expanded orientation, and the semi-circular portion has an arc length of 80-340° (and all values and ranges therebetween) when the frame is in the crimped or collapsed orientation.

In accordance with another and/or alternative non-limiting aspect of the present disclosure, the prosthetic heart valve includes a radially collapsible and expandable frame that includes three or more rows of the angular articulating members and wherein the spacing of the angular articulating members between adjacently positioned rows of angular articulating members can be the same or different.

In accordance with another and/or alternative non-limiting aspect of the present disclosure, the prosthetic heart valve includes a radially collapsible and expandable frame that includes one or more frame opening arrangements that can optionally be used as securing locations for the one of more leaflet structures, leaflet, inner skirt, and/or outer skirt. In one non-limiting embodiment, one or more of the frame opening arrangements includes a first and optionally a second frame opening. The size and shape of the lower frame opening and optional an upper frame opening are non-limiting. In one non-limiting configuration, the one or more optional upper frame openings can be used as a marker to facilitate in the proper positioning of the frame and prosthetic heart valve in the heart.

In accordance with another and/or alternative non-limiting aspect of the present disclosure, the prosthetic heart valve includes a radially collapsible and expandable frame that includes one or more of the following features: a) high radial strength after expansion of the frame, b) small crimp profile; c) use of a material that minimal recoil after expansion of the frame; d) little or no longitudinal foreshortening of the frame during expansion; e) smooth curvature at peaks and along angular articulating members and/or the axial longitudinal members of the frame; f) symmetrical design for restoration of valve function and visualization of frame; g) markers on frame for commissural alignment; and/or h) open cell aligned with coronary for hemodynamic and reintervention.

One non-limiting object of the present disclosure is the provision of the refractory metal alloy or a metal alloy that includes at least 5 awt. % (e.g., 5-99 awt. % and all values and ranges therebetween) rhenium that can be used to partially or fully form a frame of a prosthetic heart valve.

Another and/or alternative non-limiting object of the present disclosure is the provision of a prosthetic heart valve that includes a frame that is partially or fully formed of refractory metal alloy or a metal alloy that includes at least 5 awt. % (e.g., 5-99 awt. % and all values and ranges therebetween) rhenium and which prosthetic heart valve has improved procedural success rates.

Another and/or alternative non-limiting object of the present disclosure is the provision of a prosthetic heart valve that includes a frame has a novel geometry in combination with the frame being partially or fully formed of the rhenium containing alloy to enable the formation of a frame that a) has an open cell geometry in the frame of the prosthetic heart valve that can be used to reduce delivery system size reducing vascular and neurological complications, b) with high radial strength using an open cell pattern due to the high yield strength and ultimate tensile strength of the rhenium containing metal alloy, c) having improved restoration of the physiologic EOA in challenging, heavily calcified valves that exert high force on the bioprosthetic valve, while allowing a reduced crimp diameter for vascular access, d) has improved restoration of the physiologic EOA that results in greater longevity of the bioprosthetic valve, c) that includes a material having lower recoil than the traditional materials of stainless steel, chromium-cobalt, or titanium alloys resulting in less recoil of the frame when expanded which leads to decreased risk of valve embolization, decreased paravalvular leak due to improved conformability of the native anatomy, more accurate restoration of the physiologic EOA, and decrease conduction system injury due to a lower balloon inflation diameter required to obtain the physiologic EOA after balloon inflation, f) having an open cell geometry that allows for a frame geometry with no longitudinal foreshortening, which allows for more accurate placement of the valve in the native annulus, since a frame with no longitudinal foreshortening has a shorter initial frame length allowing for a shorter balloon, which decreases conduction system injury, g) having an open cell geometry with commissural alignment markers and an open cell between the commissures that allows for proper placement of the bioprosthetic valve in relation to the native commissures of the valve for proper hemodynamic function in regard to wash out of the valve and blood flow to the coronaries, which leads to better durability and longevity of the valve, and access and re-intervention of the coronaries preventing future adverse events, h) having an open cell geometry with radial symmetry, longitudinal symmetry, and no longitudinal foreshortening allows for symmetrical and cylindrical expansion of the prosthetic valve resulting in lower rates of leaflet thrombosis and structural valve deterioration, and i) is formed of a rhenium containing metal alloy with no nickel content that prevents allergic response due to the presence of nickel and restenosis associated with nickel content.

Another and/or alternative non-limiting object of the present disclosure is the provision of a prosthetic heart valve for implantation into a heart; the prosthetic heart valve includes an expandable metal frame, a leaflet structure supported by the expandable metal frame, and an inner skirt secured to the expandable metal frame; the expandable metal frame is configured to expand from a crimped orientation to an expanded orientation when the prosthetic heart valve is positioned in a treatment site in the heart; the expandable metal frame includes a plurality of angular articulating members and a plurality of axial longitudinal members; the angular articulating members and the axial longitudinal members are connected together to form a plurality of cells in the expandable metal frame organized into rows whereby the rows of cells are connected by axial longitudinal members; one or more of the axial longitudinal members have a longitudinal length that is at least 10% a longitudinal length of the expandable metal frame when the expandable metal frame is in the expanded orientation.

Another and/or alternative non-limiting object of the present disclosure is the provision of a prosthetic heart valve for implantation into a heart wherein the leaflet structure comprises a plurality of leaflets, each of the leaflets has an upper edge portion, a lower edge portion and two side flaps, wherein each side flap is connected to an adjacent side flap of another leaflet, at least a portion of the leaflet structure connected to the expandable metal frame.

Another and/or alternative non-limiting object of the present disclosure is the provision of a prosthetic heart valve for implantation into a heart wherein the leaflet structure is attached to the expandable metal frame using a plurality of sutures, staples or adhesive.

Another and/or alternative non-limiting object of the present disclosure is the provision of a prosthetic heart valve for implantation into a heart that includes an expandable metal frame and at least one leaflet that is connected to the expandable metal frame; the expandable metal frame is configured to be crimped and further expand from a crimped orientation to an expanded orientation opening in a body passageway; the expandable metal frame has distal and proximal ends; the expandable metal frame a) has an open cell configuration that includes a plurality of frame cells and wherein the open cell configuration has high radial strength, b) is formed of a material that has reduced recoil thus resulting in reduced recoil of the frame when expanded, and c) can be crimped a small diameter; the expandable metal frame has one or more of the following properties: i) has a yield strength of at least 110 ksi, ii) has a modulus of elasticity of at least 52000 ksi, iii) has a frame geometry that has a maximum of 9 frame cells per horizontal row, wherein horizontal is defined as perpendicular to a longitudinal axis of the expandable metal frame, iv) that is at least partially formed of a rhenium containing metal alloy that includes at least 0.1 wt. % rhenium, v) that is at least partially formed of a rhenium containing metal alloy that includes 0.1-70 wt. % rhenium and one or more metals selected from the group consisting of Mo, Cr, Co, Ni, Ti, Ta, Nb, Zr, and W, vi) is formed of material that has a reduced recoil when bend such that the expandable frame has no more than 5% recoil when the expandable metal frame is plastically deformed, vii) has longitudinal foreshortening of no more than 20% when the expandable metal frame is plastically deformed (e.g., the longitudinal length of the expanded frame reduces in longitudinal length of 0-20% and all values and ranges therebetween when the expandable frame is crimped or when the expandable frame is expanded from the crimped positioned to the expanded position), viii) that is at least partially formed of a rhenium containing metal alloy that has an elongation of at least 20%, and/or ix) has a frame geometry that has frame cells with only at least 5 vertices per frame cell.

Another and/or alternative non-limiting object of the present disclosure is the provision of a prosthetic heart valve for implantation into a heart that wherein one or more of the frame cells includes at least two axial longitudinal members, and at least two angular articulating member pairs; each of the angular articulating member pairs includes at least two angular articulating members connected by an articulating joint; at least one of the axial longitudinal members extends from the distal end to the proximal end of the expandable frame; and wherein during expansion and/or crimping of the expandable frame, an frame an overall longitudinal length of the frame cell does not exceed a longitudinal length of the axial longitudinal members.

Another and/or alternative non-limiting object of the present disclosure is the provision of a prosthetic heart valve comprising an expandable metal frame and at least one leaflet that is connected to the expandable metal frame; the expandable metal frame is configured to be crimped and further expand from a crimped orientation to an expanded orientation opening in a body passageway; the expandable metal frame has distal and proximal ends; the expandable metal frame includes a) an open cell configuration that includes a plurality of frame cells and at least two rows of frame cells, and/or b) is formed of a material that has a recoil of less than 6% thus resulting in reduced recoil of the expandable metal frame when expanded from the crimped orientation to the expanded orientation; the expandable metal frame has two or more of the following properties: i) at least 70-100% of the expandable metal frame is formed of a metal alloy that has a yield strength of at least 110 ksi, ii) at least 70-100% of the expandable metal frame is formed of a metal alloy that has a modulus of elasticity of at least 35000 ksi, iii) a frame geometry that has a maximum of nine frame cells per horizontal row, iv) at least 70-100% of the expandable metal frame is formed of a metal alloy that is formed of a rhenium containing metal alloy that includes at least 0.1 wt. % rhenium and one or more metals selected from the group consisting of Mo, Cr, Co, Ni, Ti, Ta, Nb, Zr, and W, v) the expandable metal frame is formed of material that has a recoil of no more than 5% recoil when the expandable metal frame is plastically deformed, vi) the expandable metal frame has a longitudinal foreshortening of no more than 20% when the expandable metal frame is plastically deformed, vii) the expandable metal frame is formed of a metal alloy that has an elongation of at least 20%, and/or viii) each of the cells includes at least one axial longitudinal member and at least two angular articulating members, and wherein each of the angular articulating members includes a plurality of arcuate portions along a longitudinal length of the angular articulating member, and wherein one or more of the axial longitudinal members has a continuous linear shape of at least 80% of a longitudinal length of the axial longitudinal member.

Another and/or alternative non-limiting object of the present disclosure is the provision of a prosthetic heart valve wherein one or more of the frame cells includes at least two axial longitudinal members and at least two angular articulating members; each of the angular articulating members includes first and second arms that are connected to an articulating joint; the an articulating joint having an arcuate shape or semi-circular portion; each of the axial longitudinal member has a continuous linear shape of at least 90% of a longitudinal length of the axial longitudinal member.

Another and/or alternative non-limiting object of the present disclosure is the provision of a prosthetic heart valve wherein at least one axial longitudinal member in the row of frame cells is aligned along a same longitudinal axis to form an aligned group of axial longitudinal members and the aligned group of axial longitudinal members fully extends from the distal end to the proximal end of the expandable metal frame; and wherein during expansion and/or crimping of the expandable metal frame an overall longitudinal length of each of the frame cells in a row of frame cells does not exceed the longitudinal length of each of the axial longitudinal members in the frame cell.

Another and/or alternative non-limiting object of the present disclosure is the provision of a prosthetic heart valve wherein one or more of the angular articulating members include one or more independent radii across their longitudinal length.

Another and/or alternative non-limiting object of the present disclosure is the provision of a prosthetic heart valve wherein a sum of longitudinal lengths of the angular articulating members is greater than or equal a sum of longitudinal lengths of the axial longitudinal members.

Another and/or alternative non-limiting object of the present disclosure is the provision of a prosthetic heart valve wherein a longitudinal length of the expandable frame is equivalent to the longitudinal length of at least one of the group of aligned axial longitudinal members during expansion and crimping of the expandable frame.

Another and/or alternative non-limiting object of the present disclosure is the provision of a prosthetic heart valve wherein a longitudinal length between the proximal end of the expandable frame and a commissural attachment area on the expandable frame is constant during expansion and/or crimping of the expandable frame.

Another and/or alternative non-limiting object of the present disclosure is the provision of a prosthetic heart valve further including a commissural alignment marker that is positioned in the expandable frame; the commissural alignment marker formed of a same material as the material used to form the expandable frame.

Another and/or alternative non-limiting object of the present disclosure is the provision of a prosthetic heart valve wherein the angular articulating members in the frame cells in a same column and/or same row of frame cells are of a same longitudinal length.

Another and/or alternative non-limiting object of the present disclosure is the provision of a prosthetic heart valve wherein vertices of adjacently positioned frame cells in adjacent rows are aligned to within no more than 5% of a total longitudinal length of the angular articulating members.

Another and/or alternative non-limiting object of the present disclosure is the provision of a prosthetic heart valve wherein an area of each of a most distal row of frame cells and an area of each of a most proximal end of frame cells on the expandable frame does not differ by more than 20%.

Another and/or alternative non-limiting object of the present disclosure is the provision of a prosthetic heart valve wherein the material of the expandable frame is at least partially made out of a metal alloy that includes less than 1 wt. % nickel and/or less than 0.1 wt. % cobalt.

Another and/or alternative non-limiting object of the present disclosure is the provision of a prosthetic heart valve wherein the expandable metal frame includes a plurality of angular articulating members and a plurality of axial longitudinal members; the angular articulating members and the axial longitudinal members are connected together to form a plurality of cells in the expandable metal frame that are organized into rows; each of the cells includes at least one the axial longitudinal members and at least two angular articulating members; each of the angular articulating members includes a plurality of arcuate portions along a longitudinal length of the angular articulating member; one or more of the axial longitudinal members has a continuous linear shape of at least 80% of a longitudinal length of the axial longitudinal member; the expandable metal frame has a longitudinal foreshortening of no more than 20% when the expandable metal frame is plastically deformed.

Another and/or alternative non-limiting object of the present disclosure is the provision of a prosthetic heart valve wherein one or more of the axial longitudinal members have a longitudinal length that is 70-100% of the longitudinal length of the expandable metal frame when the expandable metal frame is in the expanded orientation.

Another and/or alternative non-limiting object of the present disclosure is the provision of a prosthetic heart valve wherein the expandable metal frame includes a first cell row, a second cell row, and a third cell row; each of the first, second, and third cell rows includes a plurality of angular articulating members; each of the angular articulating members in the first cell row includes first and second ends, and wherein the first end of each of the angular articulating members is connected to one of the axial longitudinal members and the second end of each of the angular articulating members is connected to a different axial longitudinal member; each of the angular articulating members in the second cell row includes first and second ends, and wherein a plurality or all of the first ends of a plurality or all of the angular articulating members is connected to one of the axial longitudinal members and a plurality or all of the second ends of a plurality or all of the angular articulating members is connected to a different axial longitudinal member; each of the angular articulating members in the third cell row includes first and second ends, and wherein a plurality or all of the first ends of a plurality or all of the angular articulating members is connected to one of the axial longitudinal members and a plurality or all of the second ends of a plurality or all of the angular articulating members is connected to a different axial longitudinal member; the angular articulating members in the first cell row are all spaced from the angular articulating members in the second and third cell rows when the expandable metal frame is in the expanded orientation; the angular articulating members in the second cell row are all spaced from the angular articulating members in the third cell row when the expandable metal frame is in the expanded orientation.

Another and/or alternative non-limiting object of the present disclosure is the provision of a prosthetic heart valve wherein the expandable metal frame includes a fourth cell row; the fourth cell row includes a plurality of angular articulating members; each of the angular articulating members in the first cell row includes first and second ends, and wherein a plurality or all of the first ends of each of the angular articulating members is connected to one of the axial longitudinal members and a plurality or all of the second ends of each of the angular articulating members is connected to a different axial longitudinal member; the angular articulating members in the fourth cell row are all spaced from the angular articulating members in the first, second and third cell rows when the expandable metal frame is in the expanded orientation.

Another and/or alternative non-limiting object of the present disclosure is the provision of a prosthetic heart valve wherein a plurality of the axial longitudinal members includes first and second axial longitudinal member segments; a longitudinal length of the first and second axial longitudinal member segments is different; each of the first and second axial longitudinal member segments includes top and bottom ends; the top end of each of the first axial longitudinal member segment is connected to a) a bottom end of the second axial longitudinal member segment and b) two of the angular articulating members; the top end of the second end of each of the second axial longitudinal member segment is connected to two of the angular articulating members and/or a bottom portion of one of the frame opening arrangements.

Another and/or alternative non-limiting object of the present disclosure is the provision of a prosthetic heart valve wherein a plurality of the axial longitudinal members includes a third axial longitudinal member segments; a longitudinal length of the third axial longitudinal member segment is different from a longitudinal length of the first and/or second axial longitudinal member segments; the third axial longitudinal member segment includes top and bottom ends; the bottom end of each of the third axial longitudinal member segment is connected to a) a top end of the second axial longitudinal member segment and/or b) two of the angular articulating members; the top end of the third end of each of the second axial longitudinal member segment is connected to two of the angular articulating members.

Another and/or alternative non-limiting object of the present disclosure is the provision of a prosthetic heart valve wherein each of the angular articulating members includes a centrally located arcuate portion and first and second arms that extend from each side of arcuate portion; the first arm on each of the angular articulating members has a first arm end; the second arm on each of the angular articulating members has a second arm end; each of the first arm ends connected to a) one of the one of the axial longitudinal members and/or b) one of the frame opening arrangements; a longitudinal length of one or both first and second arms of each of the angular articulating members is greater than a width or longitudinal length of the semi-circular portion.

Another and/or alternative non-limiting object of the present disclosure is the provision of a prosthetic heart valve wherein each of the first and second arms includes one to three undulations.

Another and/or alternative non-limiting object of the present disclosure is the provision of a prosthetic heart valve wherein the expandable metal frame is partially or fully formed of a refractory metal alloy or a metal alloy that includes at least 15 awt. % rhenium or the refractory metal alloy or the metal alloy that includes at least 5 awt. % rhenium; and wherein the metal alloy is not a shape memory alloy.

Another and/or alternative non-limiting object of the present disclosure is the provision of a prosthetic heart valve wherein the expandable metal frame has a) is formed of material that has a reduced recoil when bend such that the expandable frame has no more than 5% recoil when the expandable metal frame is crimped to a crimped state, b) is formed of material that has a reduced recoil when bend such that the expandable frame has no more than 5% recoil when the expandable metal frame is expanded from a crimped state to an expanded state, and/or c) a longitudinal foreshortening percentage of less than 20% when the expandable metal frame is expanded from the crimped state.

Another and/or alternative non-limiting object of the present disclosure is the provision of an expandable prosthetic heart valve comprising an expandable metal frame for implantation into a body passageway; said expandable metal frame is configured to be crimped and expanded from a crimped orientation to an expanded orientation in an opening in the body passageway; said expandable metal frame has distal and proximal ends; said expandable metal frame includes a plurality of frame cells and at least two rows of frame cells; said expandable metal frame has two or more of the following properties: i) at least 70-100% of said expandable metal frame is formed of a metal alloy that has a yield strength of at least 110 ksi, ii) at least 70-100% of said expandable metal frame is formed of a metal alloy that has a modulus of elasticity of at least 35000 ksi, iii) at least 70-100% of said expandable metal frame is formed of a metal alloy that is formed of a rhenium containing metal alloy that includes at least 0.1 wt. % rhenium and one or more metals selected from the group consisting of Mo, Cr, Co, Ni, Ti, Ta, Nb, Zr, and W, iv) said expandable metal frame is formed of material that has a recoil of no more than 10% recoil when said expandable metal frame is plastically deformed, v) said expandable metal frame has a longitudinal foreshortening of no more than 20% when said expandable metal frame is plastically deformed, vi) each of said cells includes at least one axial longitudinal member and at least two angular articulating members, and wherein each of said angular articulating members includes a plurality of arcuate portions along a longitudinal length of said angular articulating member, and/or vii) vi) each of said cells includes at least one axial longitudinal member and at least two angular articulating members, and wherein each of said angular articulating members includes a plurality of arcuate portions along a longitudinal length of said angular articulating member, and wherein one or more of said axial longitudinal members has a continuous linear shape of at least 80% of a longitudinal length of said axial longitudinal member; and wherein one or more of said frame cells optionally includes at least two axial longitudinal members and at least two angular articulating members; each of said angular articulating members includes first and second arms that are connected to an articulating joint; said an articulating joint having an arcuate shape or semi-circular portion; each of said axial longitudinal member has a continuous linear shape of at least 90% of a longitudinal length of said axial longitudinal member; and wherein at least one axial longitudinal member in said row of frame cells is optionally aligned along a same longitudinal axis to form an aligned group of axial longitudinal members and said aligned group of axial longitudinal members fully extends from said distal end to said proximal end of said expandable metal frame; and wherein during expansion and/or crimping of said expandable metal frame an overall longitudinal length of each of said frame cells in a row of frame cells does not exceed said longitudinal length of each of said axial longitudinal members in said frame cell; and wherein one or more of said angular articulating members optionally include one or more independent radii across their longitudinal length; and wherein a sum of longitudinal lengths of said angular articulating members is optionally greater than or equal a sum of longitudinal lengths of said axial longitudinal members; and wherein a longitudinal length of said expandable frame is optionally equivalent to said longitudinal length of at least one of said group of aligned axial longitudinal members during expansion and crimping of said expandable frame; and wherein a longitudinal length between said proximal end of said expandable frame and a commissural attachment area on said expandable frame is optionally constant during expansion and/or crimping of said expandable frame; and wherein the expandable frame optionally includes a commissural alignment marker that is positioned in said expandable frame; said commissural alignment marker formed of a same material as said material used to form said expandable frame; and wherein said material used to form said commissural alignment marker is optionally a metal that has a density of greater than 10 mg/cm$^3$; and wherein said commissural alignment marker is optionally attached to said commissural attachment area; and wherein a most distal row of frame cells on said expandable frame optionally includes has an odd number of frame cells; and wherein said angular articulating members in said frame cells in a same column and/or same row of frame cells are optionally of a same longitudinal length; and wherein vertices of adjacently positioned frame cells in adjacent rows are optionally aligned to within no more than 5% of a total longitudinal length of said angular articulating members; and wherein an area of each of a most distal row of frame cells and an area of each of a most proximal end of frame cells on said expandable frame optionally does not differ by more than 20%; and wherein said material of said expandable frame is made out of a metal alloy that includes less than 1 wt. % nickel and/or less than 0.1 wt. % cobalt; and wherein the expandable frame is optionally formed of a refractory metal alloy or a metal alloy that includes at least 5 atomic weight percent (awt. %) or atomic percent (awt %) rhenium (e.g., 5-99 awt. % rhenium and all values and ranges therebetween); and wherein said frame optionally includes an enhancement layer.

These and other advantages will become apparent to those skilled in the art upon the reading and following of this description.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. Reference may now be made to the drawings, which illustrate various embodiments that the disclosure may take in physical form and in certain parts and arrangement of parts wherein:

FIG. 6C-6E illustrates various features and structures of the TAV frame.

FIG. 7 is a table that lists comparative yield strength and Modulus of various metal alloys.

FIGS. 11A and 11B are illustrations that compares the conformability of a TAV frame formed of refractory metal alloy that is expanded in a non-circular aortic valve that includes calcium deposits to a similar shaped and configured TAV frame formed of CoCr alloy that is expanded in the same non-circular aortic valve, and which illustrates that the paravalvular leak (PVL) about a TAV having a frame formed of CoCr alloy is greater than the PVL about a TAV having a frame formed of refractory metal alloy due the increase conformability of the frame formed of refractory metal alloy as compared to the conformability of the frame formed of CoCr alloy.

DESCRIPTION OF NON-LIMITING EMBODIMENTS OF THE DISCLOSURE

Figure 1B:
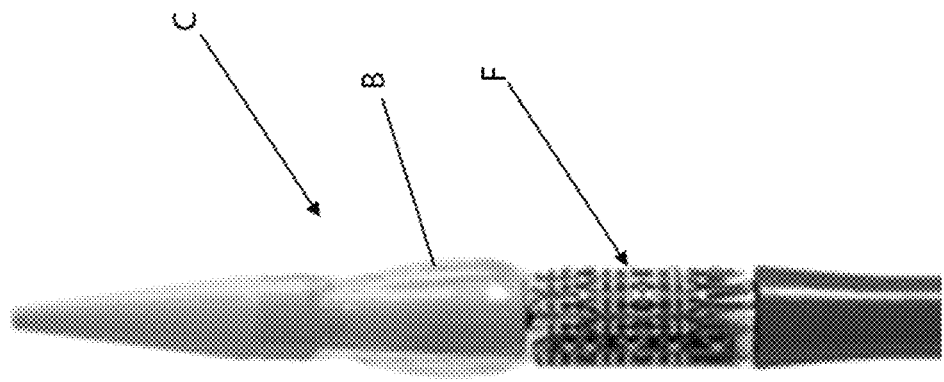
FIG. 1B is a portion of a prior art catheter.

A more complete understanding of the articles/devices, processes and components disclosed herein can be obtained by reference to the accompanying drawings. These figures are merely schematic representations based on convenience and the case of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

Figure 1A:
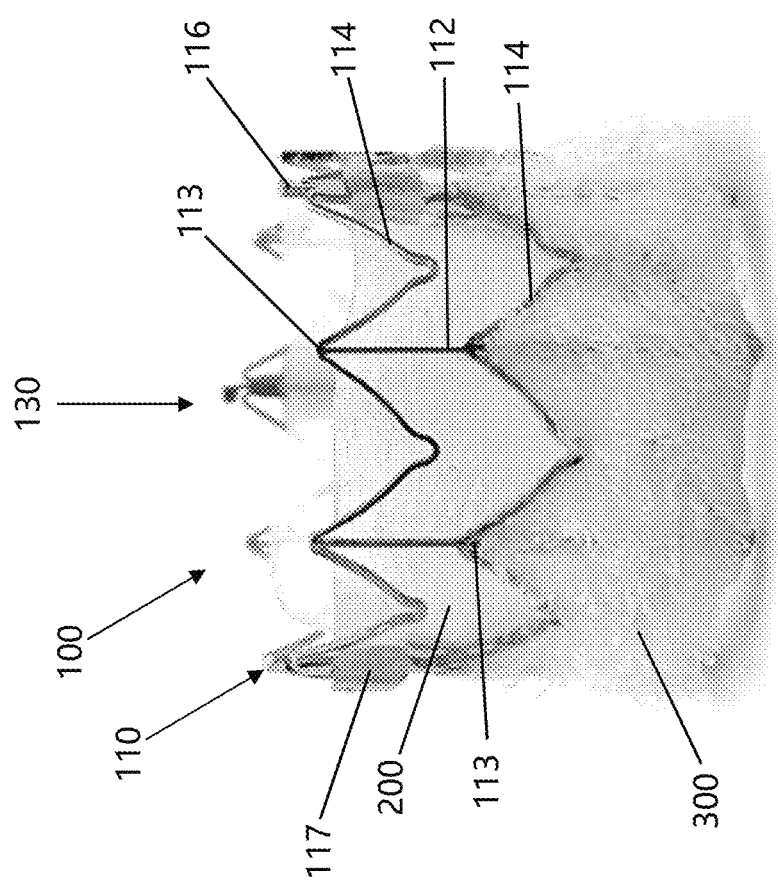
FIG. 1A is an illustration of a TAV in accordance with the present disclosure.

Referring now to FIGS. 1A-IE, these figures are illustrations of an implantable prosthetic heart valve 100 (e.g., TAV) and a method for inserting the prosthetic heart valve 100 in a valve region A (e.g., aortic valve, etc.) of a heart H. Prosthetic heart valve 100 can be implanted in the annulus of native aortic valve A; however, prosthetic heart valve 100 also can be configured to be implanted in other valves of the heart. Although the medical device illustrated is a TAV, the present disclosure is not limited to TAVs or any other heart valve replacement.

Referring now to FIG. 1A, prosthetic heart valve 100 generally comprises a frame 110 formed of a plurality of axial longitudinal members and angular articulating members 112, 114 strut joints 113, leaflet structure 200 supported by frame 110, and an inner skirt 300 secured to the outer surface of frame 110 and/or leaflet structure 200. The frame can include one or more an orientation structures or commissural markers 116. The frame 110 is partially or fully formed of a rhenium containing metal alloy. Prosthetic heart valve 100 has a "lower" end 120 and an "upper" end 130, wherein lower end 120 of prosthetic heart valve 100 is the inflow end and the upper end 130 of prosthetic heart valve 100 is the outflow end.

Frame 110 can be optionally be coated with a polymer material (e.g., silicone, PTFE, ePTFE, polyurethane, polyolefins, hydrogels, biological materials [e.g., pericardium or biological polymers such as collagen, gelatin, or hyaluronic acid derivatives], etc.). The coating can be used to partially or fully encapsulate one or more of the vertically extending axial longitudinal members 112 and/or non-vertically angular articulating members 114 on frame 110 and/or to partially or fully fill-in one or more of the openings between the non-vertically angular articulating members 114 and/or vertically extending axial longitudinal members 112.

The inner skirt 300 can be formed of a variety of flexible materials (e.g., polymer (e.g., polyethylene terephthalate (PET), polyester, nylon, Kevlar, silicon, etc.), composite material, metal, fabric material, etc. In one non-limiting embodiment, the material used to partially or fully form inner skirt 300 can be substantially non-elastic (i.e., substantially non-stretchable and non-compressible). In another non-limiting embodiment, the material used to partially or fully form inner skirt 300 can be a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). Inner skirt 300 can optionally be formed from a combination of a cloth or fabric material that is coated with a flexible material or with a stretchable and/or compressible material so as to provide additional structural integrity to inner skirt 300. The size, configuration, and thickness of inner skirt 300 is non-limiting (e.g., thickness of 0.1-20 mils and all values and ranges therebetween). The inner skirt 300 can be secured to the inside and/or outside of the frame 110 using various means (e.g., sutures, clips, clamp arrangement, etc.).

Inner skirt 300 can be used to 1) at least partially seal and/or prevent perivalvular leakage, 2) at least partially secure leaflet structure 200 to frame 110, 3) at least partially protect one or more of the leaflets of leaflet structure 200 from damage during the crimping process of prosthetic heart valve 100, 4) at least partially protect one or more of the leaflets of leaflet structure 200 form damage during the operation of prosthetic heart valve 100 in heart H.

Prosthetic heart valve 100 can optionally include an outer skirt or sleeve (not shown) that is positioned at least partially about the exterior region of frame 110. The outer skirt or sleeve (when used) generally is positioned completely around a portion of the outside of frame 110. Generally, the outer skirt is positioned about the lower portion of frame 110 and does not fully cover the upper portion of frame 110; however, this is not required. The outer skirt can be connected to frame 110 by a variety of arrangements (e.g., sutures, adhesive, melted connection, clamping arrangement, etc.). At least a portion of the outer skirt can optionally be located on the interior surface of frame 110; however, this is not required. Generally, the outer skirt is formed of a more flexible and/or compressible material than inner skirt 300; however, this is not required. The outer skirt can be formed of a variety of a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The outer skirt can optionally be formed from a combination of a cloth or fabric material that is coated with the stretchable and/or compressible material so as to provide additional structural integrity to the outer skirt. The size, configuration, and thickness of the outer skirt is non-limiting. The thickness of the outer skirt is generally 0.1-20 mils (and all values and ranges therebetween).

Leaflet structure 200 can be can be attached to frame 110 and/or inner skirt 300. The connection arrangement used to secure leaflet structure 200 to frame 110 and/or inner skirt 300 is non-limiting (e.g., sutures, melted bold, adhesive, clamp arrangement, etc.). The material used to form the one or more leaflets of leaflet structure 200 include, but are not limited to, bovine pericardial tissue, biocompatible synthetic materials, or various other suitable natural or synthetic materials.

Leaflet structure 200 can be comprised of two or more leaflets (e.g., 2, 3, 4, 5, 6, etc.). In one non-limiting arrangement, leaflet structure 200 includes three leaflets that are arranged to collapse in a tricuspid arrangement. The size, shape and configuration of the one or more leaflets of leaflet structure 200 are non-limiting. In one non-limiting arrangement, the leaflets have generally the same shape, size, configuration and thickness.

Two of more of the leaflets of leaflet structure 200 can optionally be secured to one another at their adjacent sides to form commissures of leaflet structure 200 (the edges where the leaflets come together). Leaflet structure 200 can be secured to frame 110 and/or inner skirt 300 by a variety of connection arrangement (e.g., sutures, adhesive, melted bond, clamping arrangement, etc.).

One or more leaflets of the leaflet structure 200 can optionally include reinforcing structures or strips to 1) facilitate in securing the leaflets together, 2) facilitate in securing the leaflets to the inner skirt 300 and/or frame 110, and/or 3) inhibit or prevent tearing or other types of damage to the leaflets.

Prosthetic heart valve 100 is configured to be radially collapsible to a collapsed or crimped state for introduction into the body on a delivery catheter (FIG. 1B) and radially expandable to an expanded state for implanting prosthetic heart valve 100 at a desired location in heart H (e.g., aortic valve A, etc.) (FIG. 1E). The frame of prosthetic heart valve 100 is made of a plastically-expandable material (e.g., refractory metal alloy) that permits crimping of the frame to a smaller profile for delivery and expansion of prosthetic heart valve 100 using an expansion device. FIG. 1B illustrates a generic frame F of a prosthetic heart valve that is crimped on a generic balloon catheter C. The balloon B on the balloon catheter C can be used to expand the frame F from a crimped state to an expanded state. Various type of crimping apparatus and techniques can be used to crimp the prosthetic heart valve on the balloon delivery catheter. The process of crimping a prosthetic heart valve using a crimping device is known in the art and will not be described herein. During a crimping procedure, damage to leaflets of leaflet structure should be avoided.

Figure 1D:
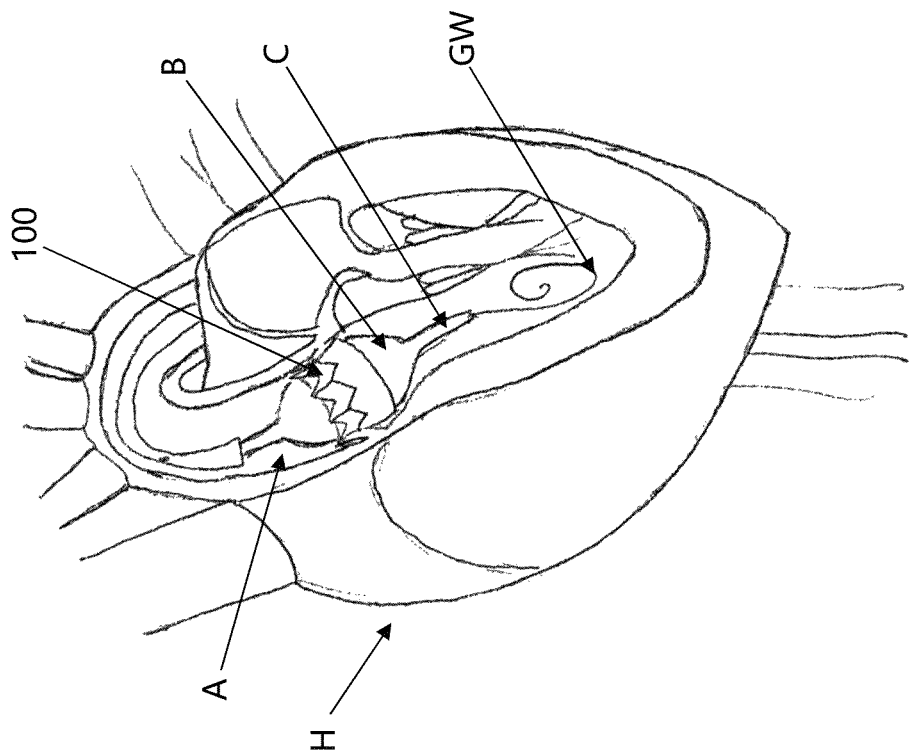
FIGS. 1C-1E illustrate a typical TAVR procedure for inserting the TAV into a valve of a heart.
Figure 1C:
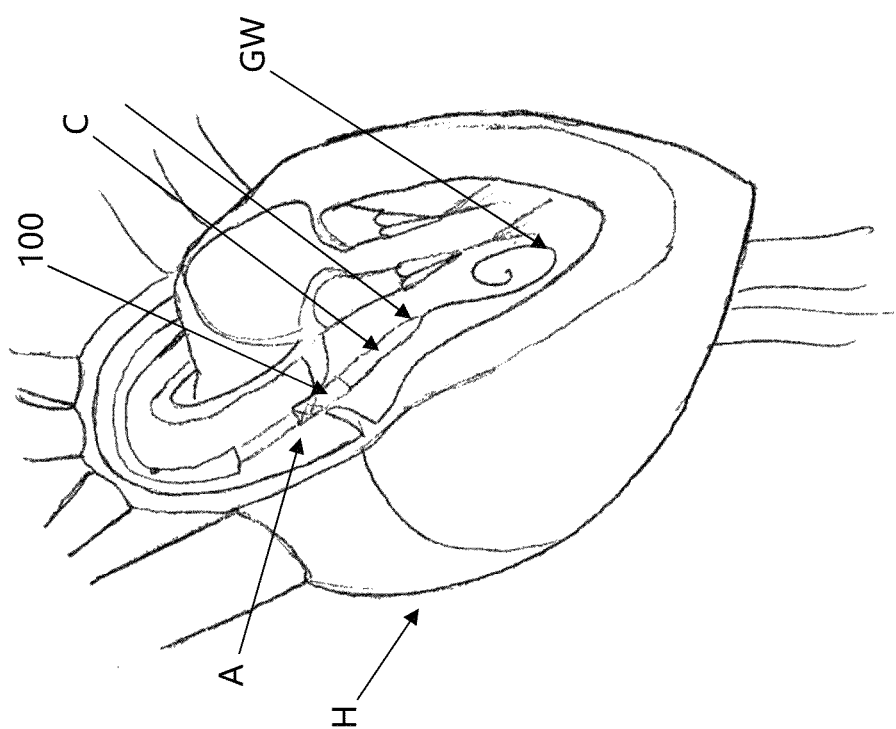
Figure 1E:
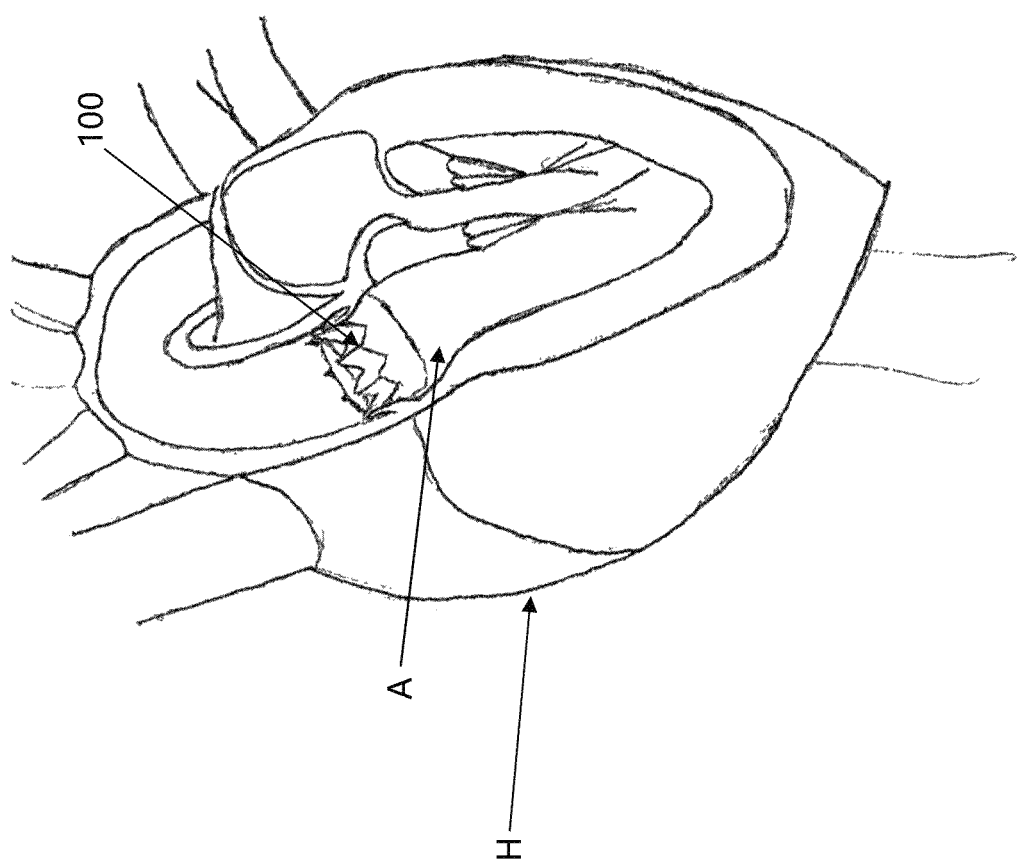
Figure 2:
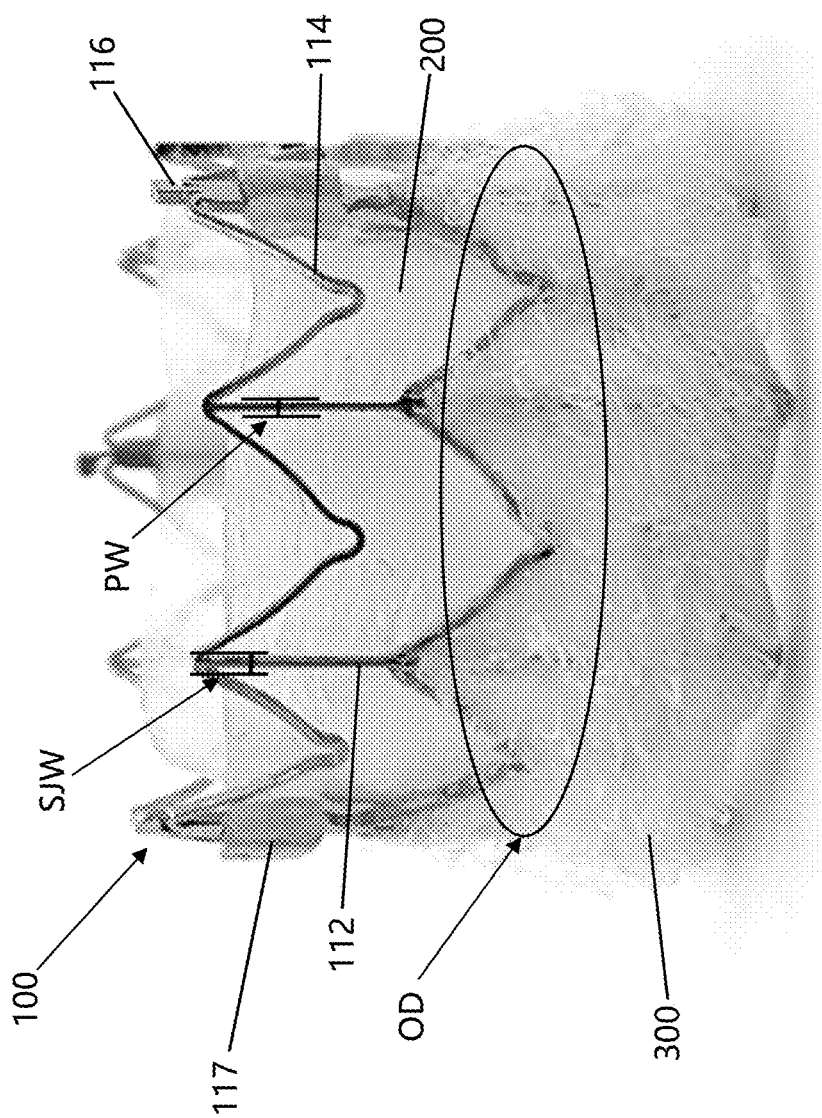
FIG. 2 is an illustration of the TAV of FIG. 1A illustrating features of the axial longitudinal members and the angular articulating members of the frame.

As illustrated in FIGS. 1C-1E, once prosthetic heart valve 100 is crimped on balloon B of a balloon catheter C, balloon catheter C is inserted through a blood vessel and to the location in heart H wherein prosthetic heart valve 100 is to be deployed (See FIG. 1C). At the treatment location, the balloon B on balloon catheter C is expanded to thereby cause prosthetic heart valve 100 to be expanded and secured in a valve region A of heart H (See FIG. 1D). Thereafter, balloon B is deflated and balloon catheter C is removed from the patient (See FIG. 1E).

Referring now to FIGS. 3-6E, a novel frame 400 for prosthetic heart valve 100 is illustrated. Frame 400 configured to be crimped onto a delivery catheter C so that crimped prosthetic heart valve 100 can be inserted in a heart valve. Frame 400 can optionally be configured to enable prosthetic heart valve 100 to be crimped to a diameter that is less than 22 Fr; however, this is not required. As such, prosthetic heart valve 100 that includes frame 400 in accordance with the present disclosure can optionally be configured to enable a prosthetic heart valve 100 to be inserted into smaller sized heart valves that could not previously be treated with prior art prosthetic heart valves. As can be appreciated, prosthetic heart valve 100 in accordance with the present disclosure can be sized and configured to be inserted in heart valves that are larger than 22 Fr.

Figure 3:
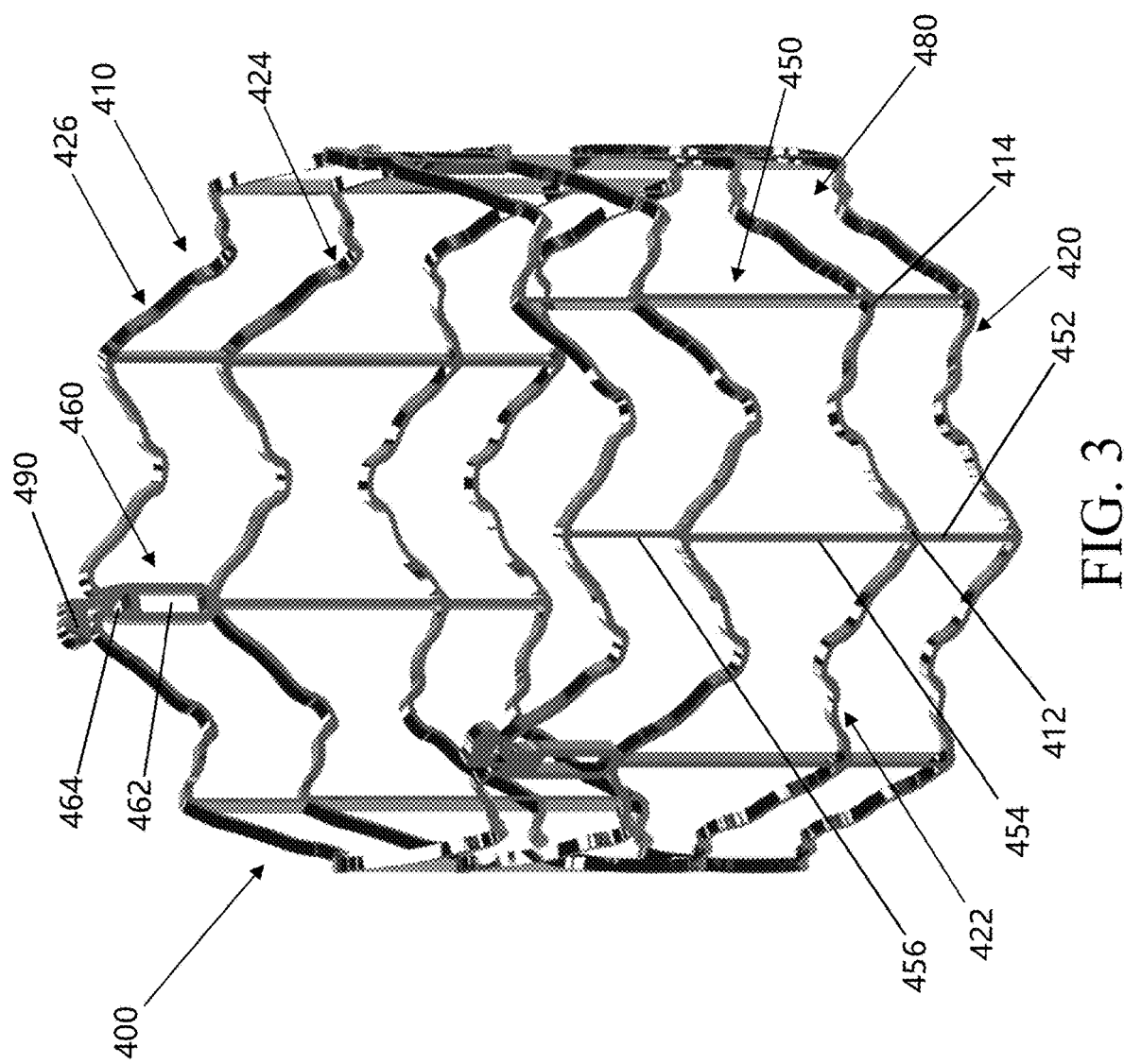
FIG. 3 is a front elevation view of a frame of a TAV in the expanded state in accordance with the present disclosure.
Figure 4:
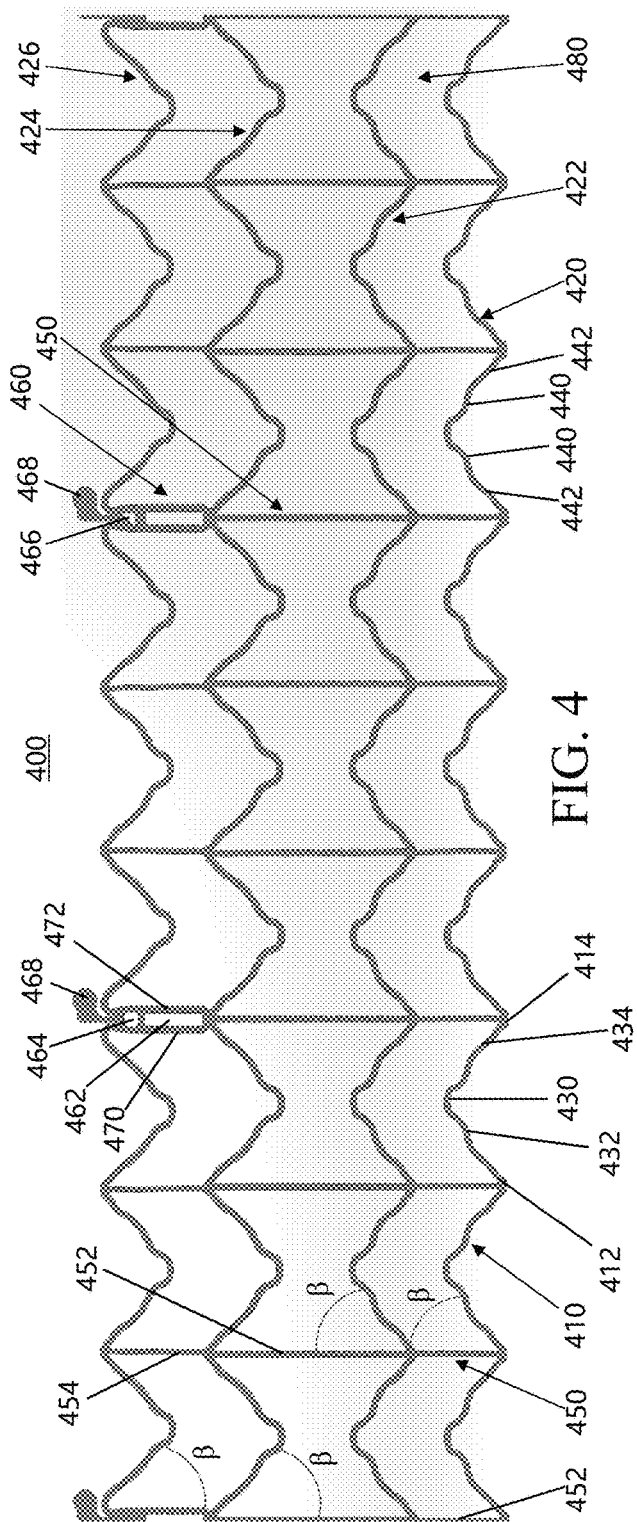
FIG. 4 is a front view of a flat frame of a TAV in the expanded state in accordance with the present disclosure.
Figure 5:
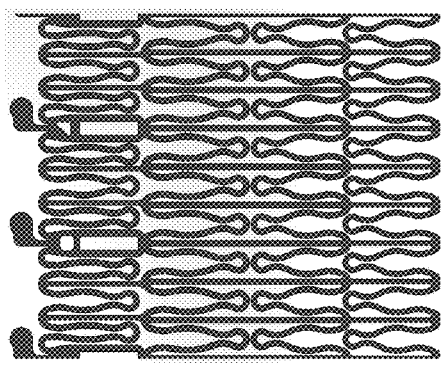
FIG. 5 is a front view of a flat frame of a TAV in the crimped or unexpanded state in accordance with the present disclosure.

Referring now to FIGS. 3-5, one non-limiting embodiment of a frame 400 in accordance with the present disclosure is illustrated. FIGS. 6A-6E illustrates another non-limiting embodiment of a frame 400 in accordance with the present disclosure. As will be discussed in more detail below, frame 400 illustrated in FIGS. 3-5 includes four rows of angular articulating members 410 and sets of cells that include nine cells 480, and frame 400 illustrated in FIGS. 6A-6E includes three rows of angular articulating members 410 and sets of cells that include six cells 480.

Referring again to FIGS. 3-5, the radially collapsible and expandable frame 400 includes plurality of angular articulating members 410, a plurality of axial longitudinal members 450, and a plurality of frame opening arrangements 460, and wherein angular articulating members 410, the plurality of axial longitudinal members 450, and frame opening arrangements 460 are connected together to form a plurality of cells 480 in frame 400. The region that includes the frame opening arrangements 460 is referred to as the commissural attachment area. Connected to the top region of the commissural attachment area can optionally include a top marker or orientation structure or commissural alignment marker 468.

The angular articulating members 410 have first and second ends 412, 414 that are connected to axial longitudinal members 450 or frame opening arrangements 460.

Frame opening arrangements 460 are located on the top portion of frame 400. Each of frame opening arrangements 460 can include a lower frame opening 462 and an optional an upper frame opening 464, 466.

Figure 6A:
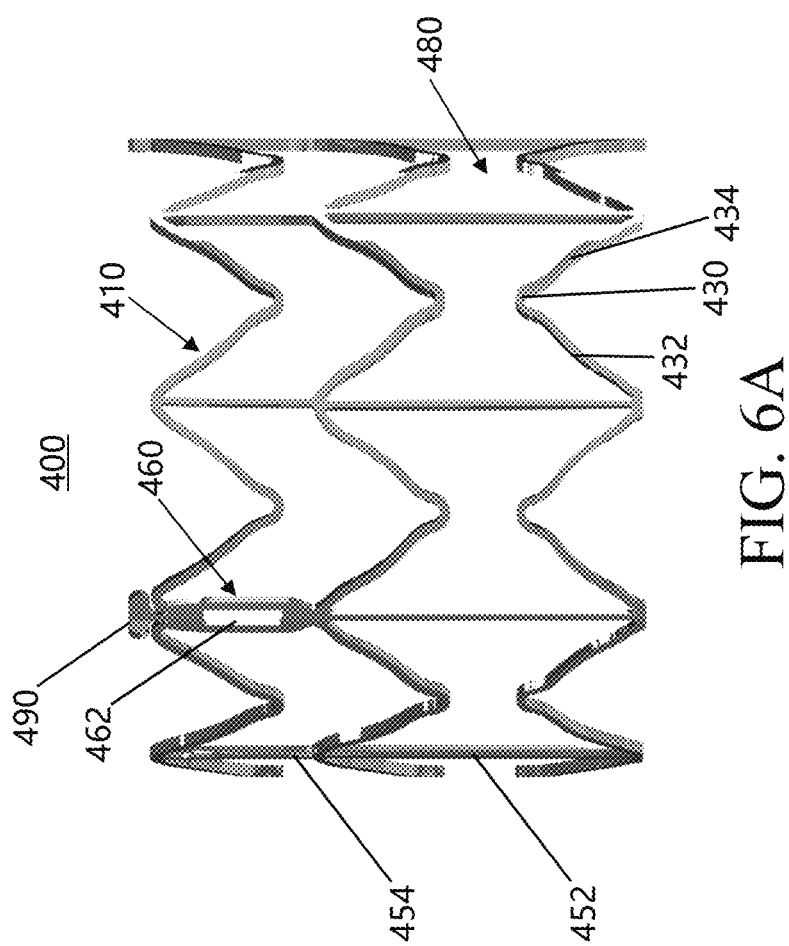
FIG. 6A is a front view of another flat frame of a TAV in the expanded state in accordance with the present disclosure.
Figure 6B:
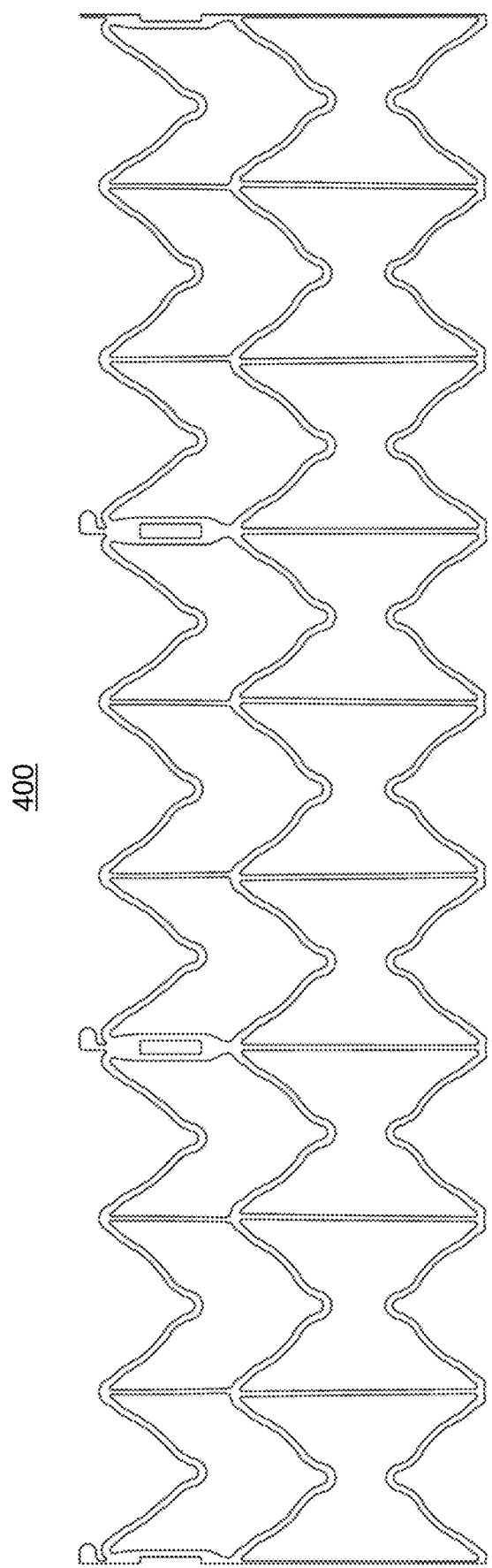
FIG. 6B is a front view of a flat frame in the expanded state of FIG. 6A that includes non-limiting dimensions of the frame.
Figure 6C:
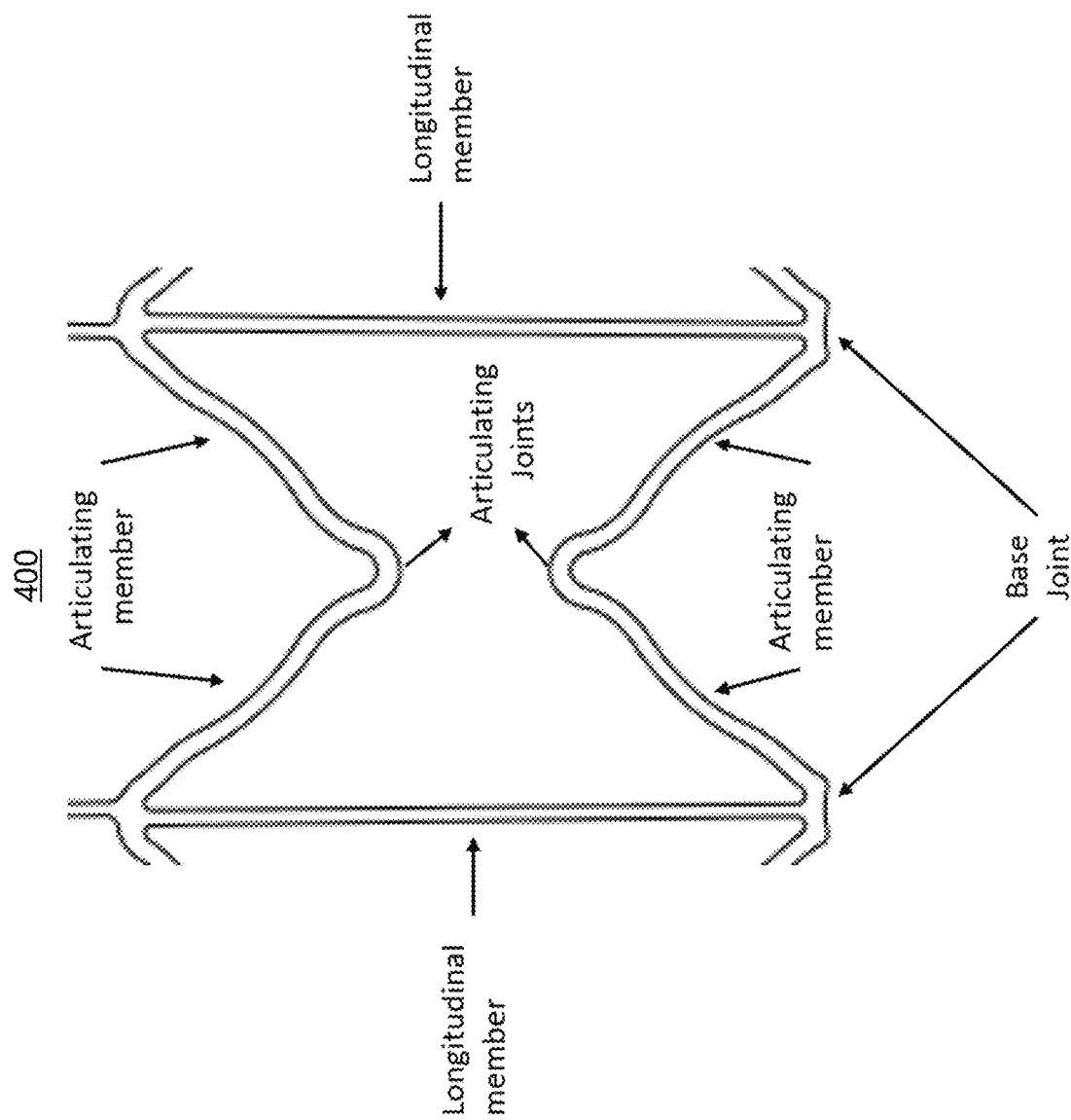

As illustrated in FIG. 4, frame 400 is formed of three sets of cells, wherein each set of cells includes nine cells 480. As illustrated in FIGS. 6A and 6B, frame includes two sets of cells, and wherein each set of cells includes nine cells. As illustrated in FIG. 4, the number, shape, and size of cells 480 in each of the three sets of cells are mirror images of one another, and have the same shape and size.

Referring again to FIGS. 3-5, a plurality of axial longitudinal members 450 are formed of a three axial longitudinal member segments, 452, 454, 456, and some of axial longitudinal members 450 are formed of two axial longitudinal member segments. Frame 400 illustrated in FIGS. 6A-6E includes a plurality of axial longitudinal members or axial longitudinal members wherein some of the axial longitudinal members are formed of two axial longitudinal member segments and some of the axial longitudinal members are formed of a single axial longitudinal member segment. Axial longitudinal members 450 can be formed of a single piece of material or be formed of a plurality of pieces of material that have been connected together (e.g., solder connection, weld connection, adhesive connection, mechanical connection, etc.). The axial longitudinal member segments that form each of axial longitudinal members 450 are generally aligned along the longitudinal axis of axial longitudinal member 450. The thickness or cross-sectional area of each of axial longitudinal members 450 along the longitudinal axis of the axial longitudinal member can be constant or vary. The lower axial longitudinal member segments 452 can a greater thickness or cross-sectional area than the upper axial longitudinal member segments 456. The middle axial longitudinal member segments 454 can have a greater thickness or cross-sectional area than upper axial longitudinal member segments 456. The lower axial longitudinal member segments 452 can have generally the same thickness or cross-sectional area as middle axial longitudinal member segments 454. As can be appreciated, lower axial longitudinal member segments 452 can have a different thickness or cross-sectional area as middle axial longitudinal member segments 454. The cross-sectional shape of each the axial longitudinal members 450 along the longitudinal length of axial longitudinal member 450 can be constant or vary. The longitudinal length of the axial longitudinal member segments can be the same or different. The lower axial longitudinal member segments 452 can have a longitudinal length that is less than a longitudinal length of either or both of middle axial longitudinal member segments 454 and upper axial longitudinal member segments 456, and the middle axial longitudinal member segments 454 can have a longitudinal length that is greater than either or both lower axial longitudinal member segments 452 and upper axial longitudinal member segments 456. As illustrated in FIG. 4, lower axial longitudinal member segments 452 has the shortest longitudinal length, and the middle axial longitudinal member segments 454 has the longest longitudinal length.

As illustrated in FIGS. 3 and 4, frame 400 includes a first row 420 of angular articulating members 410, a second row 422 of angular articulating members 410, a third row 424 of angular articulating members 410, and a fourth row 426 of angular articulating members 410. First row 420 of angular articulating members 410 is the bottom row and fourth row 426 of angular articulating members 410 is the top row. The shape, size, and/or configuration of angular articulating members 410 of first row 420 are the same. The shape, size, and/or configuration of angular articulating members 410 on second row 422 are the same. The shape, size, and configuration of angular articulating members 410 of third row 424 are the same. The shape, size, and/or configuration of a plurality of angular articulating members 410 on fourth row 426 are the same and a plurality of angular articulating members 410 on fourth row 436 are different. Referring again to FIG. 4, angular articulating members 410 on fourth row 426, wherein either first end 412 or second end 414 the angular articulating members 410 is connected to frame opening arrangements 460, have a different shape, size, and/or configuration from angular articulating members 410 on fourth row 426 wherein both first end 412 and second end 414 of angular articulating members 410 are connected to axial longitudinal members 450.

Referring again to FIGS. 3-6E, each of the angular articulating members 410 are formed of a centrally located arcuate portion or semi-circular portion 430, and first and second arms 432, 434 that extend from each side of semi-circular portion 430. First arm 432 terminates at first end 412 and second arm 434 terminates at second end 414. Each of first and second arms 432, 434 include one or more undulations 440, 442. As illustrated in FIG. 4, first arm 432 includes first and second undulations 440, 442, wherein the first undulation 440 is located closer to semicircular portion 430 than the second undulation 442. Also, second arm 434 includes first and second undulations 440, 442, wherein first undulation 440 is located closer to semicircular portion 430 than second undulation 442. As such, each angular articulating members 410 includes at least three undulations along a longitudinal length of the angular articulating members 410. As illustrated in FIG. 4, each angular articulating members 410 includes five undulations along the longitudinal length of the angular articulating members 410.

As best illustrated in FIG. 4, each of first and second arms 432, 434 of all of angular articulating members 410 include two undulations; however, the shape and size of the undulations for two or more of the rows of angular articulating members 410 is different; however, this is not required. As also illustrated in FIG. 4, the shape and size of the undulations and the location of the undulations on angular articulating members 410 on each row of angular articulating members 410 are generally the same. As illustrated in FIG. 4, the shape and size of the undulations and the location of the undulations the angular articulating members 410 on first and second rows 420, 422 are the same or very similar (e.g., dimensions are less than 5% different). As also illustrated in FIG. 4, the shape and size of the undulations on angular articulating members 410 on the third row are different from first, second and fourth rows 420, 422, 426. Further, the shape and size of the undulations on angular articulating members 410 on the fourth row are different from first, second and third rows 420, 422, 424. In another non-limiting embodiment, for a plurality of angular articulating members 410, the length, shape and/or size of first and second arms 432, 434 are the same or very similar (e.g., dimensions are less than 5% different). In one non-limiting configuration, angular articulating members 410 that form first row 420 of angular articulating members 410 have first and second arms 432, 434 wherein the length, shape, and size of first and second arms 432, 434 are the same. In another non-limiting configuration, angular articulating members 410 that form second row 422 of angular articulating members 410 have first and second arms 432, 434 wherein the length, shape, and size the first and second arms 432, 434 are the same. In another non-limiting configuration, the angular articulating members 410 that form third row 424 of angular articulating members 410 have first and second arms 432, 434 wherein the length, shape, and size of first and second arms 432, 434 are the same. In another non-limiting configuration, angular articulating members 410 that form fourth row 424 of angular articulating members 410 have first and second arms 432, 434 wherein the length and shape of first and second arms 432, 434 are not all the same. In another non-limiting configuration, angular articulating members 410 for first and second rows 420, 422 have first and second arms 432, 434 wherein the length, shape, and size of first and second arms 432, 434 are 410 of first and second arms 432, 434 are the same or very similar (e.g., dimensions are less than 5% different) for angular articulating members 410 for first and second rows 420, 422. In another non-limiting configuration, angular articulating members 410 on each of first, second, third and fourth rows 420, 422, 424 and 426 a) have the same width, and/or b) the center point of semi-circular portion 430 is located with ±5% (and all values and ranges therebetween) the midpoint between adjacently positioned axial longitudinal members 450.

Referring again to FIGS. 3-6E, the spacing of angular articulating members 410 between adjacently positioned rows 420, 422, 424, 426 of angular articulating members 410 can be the same or different. In one non-limiting embodiment, the spacing of angular articulating members 410 between adjacent positioned rows (e.g., the first and second rows, the second and third rows, the third and fourth rows, etc.) is different. As illustrated in FIG. 4, the spacing between semi-circular portion 430 of first and second rows 420, 422 of angular articulating members 410 is greater than the spacing between semi-circular portion 430 of second and third rows 422, 424 of angular articulating members 410, and the spacing between first ends 412 of first and second rows 420, 422 of angular articulating members 410 is less than the spacing between first ends 412 of second and third rows 422, 424 of angular articulating members 410, and the spacing between second ends 414 of first and second rows 420, 422 of angular articulating members 410 is less than the spacing between second ends 414 of second and third rows 422, 424 of angular articulating members 410. As also illustrated in FIG. 4, semi-circular portion 430 of first and second rows 420, 422 of angular articulating members 410 are oriented toward the top of the frame, and semi-circular portion 430 of third and fourth rows 424, 425 of angular articulating members 410 are oriented toward the bottom of the frame. As such, the semi-circular portion 430 of second and third rows 422, 424 of angular articulating members 410 face one another. As also illustrated in FIG. 4, the spacing between semi-circular portion 430 of third and fourth rows 424, 426 of angular articulating members 410 is greater than the spacing between semi-circular portion 430 of first and second rows 420, 422 of angular articulating members 410, and the spacing between first ends 412 of third and fourth rows 424, 426 of angular articulating members 410 is greater than the spacing between first ends 412 of first and second rows 420, 422 of angular articulating members 410, and the spacing between second ends 414 of third and fourth rows 424, 426 of angular articulating members 410 is greater than the spacing between second ends 414 of first and second 420, 422 of angular articulating members 410. As also illustrated in FIG. 4, the spacing between semi-circular portion 430 of third and fourth rows 424, 426 of angular articulating members 410 is greater than the spacing between semi-circular portion 430 of second and third rows 422, 424 of angular articulating members 410, and the spacing between first ends 412 of third and fourth rows 424, 426 of angular articulating members 410 is less than the spacing between first ends 412 of second and third rows 422, 424 of angular articulating members 410, and the spacing between second ends 414 of third and fourth rows 424, 426 of angular articulating members 410 is less than the spacing between second ends 414 of second and third rows 422, 424 of angular articulating members 410.

As illustrated in FIGS. 6A-6E, the spacing of the angular articulating members in the adjacently positioned rows can be different.

Referring now to FIGS. 3-6E, frame opening arrangements 460 are located between third and fourth rows 424, 426 of angular articulating members 410. As can be appreciated, one or more frame opening arrangements 460 can be located on other regions of frame 400. Frame opening arrangements 460 can optionally be used as securing locations for one of more leaflet structures 200; however, it can be appreciated that one or more of frame opening arrangements 460 can optionally be used as securing locations for other structures (e.g., leaflet, inner skirt, outer skirt, etc.), and/or be used as an indicator of the orientation and/or location of frame 400 in a body passageway or heart valve. Alternatively, an orientation structure 490 can be included in the frame 400. As illustrated in FIGS. 3-6E, each of frame opening arrangements 460 includes first and second frame opening struts 470, 472 that form a lower frame opening 462 and an optional an upper frame opening 464, 466 therebetween. The size and shape of lower frame opening 462 and optional an upper frame opening 464, 466 are non-limiting. As illustrated in FIGS. 3 and 4, lower frame opening 462 has a generally rectangular shape and extends only partially along the longitudinal length of frame opening arrangement 460. As can be appreciated, lower frame opening 462 can have other shapes and sizes. In one non-limiting configuration, each of frame opening arrangements 460 includes a lower frame opening 462 and lower frame openings 462 all have the same or very similar (e.g., dimensions are less than 5% different) shape and size. In one non-limiting embodiment, one or both of first and second frame opening struts 470, 472 a) has a longitudinal axis that is parallel to the longitudinal axis of axial longitudinal member 450 to which the bottom of frame opening arrangements 460, and/or b) has a longitudinal axis that is offset from the longitudinal axis of axial longitudinal member 450 to which the bottom of frame opening arrangements 460. As illustrated in FIGS. 3 and 4, both of first and second frame opening struts 470, 472 a) has a longitudinal axis that is parallel to the longitudinal axis of axial longitudinal member 450 to which the bottom of frame opening arrangements 460, and b) has a longitudinal axis that is offset from the longitudinal axis of axial longitudinal member 450 to which the bottom of frame opening arrangements 460 is connected thereto. The longitudinal length of one or both of first and second frame opening struts 470, 472 can be the same or less than the longitudinal length of length for an axial longitudinal member segment that is located adjacent to first and second frame opening struts 470, 472. As illustrated in FIG. 4, the longitudinal length of first and second frame opening struts 470, 472 is about the same as the longitudinal length of length of axial longitudinal member segment 456.

As illustrated in FIG. 4, the end of first or second arms 432, 434 of angular articulating members 410 of fourth row 426 that is connected to frame opening arrangements 460 can optionally be configured to angle downwardly, and the other end of first or second arms 432, 434 of angular articulating members 410 that is connected to an axial longitudinal member segment is configured to angle upwardly. As illustrated in FIG. 4, the ends of first and second arms 432, 434 of angular articulating members 410 of first, second and third rows 440, 422 and 424 that is connected to an axial longitudinal member segment are both angled in the same direction. As illustrated in FIG. 4, the angle β of angular articulating members 410 relative to axial longitudinal members 450 when the frame is in the expanded orientation is generally 25-60° (and all values and ranges therebetween). A similar arrangement regarding the connection of the angular articulating members to the axial longitudinal member or frame opening arrangements is illustrated in FIGS. 6A-6E.

Referring now to FIGS. 3 and 4, frame opening arrangements 460 can optionally include one or more optional upper frame openings 464, 466. One or more optional upper frame openings 464, 466 are generally positioned above lower frame opening 462. Generally, one or more optional upper frame openings 464, 466 have a cross-sectional area or size that is less than lower frame opening 462; however, this is not required. As illustrated in FIGS. 3 and 4, the shape of two or more of optional upper frame openings 464, 466 are different. The different shapes of one or more optional upper frame openings 464, 466 can be used as a marker to facilitate in the proper positioning of frame 400 and prosthetic heart valve 100 in the heart. In one specific non-limiting configuration, each of one more optional upper frame openings 464, 466 has a different shape. As illustrated in FIG. 3, two of frame opening arrangements 460 include two different shaped upper frame openings 464, 466 and other frame opening arrangements 460 is absent an upper frame opening. As illustrated in FIG. 6, frame 400 is absent upper frame openings.

The top portion of each of frame opening arrangements 460 can optionally include a top marker 468. The shape and size of top marker 468 (when used) is non-limiting. As illustrated in FIGS. 3 and 4 and 6 the shape and size of markers 468 are the same or very similar (e.g., dimensions are less than 5% different). Top markers 468 can be used as a marker to facilitate in the proper positioning of frame 400 and prosthetic heart valve 100 in the heart. The one or more top markers 468 (when used) can also or alternatively be used to enable one or more components of prosthetic heart valve 100 (e.g., leaflet, inner skirt, outer skirt, etc.) to be connected to frame 400. The top markers 468 can be formed of the same or different material from other portions of frame 400.

Non-limiting dimensions of a frame 400 that is formed of the metal alloy in accordance with the present disclosure and which can be expanded to 26 mm can include a) axial longitudinal members 450 having a length of 18-28 mm (and all values and ranges therebetween), b) a length of frame 400 in a flat state that is generally 70-95 mm (and all values and ranges therebetween), c) axial longitudinal members 450 having a width that generally ranges between 0.2-0.7 mm (and all values and ranges therebetween), d) axial longitudinal members 450 having a depth that is generally ranges between 0.2-0.7 mm (and all values and ranges therebetween), c) angular articulating members 410 having a width that generally ranges between 0.2-0.7 mm (and all values and ranges therebetween), f) angular articulating members 410 having a depth that generally ranges between 0.2-0.7 mm (and all values and ranges therebetween), g) a spacing of adjacently positioned axial longitudinal members 450 that is generally 6-12 mm (and all values and ranges therebetween), h) the number of cells 480 in each of the sets of cells can be 2-20 (and all values and ranges therebetween). The width and/or depth of the lower axial longitudinal members can optionally be greater than the one or more of the upper axial longitudinal members. Likewise, the width and/or depth of the angular articulating members can optionally be greater than the one or more of the upper angular articulating members.

FIGS. 3 and 4 illustrate frame 400 in an expanded position and FIG. 5 illustrates frame 400 in the unexpanded or crimped position.

The frame 400 is partially or fully formed of a refractory metal alloy or a metal alloy that includes at least 15 awt. % rhenium.

Frame 110 of prosthetic heart valve 100, when formed of a refractory metal alloy or a metal alloy that includes at least 15 awt. % rhenium, can be crimped to have a crimped outer diameter that is a) at least 5% and up to a 33% smaller (e.g., 5-33% smaller and all value and ranges therebetween) than a crimped outer diameter of a frame of the same size, configuration, and shape that is formed of Co—Cr alloy; b) at least 5% and up to a 40% smaller (e.g., 5-40% smaller and all value and ranges therebetween) than a crimped outer diameter of a frame of the same size, configuration, and shape that is formed of Nitinol, and/or c) at least 5% and up to a 40% smaller (e.g., 5-40% smaller and all value and ranges therebetween) than a crimped outer diameter of a frame of the same size, configuration, and shape that is formed of TiAlV alloys.

A frame 400 for a prosthetic heart device (e.g., TAVR, etc.) that is formed of a refractory metal alloy or a metal alloy that includes at least 15 awt. % rhenium has one or more improved properties or advantages as compared to frames for prosthetic heart valves that are formed of Co—Cr alloy, TiAlV alloy, or NiTi alloy, namely 1) the outer diameter (OD) of the crimped prosthetic valve having a frame formed of a refractory metal alloy or a metal alloy that includes at least 15 awt. % rhenium is smaller than the OD crimped diameter of the crimped prosthetic valve having the same frame dimensions but formed of Co—Cr alloy, TiAlV alloy, or NiTi alloy, 2) the strut joint width on the frame (e.g., the location that the end of an angular articulating member and/or axial longitudinal member is connected to another portion of the frame) that is formed a refractory metal alloy or a metal alloy that includes at least 15 awt. % rhenium can be less than the strut joint width on the frame formed of Co—Cr alloy, TiAlV alloy, or NiTi alloy while still forming a frame that is as strong as a frame formed by Co—Cr alloy, TiAlV alloy, or NiTi alloy, 3) the width of the angular articulating member and/or axial longitudinal member on the frame that is formed a refractory metal alloy or a metal alloy that includes at least 15 awt. % rhenium can be less than the angular articulating member and/or axial longitudinal member on the frame formed of Co—Cr alloy, TiAlV alloy, or NiTi alloy while still forming a frame that is as strong as a frame formed by Co—Cr alloy, TiAlV alloy, or NiTi alloy, 4) the amount of recoil of a frame that is formed of a refractory metal alloy or a metal alloy that includes at least 15 awt. % rhenium after the frame has been crimped or after the frame has been expanded is less than the amount of recoil of a frame having the same frame dimensions but formed of Co—Cr alloy, TiAlV alloy, or NiTi alloy, and/or 5) the amount of longitudinal foreshortening of a frame that is formed of a refractory metal alloy or a metal alloy that includes at least 15 awt. % rhenium after the frame has been expanded is less than the amount of longitudinal foreshortening of a frame having the same frame dimensions but formed of Co—Cr alloy, TiAlV alloy, or NiTi alloy.

The configuration of the frame as illustrated in FIGS. 3-6E results in little or no longitudinal foreshortening of a frame when the frame is expanded from a crimped state. Generally, the amount of longitudinal foreshortening of a frame from a crimped state to an expanded state is 0-20% (and all values and ranges therebetween), typically 0-15%, more typically 0-10%, and still more typically 0-5%. The orientation and configuration of the axial longitudinal member segments (e.g., 452, 454, 456) facilitates in the reduction of longitudinal foreshortening of a frame when the frame is expanded from a crimped state. Likewise, the orientation and configuration of the axial longitudinal member segments (e.g., 452, 454, 456) facilitates in the reduction of longitudinal foreshortening of a frame when the frame is crimped. A reduced amount of longitudinal foreshortening facilitates in ensuring the prosthetic heart implant when the frame is expanded from the crimped state maintains its proper position in the treatment area. Frames of prosthetic heart implant that foreshorten result in a reduction in longitudinal length when the frame is expanded. Such reduction in longitudinal length during expansion of the frame can result in the mislocation of the expanded prosthetic heart implant in a treatment area, which mislocation can result in a) improper operation of the implanted prosthetic heart implant, b) damage to the implanted prosthetic heart implant, c) potential damage to the tissue about the implanted prosthetic heart implant, d) reduced life of the prosthetic heart implant, and/or c) causing plaque and/or calcium deposits to form about the prosthetic heart implant.

The strength of the refractory metal alloy or a metal alloy that includes at least 15 awt. % rhenium used to partially or fully form frame 400 can optionally be greater than a cobalt-chromium alloy, nickel-titanium alloy, or a TiAlV alloy, thus the width of the angular articulating member and/or axial longitudinal member and/or strut joints of frame 400 can be made smaller than frames formed of cobalt-chromium alloy, nickel-titanium alloy, or a TiAlV alloy, thereby enabling the frame to be made smaller without sacrificing the strength of the frame.

As illustrated in the Table 1 illustrated in FIG. 7, the Yield Strength and Young's Modulus (or Modulus of Elasticity) of a MoRe alloy (e.g., 45-55 wt. % Re & 45-55 wt. % Mo) is compared to two CoCr alloys (e.g., MP35N and L605) and a stainless-steel alloy (316L). As indicated in Table 1, the Yield Strength of the MoRe alloy is at least 2 times the Yield Strength of CoCr alloys such as MP35N and L605 and a stainless-steel alloy such as 316L. Also, the Young's Modulus of the MoRe alloy is at least 1.5 times the Young's Modulus of CoCr alloys such as MP35N and L605 and a stainless-steel alloy such as 316L. In one non-limiting embodiment, the metal alloy that is used to form 75%-100% (and all values and ranges therebetween) of the frame has a Yield Strength that is at least 1.1 times (e.g., 1.1-4 times and all values and ranges therebetween) of CoCr alloys, MP35N alloys, L605 alloys, SS alloys, stainless steel 316L alloy. In another non-limiting embodiment, the metal alloy (e.g., refractory metal alloy, refractory metal alloy that includes at least 25 wt. % rhenium, metal alloy that includes at least 15 awt. % rhenium) that is used to form 75%-100% (and all values and ranges therebetween) of the frame has a Young's Modulus that is at least 1.1 times (e.g., 1.1-2.5 times and all values and ranges therebetween) of CoCr alloys, MP35N alloys, L605 alloys, SS alloys, stainless steel 316L alloy.

Figure 8:
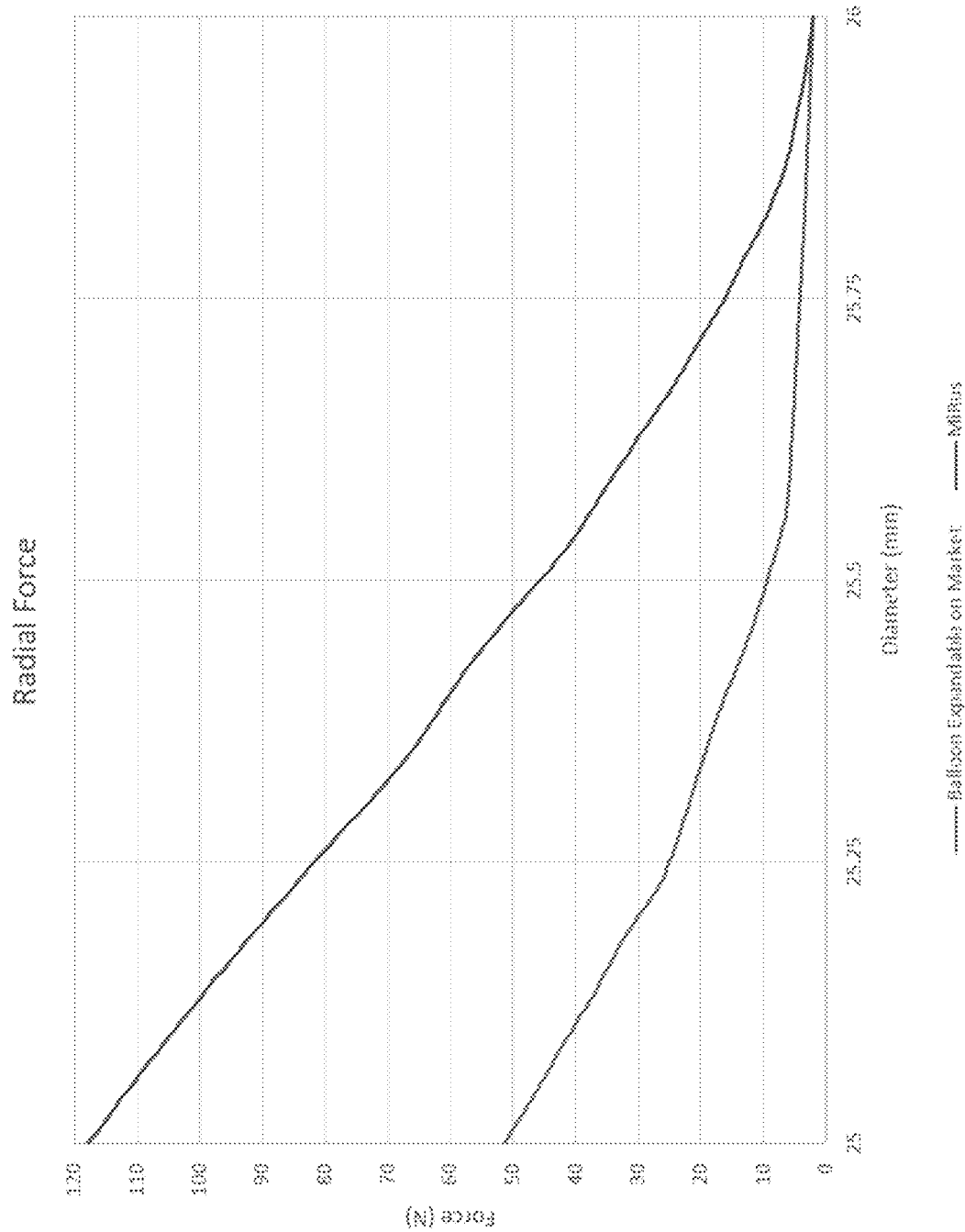
FIG. 8 is a graph that compares the radial strength of frame form of a MoRe alloy to a frame formed of CoCr alloy.

Referring now to FIG. 8, a graph provides a comparison of the radial force of two frames for a prosthetic heart valve that have the same size and configuration and wherein on of the frames is a MiRus™ frame that is formed of a MoRe alloy (e.g., 45-55 wt. % Re & 45-55 wt. % Mo) and the other frame is formed of a MP35N alloy. As illustrate din FIG. 8, for frames that are expanded up to 25.75 mm in diameter, the frame formed of a MoRe alloy has a larger radial strength that a frame formed of MP35N alloy. As such, the angular articulating member and/or axial longitudinal member of the frame that is formed of MoRe alloy can be made thinner than a frame formed of MP35N alloy and still have the same or greater radial strength as a frame formed of MP35N alloy. Also, the greater radial force provided by the metal alloy allows for a larger open cell size in the frame as compared to prior art frames and smaller crimped profiles as compared to prior art frames.

The amount of recoil of a material used in the frame formed of a refractory metal alloy or a metal alloy that includes at least 15 awt. % rhenium when the frame is plastically deformed (e.g., crimped, expanded from the crimped state, etc.) can be less than the amount of recoil of a same sized and configured frame formed of cobalt-chromium alloy, nickel-titanium alloy, or a TiAlV alloy. The amount of recoil of a refractory metal alloy or a metal alloy that includes at least 15 awt. % rhenium when the frame is crimped or when the frame is expanded from a crimped stated is generally no more than 8% (e.g., 0-8% and all values and ranges therebetween), typically no more than 5%, more typically no more than 3%, still more typically no more than 2%, and even more typically less than 2%. Due to the low amount of recoil, the frame only needs to be subjected to a single crimping cycle to obtain the smallest crimping outer diameter of the crimped frame. Frames formed of metal alloys having a larger recoil typically need to be subjected to multiple crimping processes to obtain the designed side of the crimped frame.

Figure 9:
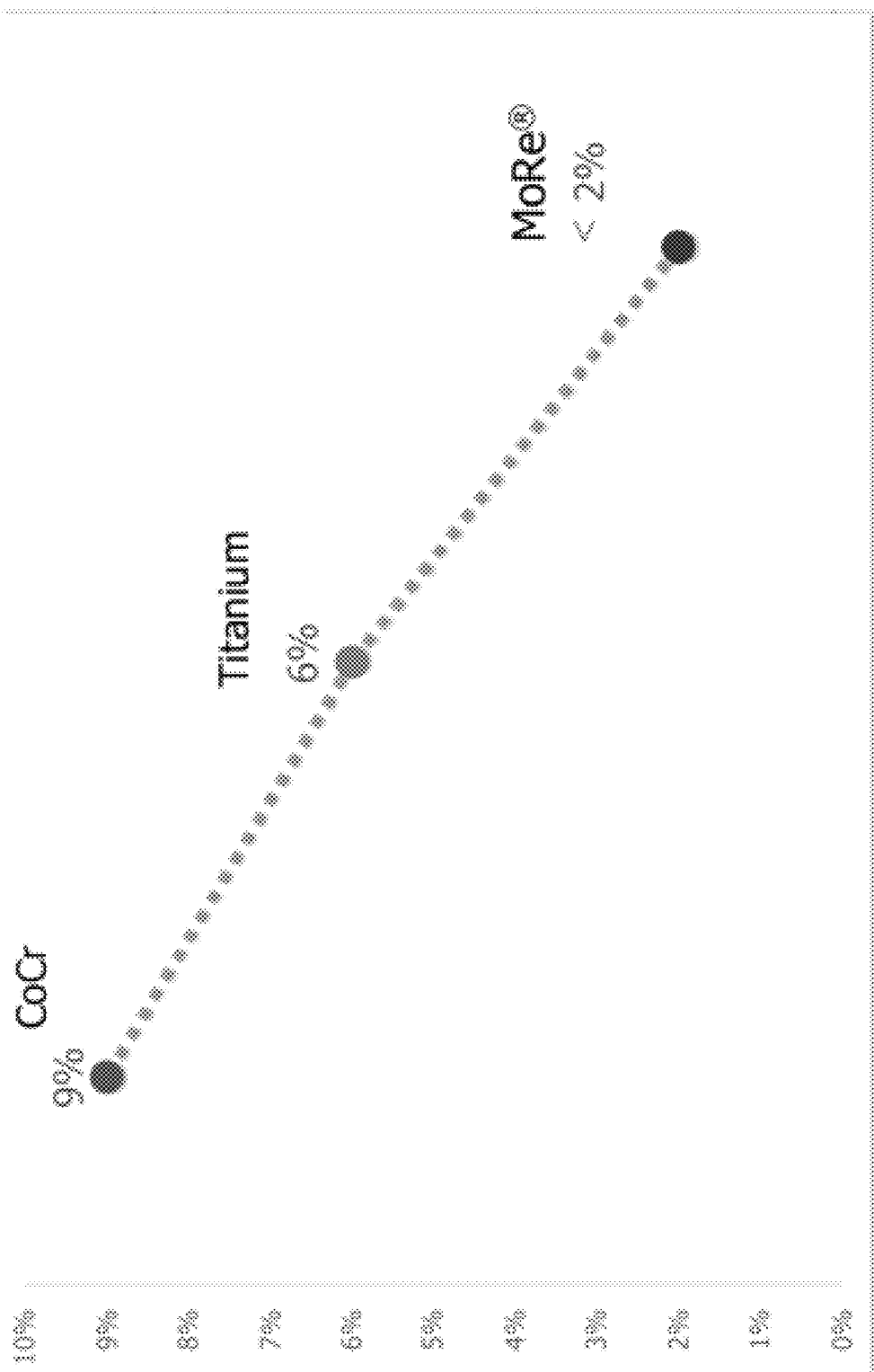
FIG. 9 is a graph that illustrates the amount of recoil of several different metal alloys.

As illustrated in FIG. 9, the crimping of a frame that is formed of a) Co—Cr alloy (e.g., 35Co-35Ni-20Cr-10Mo) will recoil by 9% or more (e.g., 9-15% and all values and ranges therebetween) after the radial crimping forces are removed from the frame, or b) titanium alloy (e.g., e.g., Ti-6Al-4V) will recoil by 6% or more (e.g., 6-10% and all values and ranges therebetween) after the radial crimping forces are removed from the frame. FIG. 9 illustrates that a frame form of MoRe alloy (e.g., 45-55 wt. % Re & 45-55 wt. % Mo) will recoil less than 2% (e.g. 0.1-1.99% and all values and ranges therebetween) after being crimped or expanded. As such, when the frame is formed of a metal alloy that has reduced recoil, the need to subject the frame to multiple crimping cycles or procedures can eliminated, thereby a) reducing the incidence of damage to the frame, b) reducing the incidence of damage the leaflets of the prosthetic heart valve, c) reducing the incidence of damage the inner and/or outer skirt on the prosthetic heart valve, and/or d) reducing the incidence of damage to other components of the prosthetic heart valve (e.g., damage to balloon on the catheter, damage to one or more components on the catheter, etc.). The reduction in recoil after the expansion of the frame formed of a refractory metal alloy or a metal alloy that includes at least 15 awt. % rhenium results in the frame better conforming to the size of the orifice in the heart. As such, the increased EOA (effective orifice area) results in a reduction of perivalvular leak (i.e., a leak caused by a space between the patient's natural heart tissue and the valve replacement). The larger recoil of the frame formed of Co—Cr alloy or Ti alloy results in reduced EOA and increase amount of perivalvular leak about the prosthetic heart valve.

Figure 10:
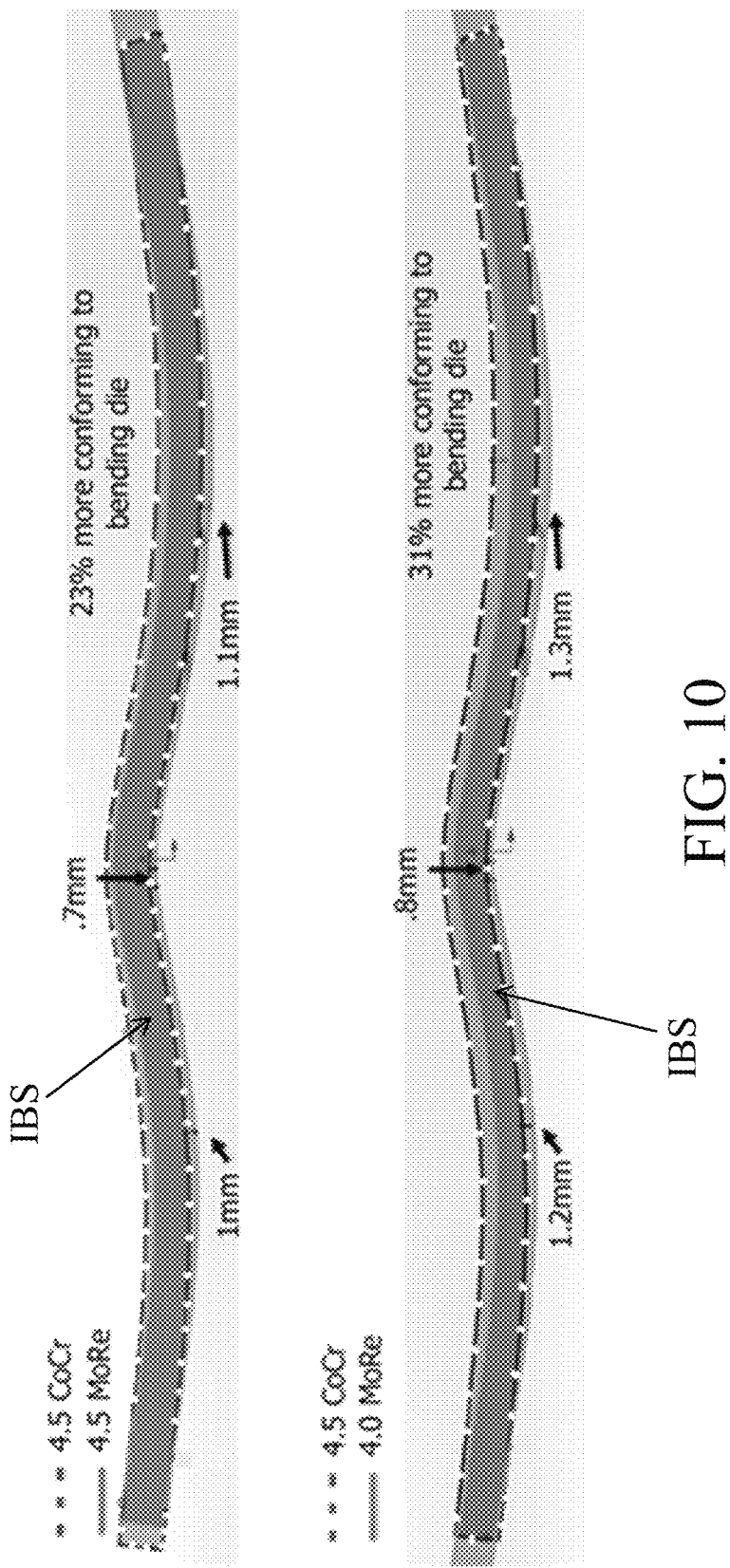
FIG. 10 is an illustration that compares the conformability of a metal strip or wire formed of refractory metal to the shape of a die surface as compared to the conformity of a metal strip or wire of CoCr alloy on the same die surface.

FIG. 10 illustrates two different wires formed of CoCr and a refractory metal such as MoRe to illustrate the conformability to bending of the two types of wires. When the frame of the prosthetic heart implant is expanded, the angular articulating member and/or axial longitudinal member of the frame plastically deform (e.g., generally deform outwardly) due to the expansion of the inflatable balloon or from some other expansion device. Generally, the treatment location where the prosthetic heart implant is expanded is not perfectly cylindrical nor has a perfectly shaped circular cross-sectional shape. Generally, the treatment area is damaged and/or includes plaque, calcium deposits, and/or other materials (e.g., prior implanted medical devices, etc.) that cause the shape of the treatment area to be non-cylindrical-shaped or have a non-circular cross-sectional shape. As such, frames of prosthetic heart implants that can better conform to the irregular shapes in a treatment location result in a prosthetic heart implant that better fits the treatment area and can result in a reduction of perivalvular leak or other types of leakage about the outer perimeter of the expanded prosthetic heart implant. FIG. 10 illustrates that when same sized and configured angular articulating members and/or axial longitudinal members of the frame that are formed of MoRe or Co—Cr alloy are subjected to the same bending force, the MoRe angular articulating member and/or axial longitudinal member better conforms to the ideal bending shape IBS than the Co—Cr alloy angular articulating member and/or axial longitudinal member. The two bending tests illustrate that the angular articulating member and/or axial longitudinal member formed of refractory metal alloy such a MoRe had 23% and 31% better conformity to the ideal bending shape than the angular articulating member and/or axial longitudinal member formed of CoCr. The ability to conform to a specific shape is largely dependent upon the recoil of the alloy used to form the angular articulating member and/or axial longitudinal member. It has been found that angular articulating members and/or axial longitudinal members formed of a refractory metal alloy or a metal alloy that includes at least 15 awt. % rhenium can have about 15-45%

(and all values and ranges therebetween) better conformity to bending to an idea bending shape formed by a die than the same sized angular articulating members and/or axial longitudinal members formed of Co—Cr alloy, TiAlV alloy, or Ni—Ti alloy. Such improved shape conformity results in improved conformity of an expanded prosthetic heart valve frame to a treatment area shape as illustrated in FIGS. 11A and 11B.

FIG. 11A illustrates the conformability of an expanded frame 500 formed of Co—Cr alloy in an irregularly shaped annulus 400 of a heart wherein the treatment area includes calcium deposits CD and leakage regions PVL about the outer perimeter of the expanded frame. The expanded frame forms an EOA of about 585 mm². Due to the inability of the CoCr alloy to readily conform to irregular shapes in the annulus, an open area of about 46 mm² is located about the outer perimeter of the expanded frame to allow for PVL about the expanded TAV. FIG. 11B illustrates the conformability of an expanded frame 600 formed of a refractory metal alloy such as MoRe in an irregularly shaped annulus 400 of a heart. The expanded frame forms an EOA of about 679 mm² due to the improved ability of the refractory metal alloy to conform to irregular shapes in the annulus. As such, only an area of about 14 mm² is located about the outer perimeter of the expanded frame. The expanded frame formed of refractory metal alloy is illustrated as being more than 30% (e.g., 30-40% and all values and ranges therebetween) more conformable to irregularly shaped annulus 400 of a heart as compared to the same shaped and sized frame Co—Cr alloy. In general, expandable frames formed of a refractory metal alloy or a metal alloy that includes at least 15 awt. % rhenium are about 10-50% (and all values and ranges therebetween) more conformable to irregularly shaped body passageways as compared to a same sized and configured frame formed of Co—Cr alloy, TiAlV alloy, or Ni—Ti alloy.

Figures 12A, 12B, 12C:
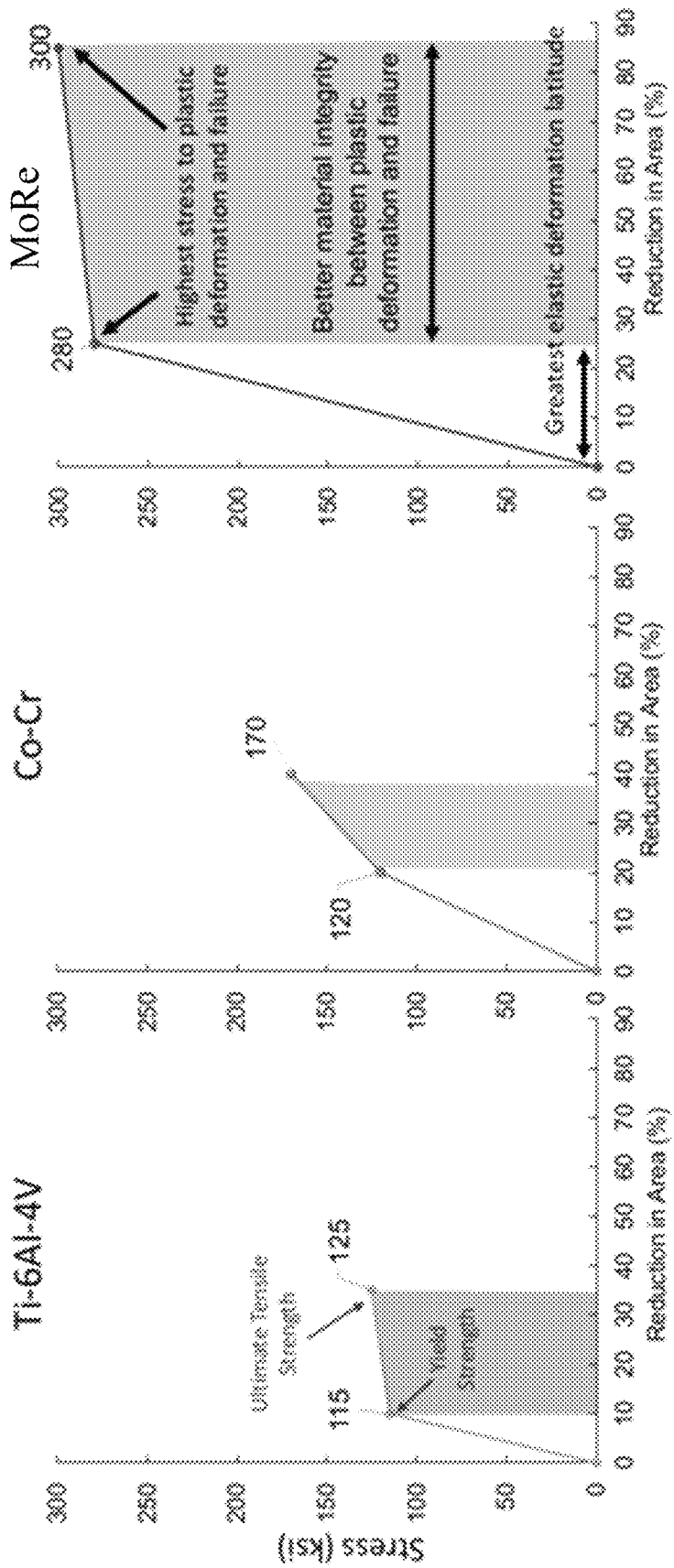
FIGS. 12A-12C illustrate stress vs. reduction in percent area graphs of TiAlV alloy, CoCr alloy, and MoRe alloy.

FIGS. 12A-12C illustrate stress vs. reduction in percent area graphs of angular articulating members and/or axial longitudinal members formed of TiAlV alloy, CoCr alloy, and MoRe alloy. These graphs illustrate that angular articulating members and/or axial longitudinal members in the frame formed of a refractory metal alloy such as MoRe have improved properties such as strength, yield strength, ultimate tensile strength, fatigue ductility, greater deformation latitude, material integrity between plastic deformation and failure, and durability as compared to same sized and configured angular articulating members and/or axial longitudinal members formed of CoCr alloy or TiAlV alloy. A refractory metal alloy or a metal alloy that includes at least 15 awt. % rhenium can have a strength of 1.5-5 times (and all values and ranges therebetween) greater than that of Co—Cr alloy, TiAlV alloy, or Ni—Ti alloy.

Figure 13:
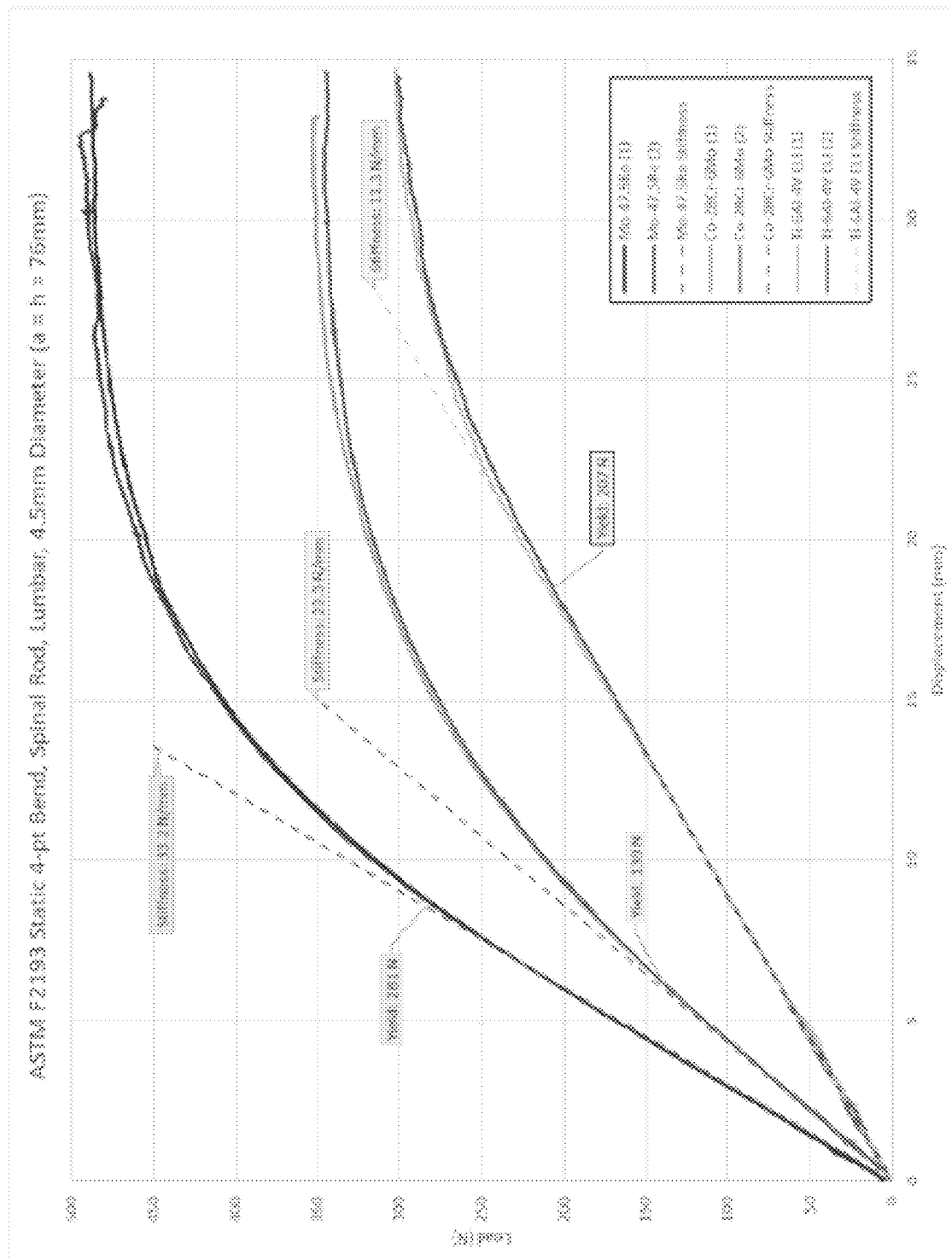
FIG. 13 is a graph that illustrates the differences of stiffness and yield strength of a MoRe alloy, CoCr alloy, and TiAlV alloy.

As illustrated in FIG. 13, an angular articulating member and/or axial longitudinal member formed of refractory metal alloys such as MoRe alloy has a greater stiffness and yield strength as compared to the same sized and configured angular articulating member and/or axial longitudinal member formed of Co—Cr alloy, TiAlV alloy, or Ni—Ti alloy.

Figure 14B:
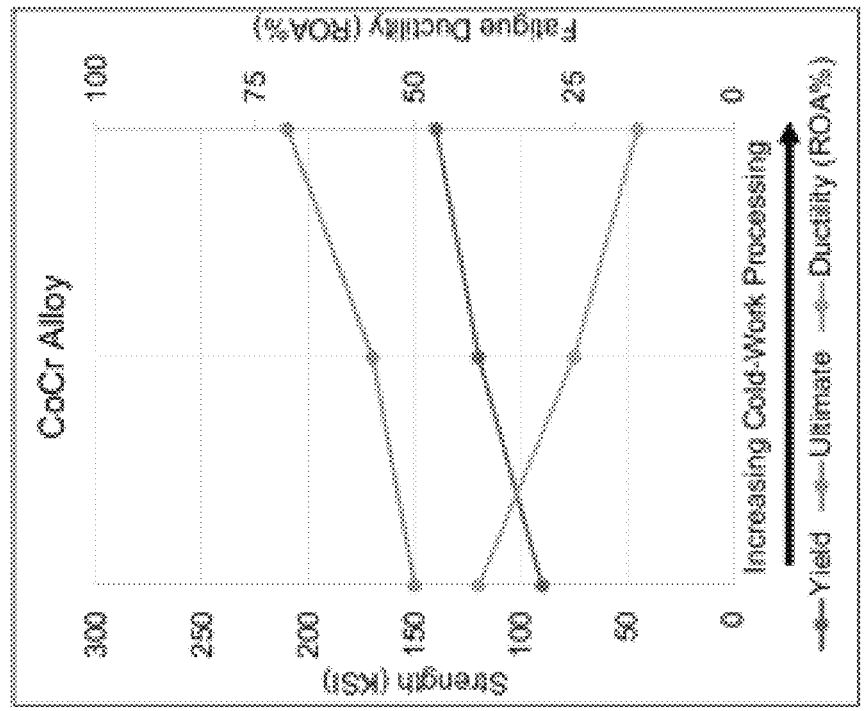
FIGS. 14A-14C are graphs that illustrate the strength and fatigue ductility of a TiAlV alloy, CoCr alloy, and MoRe alloy.
Figure 14A:
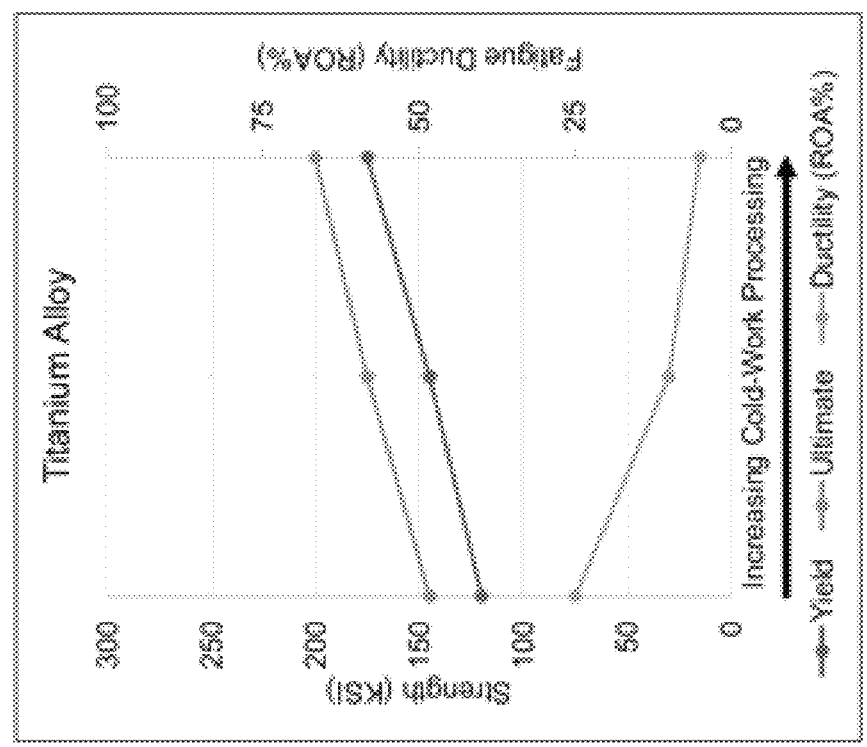
Figure 14C:
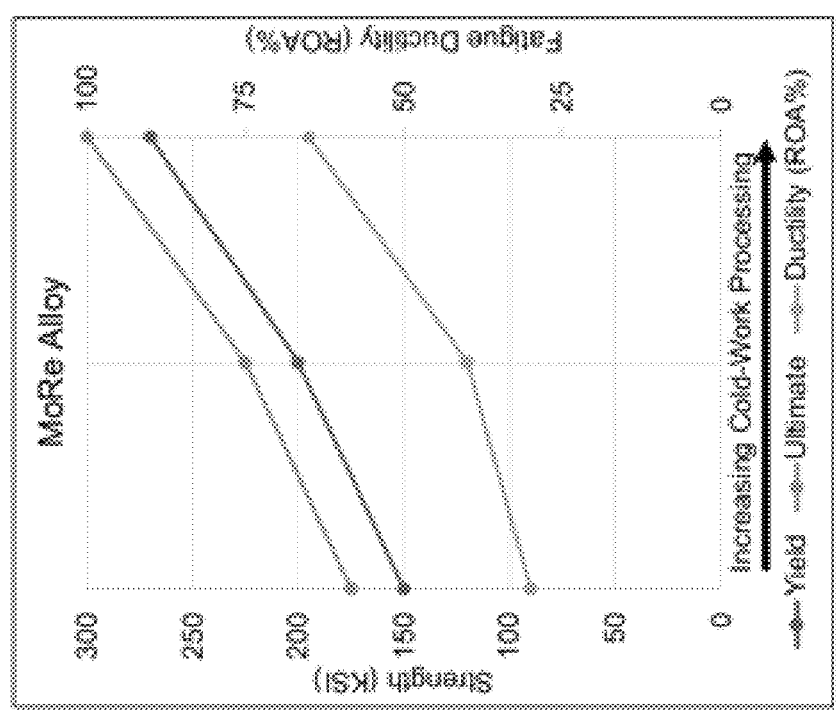

FIGS. 14A-14C are graphs that illustrate the yield strength, ultimate strength, and fatigue ductility of angular articulating members and/or axial longitudinal members formed of TiAlV alloy, CoCr alloy, and MoRe alloy after such alloys are cold worked to reduce the cross-sectional area of the alloy. After being cold worked, a refractory metal alloy such as MoRe alloy has greater fatigue ductility, yield strength, and ultimate strength than Co—Cr alloys and TiAlV alloys. Also, the cold working of the MoRe alloy results in the increased ductility of the alloy, wherein CoCr alloys and TiAlV alloys have a reduction in ductility as additional cold working is applied to the alloy.

Figure 15:
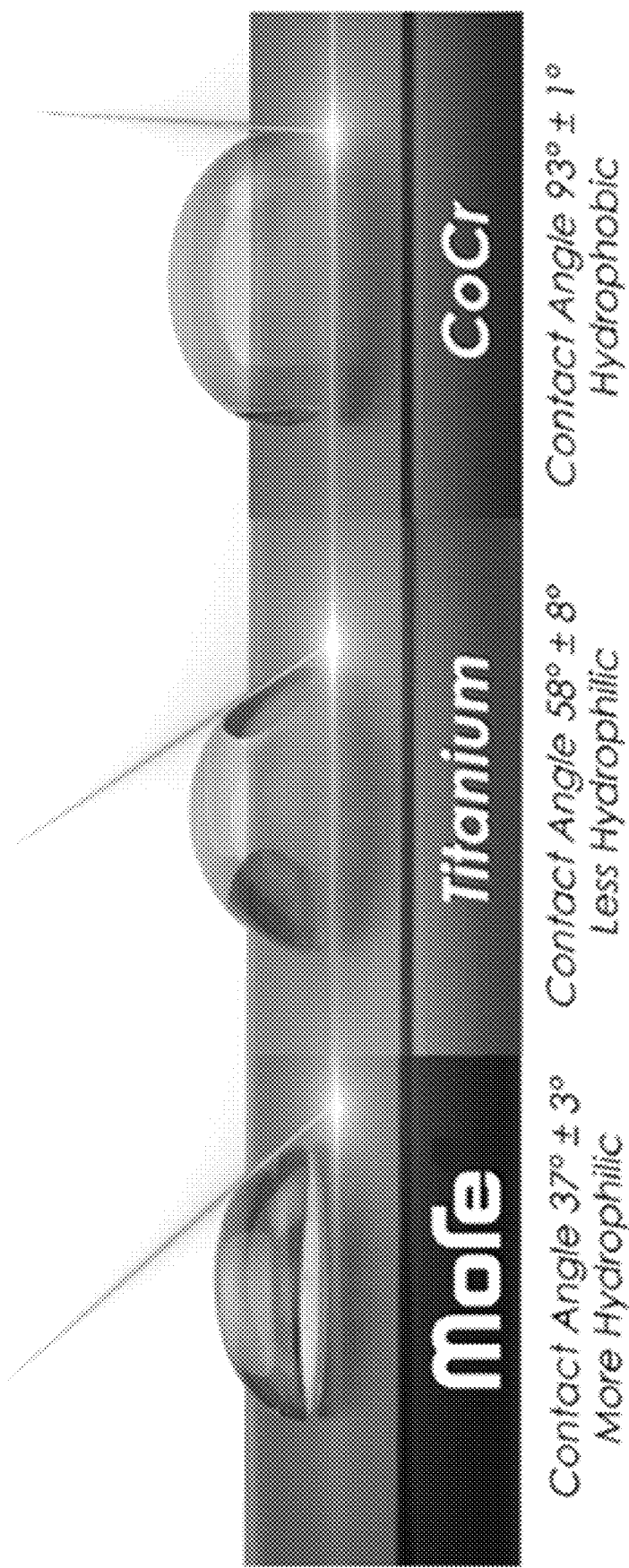
FIG. 15 illustrates the hydrophilicity of a MoRe alloy, a CoCr alloy, and a TiAlV alloy.

FIG. 15 illustrates the hydrophilicity of a refractory metal alloy such as a MoRe alloy compared to a Co—Cr alloy or TiAlV alloy. Hydrophilicity of a material implanted in a patient is an important property of the material with regard to the cell adhesion, cell migration, and cell multiplication of tissue on the material. As illustrated in FIG. 15, Co—Cr alloys are hydrophobic materials resulting in a large contact angle (93°±1°) of a water droplet (e.g., distilled water) positioned on the surface of the Co—Cr alloy. TiAlV alloys are a little more hydrophilic than Co—Cr alloys and exhibit a contact angle of 58°±8° when a water droplet is positioned on the surface of the Ti alloy. Refractory metal alloys such as a MoRe alloy have a much greater hydrophilicity than Co—Cr alloys and TiAlV alloys. The MoRe alloy has a contact angle of 37°±3° when a water droplet is positioned on the surface of the MoRe alloy. Aa refractory metal alloy or a metal alloy that includes at least 15 awt. % rhenium generally have a hydrophilicity wherein the contact angle of a water droplet on the surface of the refractory metal alloy is 25°-45° (and all values and ranges therebetween), and typically 30-42°.

The reduced amount of recoil, improved bending conformity, and greater radial strength of expanded frames of prosthetic heart valves that are at least partially formed of a refractory metal alloy or a metal alloy that includes at least 15 awt. % rhenium as compared to same sized and configured expanded frames of prosthetic heart valves formed of Co—Cr alloy, TiAlV alloy, or Ni—Ti alloy results in the following non-limiting advantages: 1) formation of a frame for a prosthetic heart valve having thinner angular articulating members, axial longitudinal members, and/or strut joints which results in i) safer vascular access when inserting the prosthetic heart valve through a body passageway and to the treatment area, and/or ii) decreased the risk of bleeding and/or damage to the body passageway and/or the treatment area when the prosthetic heart valve is delivered to the treatment area and/or expanded at the treatment area; 2) easier deliverability of the prosthetic heart valve to the treatment area which can result in i) decreased trauma to the body passageway (e.g., blood vessel, aortic arch trauma, etc.) during the insertion and/or expansion of the prosthetic heart valve at the treatment area, and/or ii) decreased risk of neuro complications-stroke; 3) less recoil which results in i) reduced crimping profile size, ii) increased conformability of the expanded prosthetic heart valve at the treatment area after expansion in the treatment area, iii) increased radial strength of the frame of the prosthetic heart valve after expansion at the treatment area, iv) only require a single crimping cycle to crimp the prosthetic heart valve on a balloon catheter or other type of delivery device, v) reduced incidence of damage to components of the prosthetic heart valve (e.g., angular articulating members, axial longitudinal members, strut joints, and/or other components of the expandable frame, leaflets, skirts, coatings, etc.) during the crimping, expansion, and operation of the medical device, vi) greater effective orifice area (EOA) of the prosthetic heart valve after expansion of the medical device, vi) decreased pulmonary valve regurgitation (PVR) after expansion of the prosthetic heart valve in the treatment area, and/or vii) require only a single expansion cycle of the balloon on the balloon catheter or other expansion mechanism to fully expand the prosthetic heart valve; and/or 4) creating a prosthetic heart valve having superior material biologic properties to I) improve tissue adhesion and/or growth on or about prosthetic heart valve, II) reduce adverse tissue reactions with the prosthetic heart valve, III) reduced toxicity of prosthetic heart valve, IV) potentially decrease in-valve thrombosis during the life of the prosthetic heart valve, and/or V) reduce incidence of infection during the life of the prosthetic heart valve.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall therebetween.

To aid the Patent Office and any readers of this application and any resulting patent in interpreting the claims appended hereto, applicants do not intend any of the appended claims or claim elements to invoke 35 U.S.C. 112(f) unless the words "means for" or "step for" are explicitly used in the particular claim.

What is claimed:

1. An expandable prosthetic heart valve comprising an expandable metal frame and at least one leaflet that is connected to said expandable metal frame; said expandable metal frame is configured to be expanded from a crimped orientation to an expanded orientation in a body passageway; said expandable metal frame has distal and proximal ends; said expandable metal frame includes an open cell configuration that includes a plurality of stacked cell rows that are stacked along the longitudinal length of said expandable metal frame; each of said cell rows includes a plurality of frame cells; each of said cell rows has a same number of said frame cells; each of said cell rows includes first and second frame cells; each of said first and second frame cells in each of said cell rows includes a first axial longitudinal member and a second axial longitudinal member; each of said first and second longitudinal axial members extends along a longitudinal length of said expandable metal frame and first and second articulating members that are connected to said first and second axial longitudinal members; at least 80% of a longitudinal length of each said first and second axial longitudinal members in said first and second frame cells is oriented parallel to a central axis of said expandable metal frame when said expandable metal frame is in said crimped and expanded orientations; each of said first axial longitudinal members in said first frame cell in each of said cell rows includes one end that is connected to an end of another of said first axial longitudinal members of at least one of said first frame cells in a different cell row; each of said first axial longitudinal members in said second frame cell in each of said cell rows includes one end that is connected to an end of another of said first axial longitudinal members of at least one of said second frame cells in a different cell row; each of said first axial longitudinal members in said first and second frame cells has a continuous linear shape along at least 80% of said longitudinal length of said first axial longitudinal member; each of said second axial longitudinal members in said first frame cell in each of said cell rows includes one end that is connected to an end of another of said second axial longitudinal members of at least one of said first frame cells in a different cell row; each of said second axial longitudinal members in said second frame cell in each of said cell rows includes one end that is connected to an end of another of said second axial longitudinal members of at least one of said second frame cells in a different cell row; at least one of said second axial longitudinal members in said first and second frame cells has a continuous linear shape along at least 80% of said longitudinal length of said second axial longitudinal member; a top end of each set of connected together first axial longitudinal members defines a portion of said proximal end of said expandable metal frame; a bottom end set of each connected together first axial longitudinal members defines a portion of said proximal end of said expandable metal frame; a top end of a plurality of sets of connected together first axial longitudinal members defines a portion of said proximal end of said expandable metal frame; a bottom end of a plurality of sets of connected together first axial longitudinal members defines a portion of said proximal end of said expandable metal frame; a middle region of each of said first and second articulating members in each frame cell in said cell row that is located closest to said proximal end of said expandable metal frame is positioned below an upper end of said first and second axial longitudinal members when said expandable metal frame is in said crimped orientation; a middle region of each of said first and second articulating members in each frame cell in said cell row that is located closest to said distal end of said expandable metal frame is positioned above a lower end of said first and second axial longitudinal members when said expandable metal frame is in said crimped orientation; a majority or all of each of said first and second articulating members does not extend above said upper end of said first or second axial longitudinal members that terminate at said proximal end of said expandable metal frame when said expandable metal frame is in said unexpanded crimped orientation and below said lower end of said first and second axial longitudinal members that terminate at said distal end of said expandable metal frame when said expandable metal frame is in said unexpanded crimped orientation; said expandable metal frame has a longitudinal foreshortening of no more than 5% along said longitudinal length of said expandable metal frame when expanded from said crimped orientation to said expanded orientation; said expandable metal frame has four or more properties selected from the group consisting of i) at least 70-100% of said expandable metal frame is formed of a metal alloy that has a yield strength of at least 110 ksi, ii) at least 70-100% of said expandable metal frame is formed of a metal alloy that has a modulus of elasticity of at least 35000 ksi, iii) said expandable frame has a frame geometry that has a maximum of nine of said frame cells in each of said cell rows, iv) at least 70-100% of said expandable metal frame is formed of a rhenium containing metal alloy that includes at least 15 awt. % rhenium and one or more metals selected from the group consisting of Mo, Cr, Co, Ni, Ti, Ta, Nb, Zr, and W, v) each of said first and second angular articulating members includes a plurality of arcuate portions along a longitudinal length of said first and second angular articulating members and vi) an outer surface of said expandable frame includes an enhancement layer; said enhancement layer includes one or more of chromium nitride (CrN), diamond-like carbon (DLC), titanium nitride (TiN), titanium nitride oxide ($TiNO_x$), zirconium nitride (ZrN), zirconium oxide (ZrO$_2$), zirconium-nitrogen-carbon (ZrNC), zirconium OxyCarbide (ZrOC), and zirconium oxynitride (ZrN$_x$O$_y$).

2. The expandable prosthetic heart valve as defined in claim 1, wherein each of said first and second axial longitudinal members of said first and second frame cells in each of said cell rows has a continuous linear shape along at least 90% of said longitudinal length of said first and second axial longitudinal members; each of said first and second axial longitudinal members of said first and second frame cells in each of said cell rows are spaced from one another and are positioned parallel to one another when said expandable frame is in said crimped orientation.

3. The expandable prosthetic heart valve as defined in claim 1, wherein said expandable metal frame consists of a) two cell rows, and wherein each of said cell rows includes the same number of said frame cells, and wherein a number of said frame cells in each of said cell rows is no more than nine, b) three cell rows, and wherein each of said cell rows includes the same number of said frame cells, and wherein a number of said frame cells in each row is no more than nine, or c) four cell rows, and wherein each of said cell rows includes the same number of said frame cells, and wherein a number of said frame cells in each of said cell rows is no more than nine.

4. The expandable prosthetic heart valve as defined in claim 1, wherein said longitudinal length of said expandable metal frame is equivalent to a sum of a total longitudinal length of said first axial longitudinal members in said first frame cells when said expandable metal frame is in said crimped orientation.

5. The expandable prosthetic heart valve as defined in claim 1, wherein a longitudinal length between said proximal end of said expandable metal frame and a commissural attachment area on a distal end of said expandable metal frame is constant when said expandable metal frame is both said crimped orientation and expanded orientation.

6. The expandable prosthetic heart valve as defined in claim 5, further including a commissural alignment structure that is positioned on said expandable metal frame; said commissural alignment structure is formed of a same material as said material used to form said expandable metal frame; said commissural alignment structure is positioned on top of at least one of said first and second axial longitudinal members; said commissural alignment structure has a different configuration from said first and second axial longitudinal members and said first and second angular articulating members.

7. The expandable prosthetic heart valve as defined in claim 6, wherein said material used to form said commissural alignment structure is a metal that has a density of greater than 10 mg/cm$^3$.

8. The expandable prosthetic heart valve as defined in claim 1, wherein a most distal cell row of said frame cells on said expandable metal frame includes has an odd number of said frame cells.

9. The expandable prosthetic heart valve as defined in claim 8, wherein said most distal cell row of said frame cells on said expandable metal frame includes nine said frame cells.

10. The expandable prosthetic heart valve as defined in claim 1, wherein each of said frame cells in a certain cell row has said angular articulating members that are of a same longitudinal length.

11. The expandable prosthetic heart valve as defined in claim 1, wherein vertices of adjacently positioned frame cells in adjacent cell rows are aligned to within no more than 5% of a total longitudinal length of said angular articulating members.

12. The expandable prosthetic heart valve as defined in claim 1, wherein a cross-sectional area of each of a most distal row of said frame cells and a cross-sectional area of each of a most proximal end of said frame cells on said expandable metal frame does not differ by more than 20%.

13. The expandable prosthetic heart valve as defined in claim 1, wherein said material of said expandable metal frame is at least partially made out of a metal alloy that includes less than 1 wt. % nickel.

14. A prosthetic heart valve for implantation into a heart; said prosthetic heart valve includes an expandable metal frame, a leaflet structure that is supported by said expandable metal frame, and an inner skirt that is supported by said expandable metal frame; said expandable metal frame is configured to expand from a crimped orientation to an expanded orientation when said prosthetic heart valve is positioned and secured at a treatment site in the heart; said expandable metal frame includes distal and proximal ends; said expandable metal frame includes a plurality of stacked cell rows that are stacked along the longitudinal length of said expandable metal frame; each of said cell rows includes a plurality of frame cells; each of said cell rows has a same number of said frame cells; each of said cell rows includes a first frame cell; each first frame cell in each of said cell rows includes a first axial longitudinal member and a second axial longitudinal member; each of said first and second longitudinal axial members extends along a longitudinal length of said expandable metal frame and first and second articulating members that are connected to said first and second axial longitudinal members; a longitudinal length of each of said first and second axial longitudinal members in said first frame cell is oriented parallel to a central axis of said expandable metal frame when said expandable metal frame is in said crimped and expanded orientations; each of said first axial longitudinal members in said first frame cell in each of said frame cell rows includes one end that is connected to an end of another of said first and second axial longitudinal members of at least one of said first frame cells in a different cell row; a top end of each set of connected together first axial longitudinal members defines a portion of said proximal end of said expandable metal frame; a bottom end set of each connected together first axial longitudinal members defines a portion of said proximal end of said expandable metal frame; a top end of a plurality of sets of connected together first axial longitudinal members defines a portion of said proximal end of said expandable metal frame; a bottom end of a plurality of sets of connected together first axial longitudinal members defines a portion of said proximal end of said expandable metal frame; a middle region of each of said first and second articulating members in each frame cell in said cell row that is located closest to said proximal end of said expandable metal frame is positioned below an upper end of said first and second axial longitudinal members when said expandable metal frame is in said crimped orientation; a middle region of each of said first and second articulating members in each frame cell in said cell row that is located closest to said distal end of said expandable metal frame is positioned above a lower end of said first and second axial longitudinal members when said expandable metal frame is in said crimped orientation; a majority or all of each of said first and second articulating members does not extend above said upper end of said first or second axial longitudinal members that terminate at said proximal end of said expandable metal frame when said expandable metal frame is in said crimped orientation and below said lower end of said first and second axial longitudinal members that terminate at said distal end of said expandable metal frame when said expandable metal frame is in said unexpanded crimped orientation; each of said first axial longitudinal members has a continuous linear shape along at least 80% of said longitudinal length of said first axial longitudinal member; a plurality of said second axial longitudinal members has a continuous linear shape along at least 80% of said longitudinal length of said first axial longitudinal member; said expandable metal frame has a longitudinal foreshortening of no more than 5% when said expandable metal frame is expanded from said crimped orientation to said expanded orientation.

15. The prosthetic heart valve as defined in claim 14, wherein a plurality of said first and second axial longitudinal members from a plurality of said cells are aligned along a same longitudinal axis and said plurality of said first and second axial longitudinal members that are aligned along said same longitudinal axis have a sum longitudinal length that is 100% of said longitudinal length of said expandable metal frame when said expandable metal frame is in said expanded orientation.

16. The prosthetic heart valve as defined in claim 14, wherein said expandable metal frame includes no more than four cell rows.

17. The prosthetic heart valve as defined in claim 16, wherein said expandable metal frame includes only two cell rows.

18. The prosthetic heart valve as defined in claim 14, wherein each of said first and second angular articulating members includes a plurality of arcuate portions along a longitudinal length of said first and second angular articulating members.

19. The prosthetic heart valve as defined in claim 14, wherein said expandable metal frame is partially or fully formed of a refractory metal alloy or a metal alloy that includes at least 15 awt. % rhenium; said metal alloy is not a shape memory alloy.

20. The prosthetic heart valve as defined in claim 14, wherein said expandable metal frame a) is formed of material that has a reduced recoil when bent such that said expandable metal frame has no more than 5% recoil when said expandable metal frame is crimped to said crimped orientation, b) is formed of material that has a reduced recoil when bent such that said expandable metal frame has no more than 5% recoil when said expandable metal frame is expanded from said crimped orientation to said expanded state, and/or c) has longitudinal foreshortening of no more than 5% when said expandable metal frame is expanded from said crimped orientation.

21. The prosthetic heart valve as defined in claim 14, wherein said leaflet structure includes a plurality of leaflets; each of said leaflets has an upper edge portion, a lower edge portion, and two side flaps; each side flap is connected to an adjacent side flap of another leaflet; at least a portion of said leaflet structure is connected to said expandable metal frame.

22. The prosthetic heart valve as defined in claim 14, further including an outer skirt; said outer skirt is positioned completely around a portion of an outside of said expandable metal frame; said outer skirt is connected to said expandable metal frame.

23. The prosthetic heart valve as defined in claim 14, said expandable metal frame has four or more of the following properties selected form the group consisting of i) is formed of a material that has a recoil of less than 10% when said expandable metal frame is expanded from said crimped orientation to said expanded orientation, ii) at least 70-100% of said expandable metal frame is formed of a metal alloy that has a yield strength of at least 110 ksi, iii) at least 70-100% of said expandable metal frame is formed of a metal alloy that has a modulus of elasticity of at least 35000 ksi, iv) said expandable metal frame has a frame geometry that has a maximum of nine of said frame cells per said cell row, v) at least 70-100% of said expandable metal frame is formed of a metal alloy that is formed of a rhenium containing metal alloy that includes at least 15 awt. % rhenium and one or more metals selected from the group consisting of Mo, Cr, Co, Ni, Ti, Ta, Nb, Zr, and W, vi) said expandable metal frame has longitudinal foreshortening along a longitudinal axis of said expandable metal frame of no more than 20% when said expandable metal frame is expanded from said crimped orientation to said expanded orientation, and vii) an outer surface of said expandable metal frame includes an enhancement layer, and wherein said enhancement layer includes one or more of chromium nitride (CrN), diamond-like carbon (DLC), titanium nitride (TiN), titanium nitride oxide ($TiNO_x$), zirconium nitride (ZrN), zirconium oxide ($ZrO_2$), zirconium-nitrogen-carbon (ZrNC), zirconium OxyCarbide (ZrOC), and zirconium oxynitride ($ZrN_xO_y$).

24. An expandable prosthetic heart valve comprising an expandable metal frame and a leaflet structure that is supported by said expandable metal frame; said expandable metal frame is configured to be expand from a crimped orientation to an expanded orientation in a body passageway; said expandable metal frame has distal and proximal ends; said expandable metal frame includes no more than four cell rows that are stacked along the longitudinal length of said expandable metal frame; each of said cell rows has the same number of frame cells; each of said frame cell in each of said cell rows includes a first and second axial longitudinal members and first and second articulating members; each of said first and second axial longitudinal members in said frame cell in each of said cell rows includes one end that is connected to an end of another of said first and second axial longitudinal members of at least one of said frame cells in a different cell row; a top end of each set of connected together first axial longitudinal members defines a portion of said proximal end of said expandable metal frame; a bottom end set of each connected together first axial longitudinal members defines a portion of said proximal end of said expandable metal frame; a top end of a plurality of sets of connected together first axial longitudinal members defines a portion of said proximal end of said expandable metal frame; a bottom end of a plurality of sets of connected together first axial longitudinal members defines a portion of said proximal end of said expandable metal frame; a first end of each of said first and second articulating members is connected to said first and second axial longitudinal members in each of said frame cells in each of said cell rows; said first and second axial longitudinal members are positioned parallel to a central axis of said expandable metal frame; said first and second axial longitudinal members are positioned parallel to on another when said expandable metal frame in said crimped and expanded orientations; a middle region of each of said first and second articulating members in each frame cell in said cell row that is located closest to said proximal end of said expandable metal frame is positioned below an upper end of said first and second axial longitudinal members when said expandable metal frame is in said crimped orientation; a middle region of each of said first and second articulating members in each frame cell in said cell row that is located closest to said distal end of said expandable metal frame is positioned above a lower end of said first and second axial longitudinal members when said expandable metal frame is in said crimped orientation; a majority or all of each of said first and second articulating members does not extend above said upper end of said first or second axial longitudinal members that terminate at said proximal end of said expandable metal frame when said expandable metal frame is in said unexpanded crimped orientation and below said lower end of said first and second axial longitudinal members that terminate at said distal end of said expandable metal frame when said expandable metal frame is in said unexpanded crimped orientation; said expandable metal frame has no longitudinal foreshortening along said longitudinal length of said expandable metal frame when expanded from said crimped orientation to said expanded orientation; said expandable metal frame includes two or more properties selected from the group consisting of a) has a recoil of less than 10% when said expandable metal frame is expanded from said crimped orientation to said expanded orientation, b) at least 70-100% of said expandable metal frame is formed of a metal alloy that has a yield strength of at least 110 ksi, c) at least 70-100% of said expandable metal frame is formed of a metal alloy that has a modulus of elasticity of at least 35000 ksi, d) said expandable metal frame has a frame geometry that has a maximum of nine frame cells per horizontal row, e) at least 70-100% of said expandable metal frame is formed of a metal alloy that is formed of a rhenium containing metal alloy that includes at least 15 awt. % rhenium and one or more metals selected from the group consisting of Mo, Cr, Co, Ni, Ti, Ta, Nb, Zr, and W, and f) an outer surface of said expandable metal frame includes an enhancement layer, and wherein said enhancement layer includes one or more of chromium nitride (CrN), diamond-like carbon (DLC), titanium nitride (TiN), titanium nitride oxide (TiNO$_x$), zirconium nitride (ZrN), zirconium oxide (ZrO$_2$), zirconium-nitrogen-carbon (ZrNC), zirconium OxyCarbide (ZrOC), and/or zirconium oxynitride (ZrN$_x$O$_y$).

25. The expandable prosthetic heart valve as defined in claim 24, wherein each of said first axial longitudinal members in each of said frame cells has a continuous linear shape along 100% of said longitudinal length of said first axial longitudinal member; a plurality of said second axial longitudinal members in each of said frame cells has a continuous linear shape along 100% of said longitudinal length of said second axial longitudinal member.

26. The expandable prosthetic heart valve as defined in claim 24, wherein said expandable metal frame is formed of a metal alloy that includes at least 15 awt. % rhenium; said metal alloy is not a shape memory alloy.

27. The expandable prosthetic heart valve as defined in claim 25, wherein said expandable metal frame is formed of a metal alloy that includes at least 15 awt. % rhenium; said metal alloy is not a shape memory alloy.

28. The expandable prosthetic heart valve as defined in claim 24, wherein said outer surface of said expandable metal frame includes said enhancement coating material.

29. The expandable prosthetic heart valve as defined in claim 22, wherein said outer surface of said expandable metal frame includes said enhancement coating material.

* * * * *